(12) United States Patent
Hossack et al.

(10) Patent No.: US 10,507,315 B2
(45) Date of Patent: Dec. 17, 2019

(54) SYSTEMS AND METHODS FOR ULTRASOUND IMAGING AND INSONATION OF MICROBUBBLES

(71) Applicant: University of Virginia Patent Foundation, Charlottesville, VA (US)

(72) Inventors: John A. Hossack, Charlottesville, VA (US); Brian R. Wamhoff, Charlottesville, VA (US); Alexander L. Klibanov, Charlottesville, VA (US); Johnny Chen, Chantilly, VA (US); Brent A. French, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 949 days.

(21) Appl. No.: 14/964,454

(22) Filed: Dec. 9, 2015

(65) Prior Publication Data
US 2016/0206867 A1    Jul. 21, 2016

Related U.S. Application Data

(62) Division of application No. 13/386,391, filed as application No. PCT/US2010/042783 on Jul. 21, 2010, now Pat. No. 9,237,898.
(Continued)

(51) Int. Cl.
*A61M 37/00*    (2006.01)
*A61B 8/12*    (2006.01)
(Continued)

(52) U.S. Cl.
CPC ......... *A61M 37/0092* (2013.01); *A61B 8/12* (2013.01); *A61B 8/445* (2013.01); *A61B 8/481* (2013.01);
(Continued)

(58) Field of Classification Search
CPC .. A61M 37/0092; A61M 37/00; A61M 25/00; A61M 25/10; A61M 25/0082;
(Continued)

(56) References Cited

U.S. PATENT DOCUMENTS

2004/0030250 A1    2/2004  Stewart
2004/0230213 A1    11/2004 Wulfman et al.
(Continued)

FOREIGN PATENT DOCUMENTS

WO    WO20090055720    4/2009

*Primary Examiner* — Peter Luong
(74) *Attorney, Agent, or Firm* — Law Office of Alan W. Cannon

(57) ABSTRACT

A catheter system including an elongate tubular member having a proximal end portion, a distal end portion and a lumen extending through at least a portion of a length of the elongate tubular member. The distal end portion of the elongate member is dimensioned and adapted to advance to or in proximity to a treatment site of a subject. A microbubble device is in fluid communication with the lumen. The microbubble device includes at least one input port for receiving a flow of material into the device and an output port configured to output microbubbles from the microbubble device. A second tubular member is in fluid communication with one of the at least one input ports. A pressure fitting arrangement is adapted to maintain a seal between the second tubular member and the input port.

9 Claims, 34 Drawing Sheets

Specification includes a Sequence Listing.

Related U.S. Application Data

(60) Provisional application No. 61/253,435, filed on Oct. 20, 2009, provisional application No. 61/298,741, filed on Jan. 27, 2010.

(51) Int. Cl.
| | | |
|---|---|---|
| *A61B 8/08* | (2006.01) | |
| *A61B 17/22* | (2006.01) | |
| *A61N 7/00* | (2006.01) | |
| *A61B 8/00* | (2006.01) | |
| *A61M 25/00* | (2006.01) | |
| *A61B 5/00* | (2006.01) | |
| *A61B 6/00* | (2006.01) | |
| *A61B 8/06* | (2006.01) | |
| *A61B 17/00* | (2006.01) | |
| *A61M 25/10* | (2013.01) | |
| *A61B 90/00* | (2016.01) | |

(52) U.S. Cl.
CPC .......... *A61B 17/22* (2013.01); *A61B 17/2202* (2013.01); *A61M 25/00* (2013.01); *A61M 37/00* (2013.01); *A61N 7/00* (2013.01); *A61B 5/7285* (2013.01); *A61B 6/503* (2013.01); *A61B 6/504* (2013.01); *A61B 6/541* (2013.01); *A61B 8/06* (2013.01); *A61B 8/0891* (2013.01); *A61B 8/543* (2013.01); *A61B 17/22004* (2013.01); *A61B 2017/00893* (2013.01); *A61B 2017/22021* (2013.01); *A61B 2017/22054* (2013.01); *A61B 2017/22067* (2013.01); *A61B 2017/22088* (2013.01); *A61B 2017/22089* (2013.01); *A61B 2090/3735* (2016.02); *A61B 2090/3784* (2016.02); *A61M 25/0082* (2013.01); *A61M 25/10* (2013.01); *A61M 2025/0073* (2013.01); *A61M 2025/1052* (2013.01); *A61N 2007/0039* (2013.01); *A61N 2007/0043* (2013.01)

(58) Field of Classification Search
CPC .. A61M 2025/1052; A61M 2025/0073; A61B 17/22; A61B 17/2202; A61B 17/22004; A61B 8/445; A61B 8/481; A61B 8/12; A61B 8/843; A61B 8/0891; A61B 8/06; A61B 2090/3784; A61B 2090/3735; A61B 5/7285; A61B 2017/22089; A61B 2017/22088; A61B 2017/22067; A61B 2017/22054; A61B 2017/22021; A61B 2017/00893; A61B 6/541; A61B 6/504; A61B 6/503; A61N 7/00; A61N 2007/0043; A61N 2007/0039
See application file for complete search history.

(56) References Cited

U.S. PATENT DOCUMENTS

| | | | |
|---|---|---|---|
| 2005/0084538 | A1 | 4/2005 | Dayton et al. |
| 2005/0197572 | A1 | 9/2005 | Williams et al. |
| 2006/0064009 | A1 | 3/2006 | Webler et al. |
| 2008/0281205 | A1* | 11/2008 | Naghavi ................ A61B 8/12 600/458 |
| 2008/0319309 | A1 | 12/2008 | Bredno et al. |
| 2009/0234231 | A1 | 9/2009 | Knight et al. |

* cited by examiner

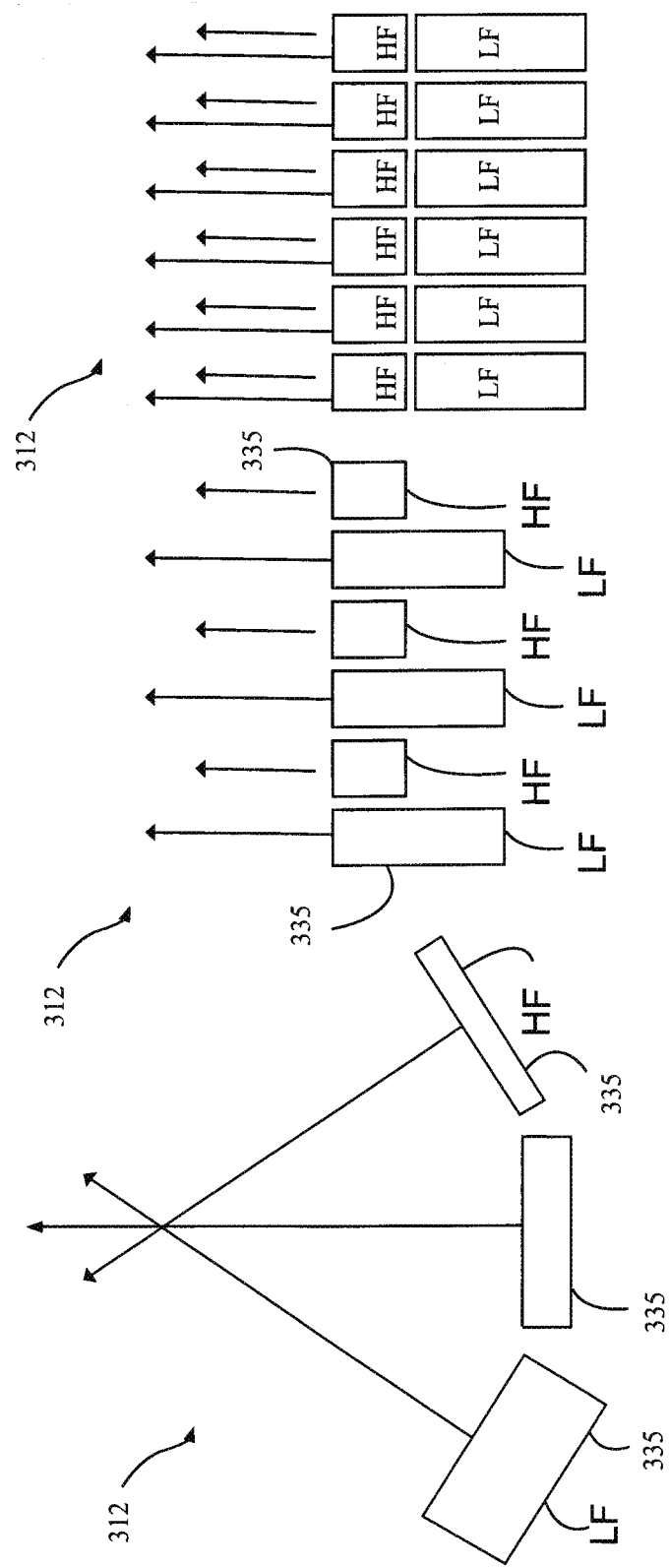

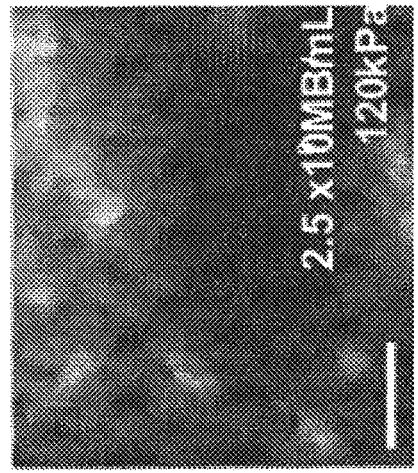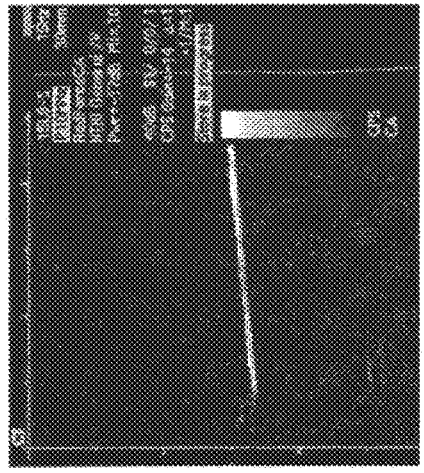
FIG. 11A  FIG. 11D
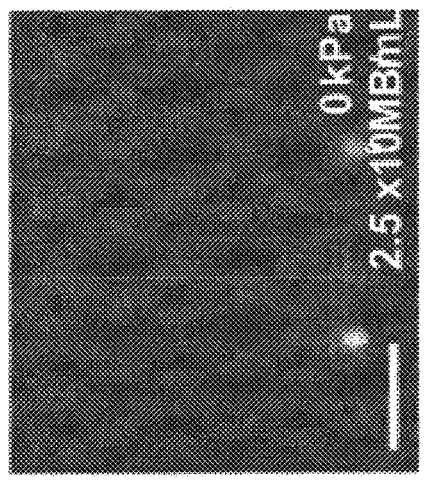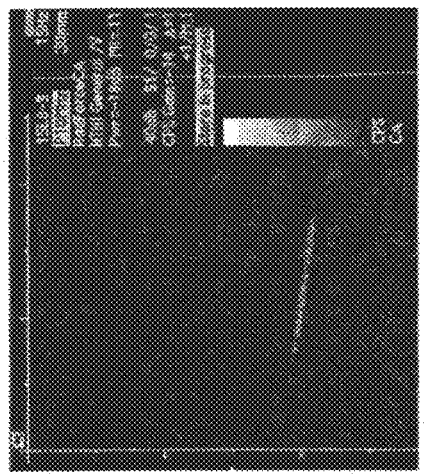
FIG. 11B  FIG. 11E
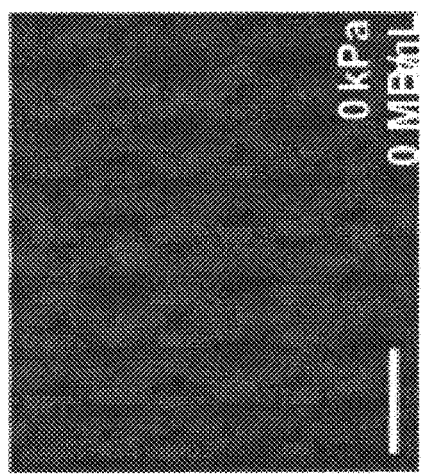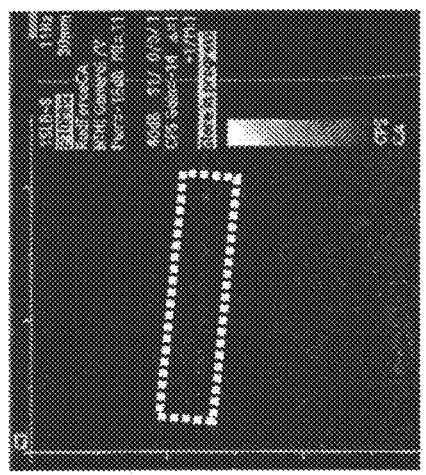
FIG. 11C  FIG. 11F Balloon occluder upstream and downstream of bubble port and ultrasound transducer(s)

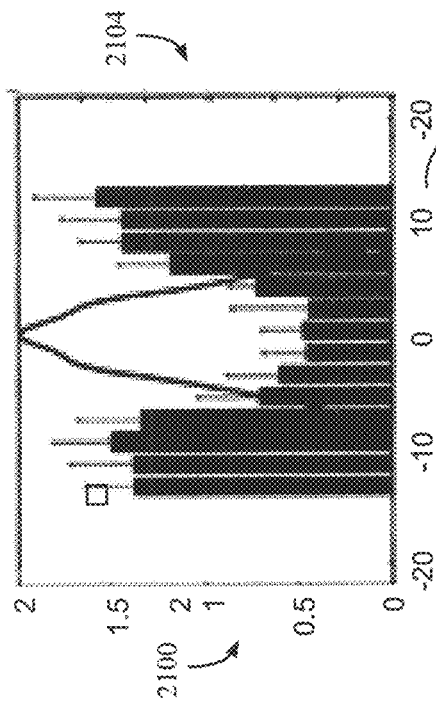
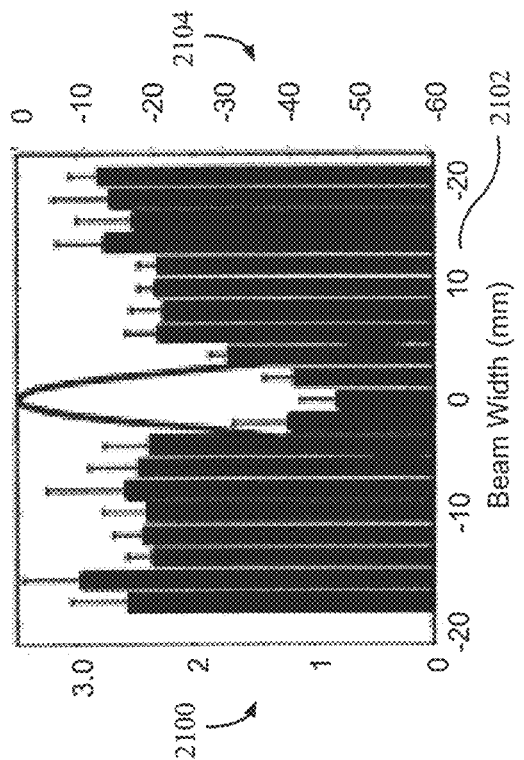
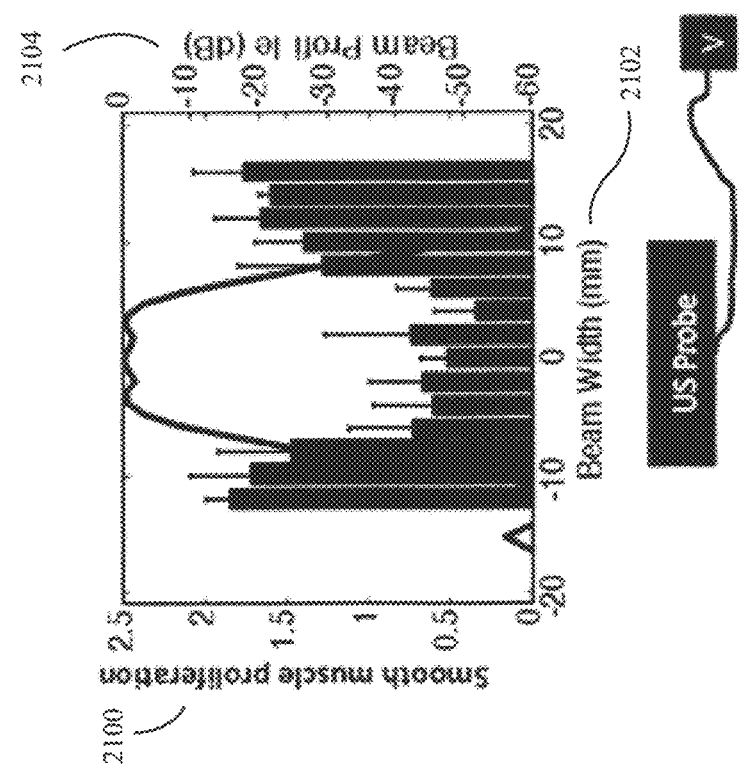
FIG. 21A
FIG. 21B
FIG. 21C

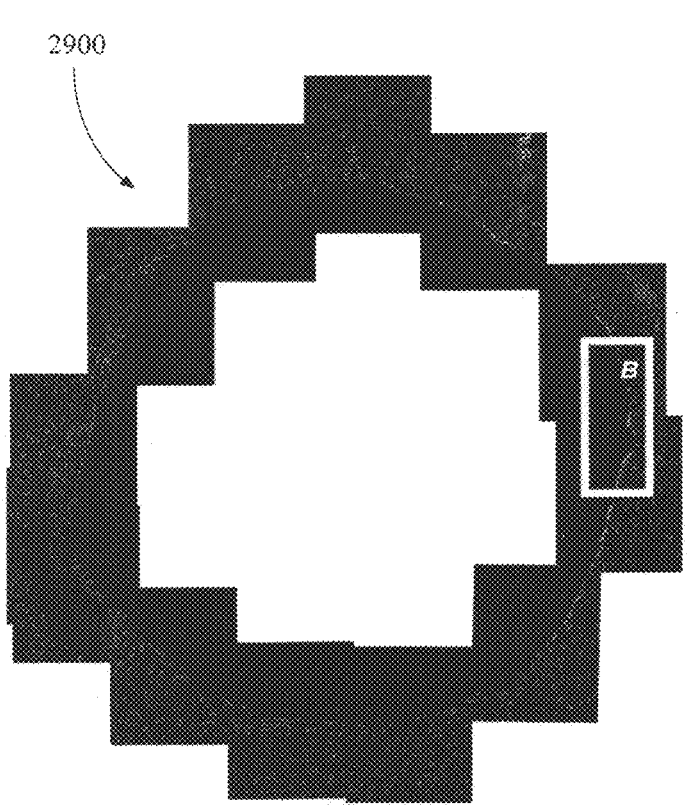
FIG. 30A  FIG. 30B
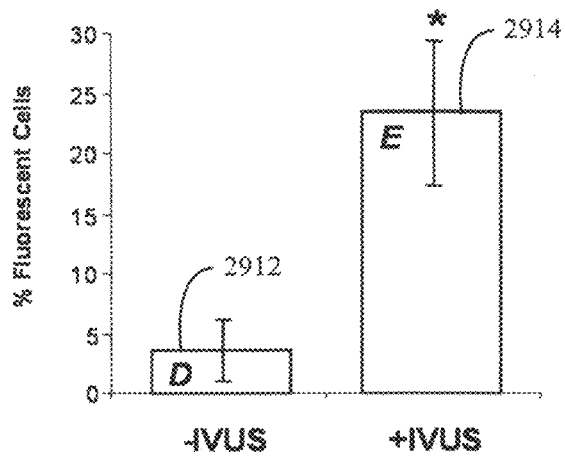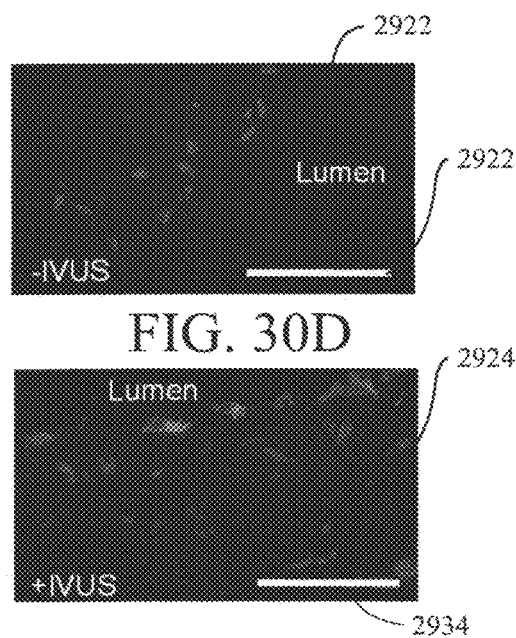
FIG. 30C  FIG. 30E
FIG. 30D

SYSTEMS AND METHODS FOR ULTRASOUND IMAGING AND INSONATION OF MICROBUBBLES

CROSS-REFERENCE

This application is a division of U.S. application Ser. No. 13/386,391, filed Jan. 20, 2012, which issued as U.S. Pat. No. 9,237,898 on Jan. 19, 2016, and which is an application that was filed under 35 U.S.C. 371 claiming priority to International Application PCT/US2010/042783 having an International Filing Date of 21 Jul. 2010, which claims the benefit of U.S. Provisional Application No. 61/227,284 filed Jul. 21, 2009 and titled "System for Treatment and Imaging Using Ultrasonic Energy and Microbubbles and Related Method Thereof; U.S. Provisional Application No. 61/253,435 filed Oct. 20, 2009 and titled "System for Treatment and Imaging Using Ultrasonic Energy and Microbubbles and Related Method Thereof; and U.S. Provisional Application No. 61/298,741 filed Jan. 27, 2010 and titled "System for Treatment and Imaging Using Ultrasonic Energy and Microbubbles and Related Method Thereof. application Ser. No. 13/386,391; PCT/US2010/042783; 61/227,284; 61/253,435; and 61/298,741 are each hereby incorporated herein, in their entireties, by reference thereto, and we claim priority to all of the aforementioned applications.

GOVERNMENT RIGHTS

This invention was made with government support under federal grant nos. R01 EB002185 and HL090700 awarded by the National Institutes of Health. The United States Government has certain rights in this invention.

The instant application contains a Sequence Listing which has been submitted electronically in ASCII format and is hereby incorporated by reference in its entirety. Said ASCII copy, created on Mar. 14, 2016, is named 20160315_Sequence_Listing_Computer_Readable_UVAPF_002DIV.txt and is 1 kilobyte in size.

BACKGROUND OF THE INVENTION

Cardiovascular disease (CVD) was blamed for 37% of the 2.4M deaths in the US (2003) [1]. CVD is the leading cause of death in the US and the developed world. Currently available drug-eluting stents (DES) pose a major potential health concern The clinical use of Drug Eluting Stents (DES), in relation to Bare Metal Stents (BMS), has evolved over a period of approximately 18 months from approximately 0% usage in the U.S., to the point where they were used in approximately 80% of coronary stent procedures in the U.S. [2, 3].

The above cited recent studies indicate that there is a significant, growing population (approximately 6 Million individuals worldwide [4]) who currently find themselves having been implanted with DES and face a choice between taking the expensive and risky drug clopidogrel—potentially for life—or increased risk of premature death.

The vascular smooth muscle cell, Vascular Cell Adhesion Molecule-1 (VCAM-1) and rapamycin: Vascular Smooth Muscle Cell (SMC) proliferation contributes to angioplasty-induced stenosis and in-stent restenosis.

The primary function of the vascular SMC in adult animals is contraction and SMCs express a unique repertoire of genes that allow for this specialized form of contraction, including SM α-actin, smooth muscle myosin heavy chain (SMMHC), SM22α, calponin, desmin, smoothelin—genes we refer to as SMC differentiation marker genes [5-8]. This repertoire of genes is typically used to describe the "contractile" phenotype or mature SMC.

VCAM-1 is a marker of the phenotypically modified/proliferating SMC.

The changes in SMC gene expression profiles associated with injury-induced phenotypic modulation are transient. That is, SMCs undergo phenotypic modulation as a natural response to repair the injured blood vessel, transitioning from a contractile phenotype to a synthetic phenotype but revert back to a contractile phenotype as the lesion resolves itself. Thus, this continuum of altered SMC gene expression profiles can be used to target the phenotypically modified SMC that invests in the developing neointima using molecular targeting. VCAM-1 (vascular cell adhesion molecule 1) is expressed in proliferating SMCs [9, 10] and transiently upregulated in SMCs following acute vascular injury and in atherosclerotic lesions [11]. The function of VCAM-1 is to promote cell-cell interaction required for SMC migration and recruitment or attraction of other cell types into the lesion, e.g. VCAM-1 interaction on SMCs with integrins on leukocytes, monocytes or macrophages (all inflammatory cells) [9]. Because VCAM-1 is expressed at much lower levels in the quiescent contractile SMC phenotype, but increased in proliferating SMCs, VCAM-1 can thus be used to target the proliferating SMC.

Rapamycin is a potent SMC anti-proliferative agent and the bench-mark agent for preventing in-stent restenosis by release from a DES. The cell cycle consists of 5 basic steps: dormancy (G0) or the contractile SMC phenotype, gap phase 1 (G1), synthesis (S), pre-mitosis or gap phase 2 (G2) and mitosis (M). In response to acute vascular injury, SMCs leave G0 and enter G1 to begin the process of cell proliferation and division into M phase; this is the synthetic migratory or proliferative SMC phenotype. The strategies for preventing SMC proliferation and entry into the cell cycle have been to block various phases of the cell cycle once the cell has left G0 in response to injury or some acute growth stimulus. Sirolimus, or rapamycin, and its analogues, ABT578 (Abbot Pharmaceuticals) and everolimus, are immunosuppressants with both anti-inflammatory and anti-proliferative properties that interfere early in the cell cycle by inhibiting the passage of cells from G1 to S phase. Drugs that inhibit cell cycle in the G1 phase are considered cytostatic and may be less toxic than drugs that act later in the cell cycle [12, 13]. Rapamycin is the most thoroughly investigated agent of this group and has become the bench-mark agent for the prevention of coronary artery restenosis [14]. Thus, because rapamycin is considered "cytostatic", SMCs treated with rapamycin do not die but maintain their viability in the growth arrested state.

Molecular Targeting of Microbubble Carriers

Recent research has investigated the feasibility of targeted ultrasound contrast microbubbles as a means of detecting intravascular manifestations of disease. Pathology is often accompanied by alterations of the endothelial cell layer lining of the affected blood vessels. This dysfunction may occur in the microcirculation, and is identified by the selective expression or up-regulation of certain molecules on the vascular endothelial surface. Many of the molecular markers of endothelial dysfunction corresponding to disease states such as atherosclerosis [15], transplant rejection [16], inflammation and ischemia reperfusion injury [17] are well characterized. However, there is currently no non-invasive, clinically approved technique to assess the extent and location of such vascular pathologies. Experimental formulations of targeted microbubbles, which contain a surfacebound ligand specific for the intended target, are injected intra vascularly and, after a short circulation period, are observed to accumulate at the target site. Subsequent ultrasound imaging enables determination of the location and extent of the targeted disease state [18]. This technique, known as "targeted contrast enhanced ultrasound", may achieve high spatial resolution, real time imaging, and a linear or other measurable correlation between adherent microbubbles and the received signal.

There is therefore a need for, among other things, the drug, the drug carrier, and the means of localizing delivery; and a means to guide the focal delivery under real time image guidance.

There is a need for improvements in delivery of drugs and/or genes to targeted locations and providing imaging capability to evaluate and facilitate such delivery.

SUMMARY OF THE INVENTION

An aspect of the present invention includes a catheter system comprising: an elongate tubular member having a proximal end portion, a distal end portion and a lumen extending through at least a portion of a length of the elongate tubular member, the distal end portion dimensioned and adapted to advance to or in proximity to a treatment site of a subject; a microbubble device in fluid communication with the lumen, the microbubble device including at least one input port for receiving a flow of material into the device and an output port configured to output microbubbles from the microbubble device; a second tubular member in fluid communication with one of the at least one input ports; and a pressure fitting arrangement adapted to maintain a seal between the second tubular member and the input port.

In at least one embodiment, the pressure fitting arrangement comprises a fillet of adhesive around a circumference of an interface between the second tubular member and the input port.

In at least one embodiment, the pressure fitting arrangement comprises an elongated insertion recess in the port.

In at least one embodiment, the elongated insertion recess is configured to pinch the second tubular member.

In at least one embodiment, the elongated insertion recess has a width greater than an outside diameter of the second tubular member and the elongated insertion recess has a height less than the outside diameter of the second tubular member.

In at least one embodiment, the pressure fitting arrangement comprises a macro chamber surrounding the microbubble device except for the output port, the macro chamber configured to be pressurized internally to an internal pressure greater than a pressure outside of the macro chamber.

In at least one embodiment, the macro chamber is pressurized to approximately the same pressure as an internal pressure of the microbubble device.

In at least one embodiment, approximately the same pressure refers to pressures within five pounds per square inch of the internal pressure of the microbubble device, preferably within two pounds per square inch.

In at least one embodiment, the internal pressure of the macro chamber is a pressure within the range of about five to about twenty pounds per square inch.

In at least one embodiment, the microbubble device comprises three of the input ports, and the macro chamber comprises three macro input ports in fluid communication with the three input ports of the microbubble device, the second tubular member is in fluid communication with one of the three macro input ports and a third tubular member is in fluid communication with at least one other of the three macro input ports.

In at least one embodiment, the microbubble device comprises three of the input ports, a third tubular member in fluid communication with a second of the input ports and a forth tubular member in fluid communication with a second of the input ports.

In at least one embodiment, the microbubble device comprises three of the input ports, and a third tubular member in fluid communication with a second and a third of the input ports.

In at least one embodiment, the second tubular member extends through the lumen of the elongate tubular member and is in fluid communication with one of the at least one input ports, wherein the microbubble device comprises three of the input ports, and wherein two of the input ports are in fluid communication with a space defined between an outer wall of the second tubular member and an inner wall of the elongate tubular member.

In at least one embodiment, the second tubular member is configured to deliver gas to the microbubble device and the two of the input ports in fluid communication with the space defined between the outer wall of the second tubular member and the inner wall of the elongate tubular member are configured to receive liquid for forming shells of bubbles.

In at least one embodiment, the second tubular member extends through the elongate tubular member and is in fluid communication with one of the at least one input ports, wherein the microbubble device comprises three of the input ports, wherein a third tubular member extends through the elongate tubular member and is in fluid communication with a second of the input ports, and wherein a third of the input ports is in fluid communication with a space defined between outer walls of the second and third tubular members and an inner wall of the elongate tubular member.

In at least one embodiment, the second and third tubular members are configured to deliver liquid to the two input ports for forming shells of bubbles, and the third input port is configured to receive gas.

In at least one embodiment, the second tubular member extends through the lumen of the elongate tubular member and is in fluid communication with one of the at least one input ports, wherein the microbubble device comprises three of the input ports, and wherein third and fourth tubular members extend through the elongate tubular member and are in fluid communication with second and third ports of the three input ports.

In at least one embodiment, the second tubular member is configured to deliver gas to the one input port and the third and fourth tubular members are configured to deliver liquid to the second and third ports for forming shells of bubbles.

In at least one embodiment, the microbubble device is fixed in the distal end portion of the elongate tubular member, and wherein the output port opens directly through a distal end of the elongate tubular member or a wall of the distal end portion of the elongate tubular member.

In at least one embodiment, the output port outputs out of the distal end of the elongate tubular member at or near a central, longitudinal axis of the elongate tubular member.

In at least one embodiment, the microbubble device comprises a microfluidics device.

In at least one embodiment, the system includes a a pump, and control circuitry configured to output electrical signals to control the pump to output microbubbles from the elongated tubular member.

In at least one embodiment, the control circuitry is configured to receive input signals characterizing an ECG waveform and to output signals to the pump, to drive the pump to control output of microbubbles generated by the microbubble device out of the elongate tubular member, thereby pacing microbubble output from the elongated tubular member to a cardiac cycle characterized by the ECG waveform.

In at least one embodiment, the control circuitry is configured to include a delay time between a detected wave of the ECG waveform used to trigger the pump, wherein the delay time is a function of distance of a target location for delivery from the heart that the ECG waveform is being detected from.

In at least one embodiment, the pump is configured to drive output of microbubbles generated by the microbubble device out of the elongate tubular member, to continuously output microbubbles.

In at least one embodiment, a transducer is in the distal end portion of the elongate tubular member, the transducer being configured to transduce electrical energy to ultrasonic energy and to transduce ultrasonic energy to electric energy.

In at least one embodiment, the transducer is operable in an imaging mode to image an object external to the elongate tubular member and is also operable in a bursting mode to burst microbubbles using ultrasonic energy.

In at least one embodiment, the output port of the elongate tubular member comprises a plurality of output ports arranged circumferentially in a ring and adapted to direct microbubbles in a pattern circumscribing the elongate tubular member.

In at least one embodiment, the output port comprises a plurality of output ports arranged circumferentially in set of offset rings.

In at least one embodiment, a motion stage is configured to perform at least one of translating and rotating at least a portion of the elongate tubular member.

In at least one embodiment, the transducer comprises an imaging transducer configured to operate in the imaging mode and a bursting transducer configured to operate in the bursting mode.

In at least one embodiment, the imaging transducer and the bursting transducer are made coincident by placing one over the other.

In at least one embodiment, the imaging transducer and the bursting transducer are arranged offset from one another.

In at least one embodiment, the elongate tubular member further comprises an additional lumen and an imaging catheter position in the additional lumen.

In at least one embodiment, the imaging catheter comprises an optical coherence tomography (OCT) imaging catheter.

In at least one embodiment, an imaging catheter fixed side-by-side to the elongate tubular member.

In at least one embodiment, the imaging catheter comprises an optical coherence tomography (OCT) imaging catheter.

In at least one embodiment, a plurality of wires are exposed to a surface of the distal end portion and configured to apply AC or DC electrical energy therebetween.

In at least one embodiment, the wires are arranged along a direction of a longitudinal axis of the elongate tubular member.

In at least one embodiment, the wires may be connected alternately to provide for electric fields between pairs of the wires.

In at least one embodiment, a heating element is provided in thermal communication with the distal end portion of the elongate tubular member.

In another aspect of the present invention, a microbubble is designed for lack of longevity, and comprises: a lipid shell a lipid shell that is filled with a gas selected from the group consisting of air, nitrogen and oxygen.

In at least one embodiment, the microbubble has an outside diameter in the range of about 10 µm to about 20 µm.

In another aspect of the present invention, a microbubble comprises: a cationic lipid shell surrounding a core containing decafluorobutane gas; plasmids coupled to the cationic shell by electrostatic charge; and spacers separating at least some of the plasmids.

In at least one embodiment, the plasmids comprise p-miR-laxZ plasmids.

In at least one embodiment, the spacers comprise polyethylene glycol.

In at least one embodiment, a ratio of the plasmids to the microbubbles is about 1 µg plasmids per $5 \times 10^6$ microbubbles.

In another aspect of the present invention, a system for ultrasound-mediated insonation of conjugated microbubbles to reduce gene expression in cells in vitro is provided, including: an optically transparent and acoustically penetrable cell configured for placement of the cells; the conjugated microbubbles; an ultrasonic transducer mounted on a motion controller linear stage; and a controller configured to input signals defining waveforms, pulse repetition frequencies and wave amplitudes to the transducer and to vary pulse lengths and peak pressures.

In at least one embodiment, the microbubbles are coupled with p-miR-lacZ plasmid.

In at least one embodiment, the microbubbles are coupled with RNAi.

In at least one embodiment, the cells comprise endothelial and smooth cell lines cultured from ROSA 26 mouse aorta.

In at least one embodiment, the microbubbles are coupled with p-miR-eGFP.

In another aspect of the present invention, a method of performing gene transfection in a tissue is provided, including: positioning an output port of a device at or in proximity to a location of the tissue to be transfected; infusing microbubbles from the output port into or proximal to the tissue to be transfected, wherein the microbubbles comprise plasmid DNA; and delivering ultrasonic energy from the device to the microbubbles at a frequency and power sufficient to rupture the microbubbles.

In at least one embodiment, the plasmid DNA is coupled with the microbubbles.

In at least one embodiment, the method is performed in vitro.

In at least one embodiment, the method is performed in vivo.

In at least one embodiment, the plasmid DNA is selected from the group consisting of: p21, p53, and KLF4.

In at least one embodiment, the positioning includes advancing the device invasively into a subject.

In at least one embodiment, the advancing comprises advancing the device intravascularly.

In at least one embodiment, the method further includes performing angioplasty on a vessel at the location of the tissue to be treated, prior to performing the positioning.

In at least one embodiment, the method further includes confirming accuracy of the positioning by imaging placement of the device during or after performing the positioning.

In at least one embodiment, the imaging comprises performing angiography.

In at least one embodiment, the imaging comprises ultrasonic imaging.

In at least one embodiment, the microbubbles are infused to a location upstream of the tissue to be transfected.

In at least one embodiment, the tissue to be transfected is part of an artery.

In at least one embodiment, the artery is a coronary artery.'

In another aspect of the present invention, a method of providing therapy to a treatment site of tissue of a subject is provided, including: flowing microbubbles over the treatment site, wherein the microbubbles comprise molecular targeted, drug charged microbubbles that selectively adhere to the tissue to be treated, based on at least one molecular marker; and bursting the microbubbles that are adhered to the tissue to be treated.

In at least one embodiment, the flowing comprises dispensing the microbubbles from at least one port of a catheter.

In at least one embodiment, the method includes performing at least one of translating and rotating a portion of a device at a location where the microbubbles are dispensed while performing the flowing.

In at least one embodiment, the molecular targeted, drug charged microbubbles are targeted to a molecule selected from the group consisting of: VCAM-1, alphaVbetaIII and P-Selectin.

In at least one embodiment, the molecular targeted, drug charged microbubbles employ peptide-based targeting.

In at least one embodiment, the molecular targeted, drug charged microbubbles employ antibody-based targeting.

In at least one embodiment, the bursting of the microbubbles comprises applying acoustic radiation force to the microbubbles.

In at least one embodiment, the treatment site is internal to a subject, and the method further includes: advancing a catheter invasively into a subject; and wherein the flowing comprises dispensing the microbubbles from the catheter.

In at least one embodiment, the advancing comprises advancing the device intravascularly.

In at least one embodiment the bursting of the microbubbles comprises applying acoustic radiation force to the microbubbles, the force being applied from a transducer located within the catheter.

In at least one embodiment, the method further includes viewing the treatment site via imaging performed through the catheter.

In at least one embodiment, the imaging is performed ultrasonically.

In at least one embodiment, the method further includes allowing the microbubbles to accumulate on the treatment site for a predetermined time, and then performing the viewing to examine an extent of the tissue to be treated at the treatment site.

In another aspect of the present invention, a method of assessing a treatment site of tissue of a subject to be treated is provided, including: advancing a catheter invasively into a subject, so that a distal end portion of the catheter is placed at or in proximity to the treatment site; dispensing the microbubbles from the catheter in a manner that the microbubbles flow over the treatment site, wherein the microbubbles comprise molecular targeted, drug charged microbubbles that selectively adhere to the tissue to be treated, based on at least one molecular marker; allowing the microbubbles to accumulate on the treatment site for a predetermined time commencing from beginning of the dispensing, and after passage of the predetermined time, viewing the treatment site to examine the size of the area of the treatment site.

In at least one embodiment, the viewing is performed ultrasonically, using an ultrasonic transducer located in the catheter.

In at least one embodiment, the microbubbles are configured to be ruptured by acoustic radiation force to effect drug delivery to the treatment site.

In at least one embodiment, at least a portion of the catheter is swept axially and rotationally during the dispensing to achieve coverage of the treatment site with the microbubbles.

In at least one embodiment, the method further includes bursting the microbubbles by applying acoustic radiation force to the microbubbles, the force being applied from a transducer located within the catheter; and viewing the treatment site again, via ultrasonic imaging by the catheter, to verify that all microbubbles covering the treatment site have been burst.

In at least one embodiment, the method further includes repeating the bursting and viewing again steps when it is determined by viewing that not all microbubbles have yet been burst.

In another aspect of the present invention, a method of providing therapy to a treatment site of a subject is provided, including: advancing a distal end portion of an ultrasound catheter to or in proximity to the treatment site; dispensing microbubbles from the catheter according to a pacing protocol and in a manner that the microbubbles flow over the treatment site, wherein the dispensing according to the pacing protocol dispenses the bubbles in a timed manner relative to the cardiac cycle of the subject; and bursting the microbubbles to dispense drug or gene therapy to the treatment site.

In at least one embodiment, the bursting is performed by applying acoustic radiation force to the microbubbles, the force being applied from a transducer located within the catheter.

In at least one embodiment, the method further includes viewing the treatment site via ultrasonic imaging provided by applying ultrasonic energy to the treatment site from a transducer located within the catheter.

In at least one embodiment, the treatment site is at least a portion of a blood vessel, organ, parenchymal tissue, stromal tissue or duct.

In at least one embodiment, the treatment site is at least a portion of a blood vessel.

In at least one embodiment, the method further includes sensing an ECG waveform of the cardiac cycle of the subject, wherein the pacing is according to the ECG waveform having been sensed.

In at least one embodiment, the method further includes adding a delay period to commencement of dispensing, relative to the ECG waveform, based on distance of the treatment site from the heart of the subject.

In at least one embodiment, the microbubbles are delivered through a lumen extending through the catheter.

In at least one embodiment, the microbubbles are formed in the distal end portion of the catheter and dispensed therefrom.

These and other features of the invention will become apparent to those persons skilled in the art upon reading the details of the systems, devices and methods as more fully described below.

BRIEF DESCRIPTION OF THE DRAWINGS

The accompanying drawings, which are incorporated into and form a part of the instant specification, illustrate several aspects and embodiments of the present invention and, together with the description herein, and serve to explain the principles of the invention. The drawings are provided only for the purpose of illustrating select embodiments of the invention and are not to be construed as limiting the invention.

FIGS. 3(A)-(C) schematically illustrate the arrays of the Forsberg array, Bouakaz array, and present invention embodiment array, respectfully.

FIG. 8 illustrates: at FIG. 8(A) a low frequency layer pulse-echo response; at FIG. 8(B) an Experimental high frequency pulse-echo response; at FIG. 8(C) an experimental high frequency pulse echo response after inverse filtering; and at FIG. 8(D) an FEA simulation of proposed, improved (better acoustic matching) high frequency layer design (without filtering) All plots are voltage echo response vs. time (μs)

FIGS. 11(A)-11(E) illustrate epifluorescence microscopy observations (FIGS. 11(A), 11(B) and 11(C)) and ultrasound backscatter imaging (FIGS. 11(D), 11(E), 11(F)) of adherent microbubbles. Microcapillaries infused with buffer alone show no microbubble adhesion (FIG. 11(A) and no ultrasound signal (dashed box illustrates microcapillary location) (FIG. 11 (D)). Few adherent microbubbles are visible in flow-only microcapillaries (FIG. 11 (B)), and the corresponding echo is identifiable but weak. A large number of adherent microbubbles are present in a microcapillary exposed to radiation force at 122 kPa (FIG. 11 (C)), and the corresponding echo is strong. Scale bar represents 5 μm.

FIGS. 21A-21C graphically illustrate that delivery of rapamycin (Sirolimus) via microbubbles in vitro to smooth muscle cells only prevents proliferation where the ultrasound is applied.

FIGS. 30A-30E show results from the experimental procedures described in the timeline of FIG. 29.

DETAILED DESCRIPTION OF THE INVENTION

Before the present systems, devices and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a lumen" includes a plurality of such lumens and reference to "the transducer" includes reference to one or more transducers and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Figure 1:
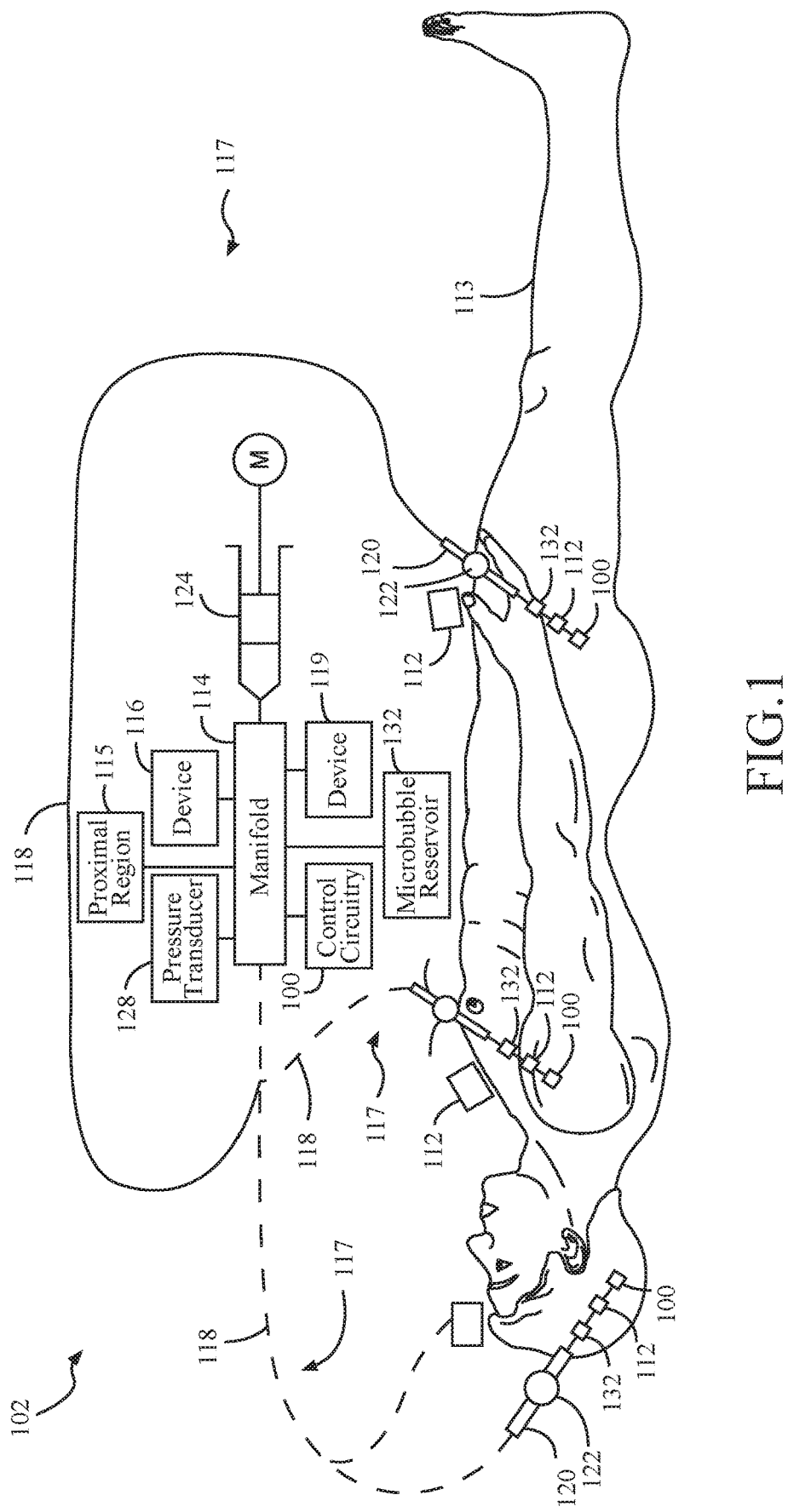
FIG. 1 provide a schematic illustration of an embodiment (or partial embodiment) of the present invention ultrasound catheter system 102 for providing therapy (and/or diagnosis) to a treatment site at one or more locations of a subject.

FIG. 1 provides a schematic illustration of an embodiment (or partial embodiment) of the present invention ultrasound catheter system 102 for providing therapy to a treatment site at one or more locations of a subject. The system 102 may comprise a tubular member 118 such as a catheter or multiple catheters. The catheter(s) 118 having a proximal region 115 and distal region 117, whereby the proximal end of the ultrasound catheter is adapted or configured to be advanced to or in proximity to the subject's treatment site. It should be appreciated that any one of the catheters as shown may be a plurality of catheters and any given catheter may have one or more lumens or channels therein. The system further comprises a microbubble reservoir 132 in hydraulic communication with the tubular member. The microbubble reservoir is 132 may be located in the proximal region 115 and/or the proximal region 117 as desired or required. The microbubble reservoir is 132 may be adapted to release microbubbles that are intended to be located into or proximal to the treatment site. The system further comprises an ultrasonic energy 112 source in communication with the proximal region 115 and/or distal region 117 of the tubular member 118. The ultrasonic energy 112 may be capable of: imaging the treatment site, and/or rupturing the microbubbles. The ultrasonic energy 112 may be located outside or at least partially surrounding the subject 113 or patient. The system further comprises a control circuitry 100 or controller configured to send electrical activation to the ultrasonic energy source 112 or any components or subsystem affiliated with the catheter system 102. Further, the ultrasonic energy source 112 may provide ultrasonic radiation forces for translating the microbubbles into or in the vicinity of the treatment site; or alternatively the mechanical forces may be provided for translating the microbubbles into or in the vicinity of the treatment site, as well as a combination of both mechanical and ultrasonic forces (acoustic wave) to achieve the desired or required result.

The tubular member 118 and other components and subsystems affiliated with the catheter system 102 may be manufactured in accordance with a variety of techniques known to an ordinarily skilled artisan. Suitable materials and dimensions can be readily selected based on the natural and anatomical dimension of the treatment or diagnosis site and on desired percutaneous access site or exterior.

For example, in an exemplary embodiment, the tubular body proximal region 115 and/or distal region 117 comprise a material that has sufficient flexibility, kink resistance, rigidity and structural support to push the ultrasound energy source 112 through the patient's vasculature or organ to a treatment site or vicinity thereof. Examples of such materials include, but are not limited to, extruded polytetrafluoroethylene ("PTFE"), polyethylenes ("PE"), Pebax—made by Arkema, polyamides and other similar materials. In certain embodiments, the tubular body proximal region 115 and/or distal region 117 is reinforced by braiding, mesh or other constructions to provide increased kink resistance and ability to be pushed. For example, nickel titanium or stainless steel wires can be placed along or incorporated into the tubular member or body 118 to reduce kinking. For example, various guidewires, sheaths and additional tubular members may be implemented to handle the communications, navigations, controlling and imaging, etc.

It should be appreciated that the aforementioned catheter device, reservoir, ultrasound, and controller may be disposed entirely inside the applicable location of the subject as desired or required, outside the location of the subject as desired or required or a combination of inside or outside the location of the subject. The one or more locations of the subject may be an organ. The organ may include hollow organs, solid organs, parenchymal tissue, stromal tissue, and/or ducts. The one or more locations of the subject may be a tubular anatomical structure. The tubular anatomical structure may be a blood vessel. Further, for example, the treatment site may be a vasculature treatment site comprising at least one of the following: stenotic region or any region exhibiting vascular disease.

In an approach, a manifold and/or axis port 114 couples several therapeutic and/or diagnostic devices typified by device 116 to the catheter system 102. A syringe, flow-driver or pumping device 124 is also in communication with the manifold 114. The catheter system 102 in turn may be delivered through a guide sheath 120 that may be in communication with a navigation guide 122. In operation the physician or user inserts one or more such catheter system 102 into the body of the subject 113, for instance on going into the leg, chest or skull (or other anatomical part or parts or subject region or regions to cover the hollow or solid organs, blood vessels, etc.) under imaging guidance or other applicable examination or intervention. The same or similar ultrasound visualization may be used to follow the progress of the one or more implant(s) both acutely and chronically. This catheter device may have various interior and peripheral lumens, chambers and channels. Such interior and peripheral lumens, chambers and channels may be used to deliver other devices and perform various diagnostic functions. For example, each lumen, chamber, and channel may communicate with a separate port of the manifold 114. A lumen, chamber or channel may contain a pressure transducer 128. Other lumens and channels may be devoted to an optical or other type of cell counter device, for example, as shown generically as device 119 in FIG. 1. Such a device may operate with two optical fibers (optical device or counter) located in two separate lumens and/or ports to measure the number of and viability of cells, agents, drugs or microbubbles delivered by the catheter. An example of fiber optics related application/technology is discussed in U.S. patent application Ser. No. 10/444,884, filed May 23, 2003 (U.S. Application No. 2003/0204171, published Oct. 30, 2003), and of which are hereby incorporated by reference herein in their entirety. Further referred to are WO 2009/055720 (PCT/US2008/081189) filed Oct. 24, 2008 and U.S. patent application Ser. No. 12/739,128 filed Apr. 21, 2010, each of which are hereby incorporated herein, in their entireties, by reference thereto. It should be appreciated that many other embodiments of controller, catheter system, ultrasound energy source(s), manifold and/or axis port, proximal region, therapeutic and/or diagnostic devices, distal region, tubular member, other lumen(s), pressure transducer, microbubble reservoir, microbubble propeller or microbubble translator or propeller, flow channeling and recirculation means, microcoil means, pump means, pressure and flow-rate monitor means, imaging means, computer means, drug-eluting stents (DES), and other details of construction and use constitute non-inventive variations of the novel and insightful conceptual means, system, and technique which underlie the present invention. Examples of systems and methods that may be implemented with various embodiments of the present invention are provided in the following commonly owned applications: U.S. patent application Ser. No. 10/444,884, filed May 23, 2003 (US Application No. 2003/0204171, published Oct. 30, 2003); PCT Application No. PCT/US2005/026738, filed Jul. 28, 2005; and PCT Application No. 2006/005876, filed Feb. 16, 2006, and of which are hereby incorporated by reference herein in their entirety. It should be appreciated that as discussed herein, a subject may be a human or any animal.

It should be appreciated that an animal may be a variety of any applicable type, including, but not limited thereto, mammal, veterinarian animal, livestock animal or pet type animal, etc. As an example, the animal may be a laboratory animal specifically selected to have certain characteristics similar to human (e.g. rat, dog, pig, monkey), etc. It should be appreciated that the subject may be any applicable human patient, for example.

Figure 2A:
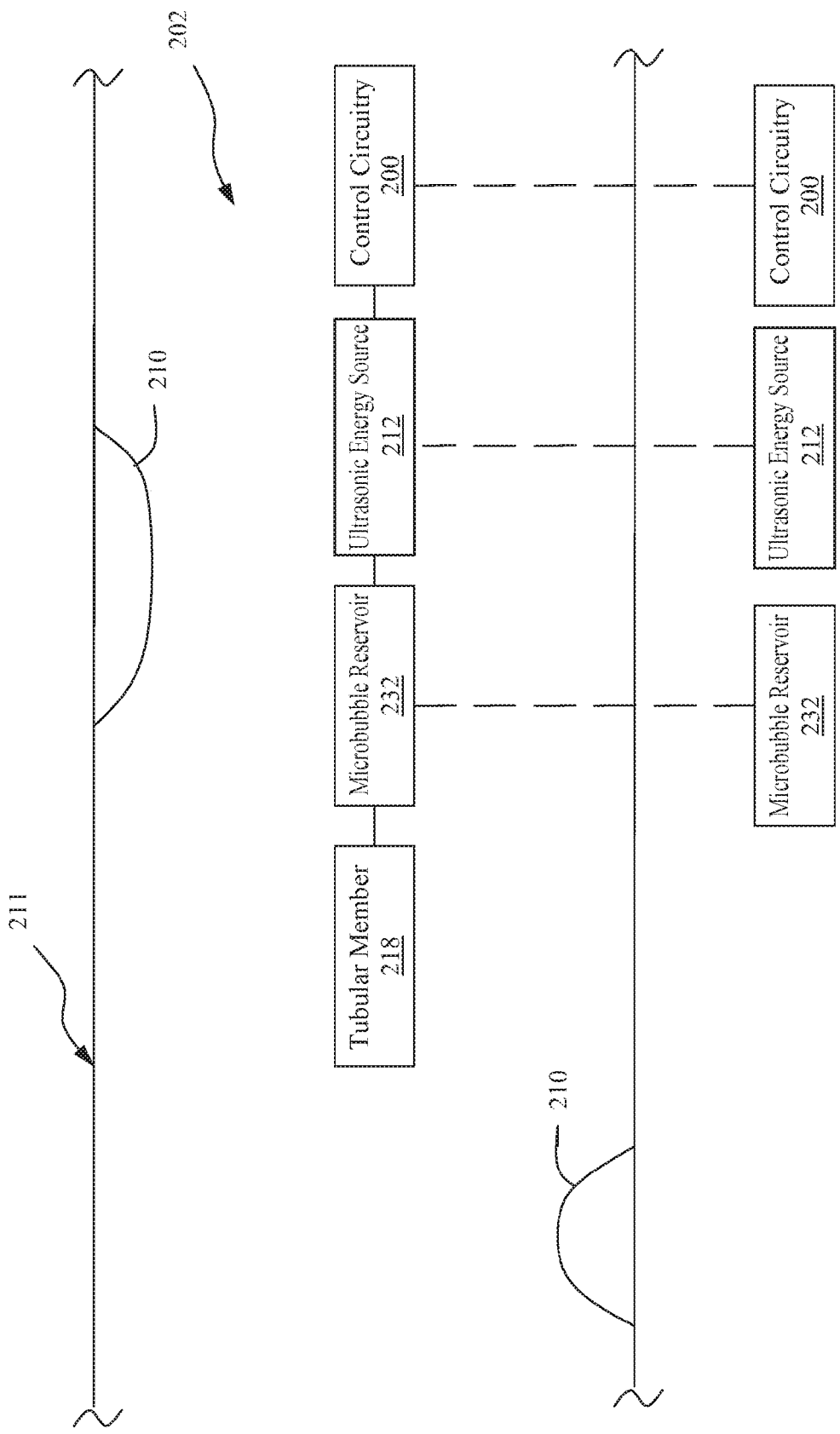
FIGS. 2(A)-(C) schematically illustrate various embodiments (or partial embodiments) of the present invention ultrasound catheter system for providing therapy (and/or diagnosis) to a treatment site at one or more locations of a subject.
Figure 2B:
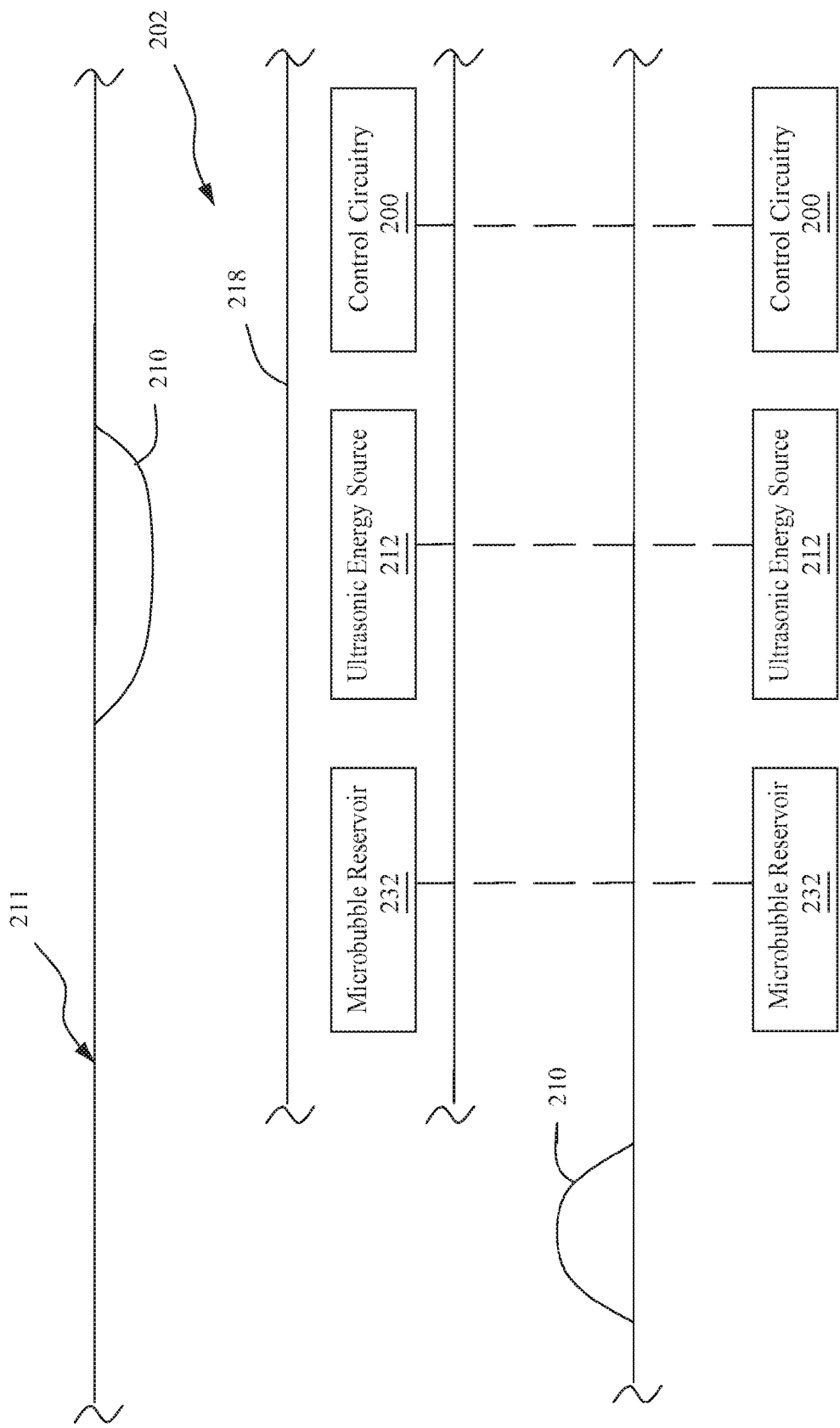
Figure 2C:
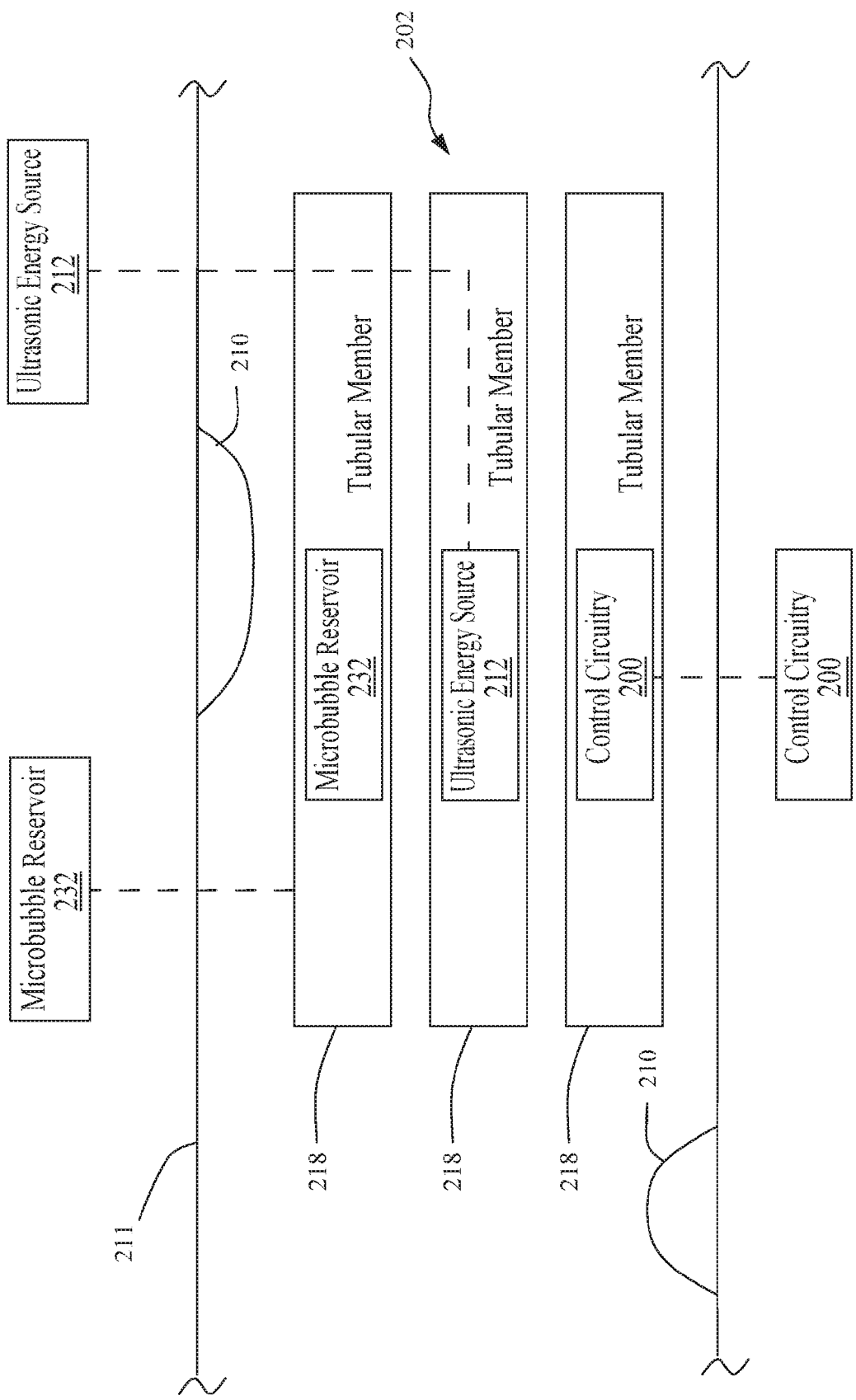

FIGS. 2(A)-(C) schematically illustrate various embodiments (or partial embodiments) of the present invention ultrasound catheter system for providing therapy to a treatment site at one or more locations of a subject. The catheter system 202 may comprise a tubular member 218 such as a catheter or multiple catheters. The catheter(s) having a proximal region and distal region, whereby the proximal end of the ultrasound catheter is adapted or configured to be advanced to or in proximity to the subject's treatment site. It should be appreciated that any one of the catheters 218 as shown may be a plurality of catheters and any given catheter may have one or more lumens therein. The system further comprises a microbubble reservoir 232 in hydraulic communication with the tubular member 218 and any lumens, channels, controllers or communication devices. The microbubble reservoir 232 is adapted to release microbubbles that are intended to be located into or proximal to the treatment site 210 at the desired or applicable location 211 of the subject. The system 202 further comprises an ultrasonic energy source 212 in communication with the distal region (or other region as desired or required) of the tubular member 218 (or other components or subsystems of the present invention). The ultrasonic energy is adapted for or capable of: imaging the treatment site 210, and rupturing the microbubbles.

The system 202 further comprises a control circuitry 200 configured to send electrical activation to the ultrasonic energy source 212, as well as other components and subsystems of the present invention. Further, the ultrasonic energy source 212 may provide ultrasonic radiation forces for translating the microbubbles into or in the vicinity of the treatment site 210 at the desired or applicable location 211 of the subject; or alternatively the mechanical forces may be provided for translating the microbubbles into or in the vicinity of the treatment site 210, as well as a combination of both mechanical and ultrasonic forces (acoustic wave) to achieve the desired or required result.

It should be appreciated that the aforementioned catheter 218, reservoir 232, ultrasound 212, and controller 200 may be disposed entirely inside the applicable location of the subject, outside the location of the subject or a combination of inside or outside the location of the subject. The one or more locations 211 of the subject may be an organ. The organ may include hollow organs, solid organs, parenchymal tissue, stromal tissue, and/or ducts. The one or more locations 211 of the subject may be a tubular anatomical structure. The tubular anatomical structure may be a blood vessel. Further, for example, the treatment site 210 may be a vasculature treatment site comprising at least one of the following: stenotic region or any region exhibiting vascular disease. Further, for example, the treatment site 210 may be a vasculature treatment site and/or a diagnostic site.

Development of Transducer/Instrumentation to Optimize Delivery of a Therapeutic Agent by Microbubble Carrier.

Spatially localized, focused, non-invasive/minimally invasive treatments require appropriate non-invasive real time imaging to guide the localization of the therapeutic (focal) region with respect to selected target site in the context of surrounding anatomy. This point may seem simple but it has profound implications for non-invasive treatment. This paradigm further suggests attention be paid to ensuring that the focused treatment zone be accurately and reliably aligned with whatever non-invasive imaging is used. The ideal model would be that the image plane is coincident with the therapeutic point, line or plane. Frequently, a small imaging array is placed centrally within an aperture "cut out" from a larger therapeutic array. Rosenschein [21] describes a 94 mm diameter therapeutic array into which a 7.5 MHz annular array is placed in concentric fashion. The system was used successfully for in vitro thrombolysis in bovine artery segments. Unger [22] describes (at least conceptually) a transducer design incorporating therapeutic and imaging array elements with a common front face plane. In this example, the therapeutic array is placed within a hole in the imaging array. A large central "hole" in an array aperture gives rise to a near-field blind spot and distorted sidelobe patterns—typically grating lobe related due to the poor spatial sampling implicit by virtue of the "hole" in the aperture. Until now, much work has involved fixturing an imaging array with respect to a therapeutic focused transducer/array [23-25]. An integrated imaging and therapeutic array, for example, was described by the University of Washington [26]. There is, however, no reason to believe that such an "integrated" array comprises exactly coincident "therapeutic" and imaging arrays as proposed here. The precise need for defining a required level of "integration" is a function of the particular application.

In the context of microbubble imaging, Bouakaz [27] has described a dual frequency transducer (0.9 MHz and 2.8 MHz) array using interspersed elements. The element spacing is 0.5 mm—i.e. λ spacing at 2.8 MHz. When using an interspersed element design it becomes doubly problematic to achieve adequate spatial sampling. Further, only <50% of potential active area for each array (in isolation) is available. This loss of active area limits maximal acoustic power delivery. Forsberg [28] has also described a multifrequency array in which three linear arrays (2.5 MHz, 5 MHz and 10 MHz) were placed side-by-side with a common focal range (50 mm) This approach works well within the one fixed focal region but lacks the versatility to address other ranges.

In an aspect of an embodiment of the present invention, there may be provided the imaging array immediately over the therapeutic array. Some advantages of an embodiment of the present invention configuration may be illustrated in FIG. 3. FIGS. 3(A)-(C) schematically illustrate the arrays of the Forsberg array (see FIG. 3(A)) having elevational view—field intersection at one pre-selected range; Bouakaz array (see FIG. 3(B)) with alternating elements of high and low frequency and having poor sampling and 50% area use per array; and an exemplary present invention embodiment of the stacked arrays (see FIG. 3(C)) having fine sampling and 100% area usage. The transducer operating frequency may be inversely related to device thickness. The High and Low frequency transducer components are denoted: HF and LF, respectively. All three transducers may be implemented with various embodiments of the present invention as desired or required.

Figure 4:
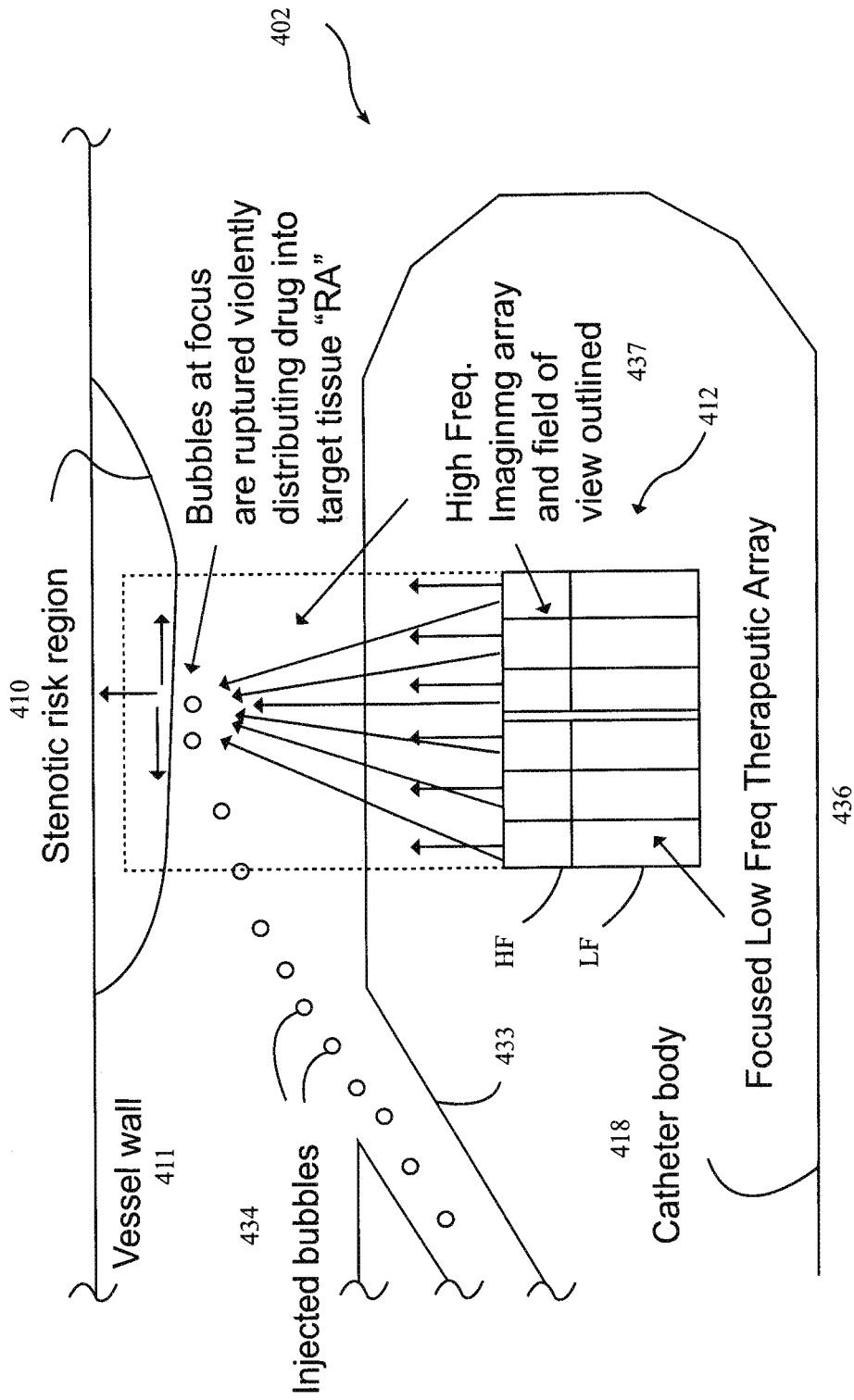
FIG. 4 schematically illustrate an embodiments (or partial embodiment) of the present invention ultrasound catheter system.

FIG. 4 schematically illustrates an embodiment (or partial embodiment) of the present invention ultrasound catheter system 402 for providing therapy (as well as diagnostic if desired or required) to a treatment site at one or more locations of a subject. The catheter system 402 may comprise a tubular member such as a catheter body 418 such or multiple catheters, needles, or lumens. The catheter(s) having a proximal region and distal region, whereby the proximal end of the ultrasound catheter is adapted or configured to be advanced to or in proximity to the subject's treatment site such as a stenotic risk region 410. It should be appreciated that any one of the catheters 418 as shown may be a plurality of catheters and any given catheter may have one or more lumens therein. The system further comprises a microbubble reservoir, port or channel 433 in hydraulic communication with the tubular member 418 and any lumens, channels, controllers or communication devices related to the catheter system. The microbubble reservoir, port or channel 433 is adapted to release microbubbles that are intended to be located into or proximal to the treatment site 410 at the desired or applicable location, such as a vessel or vessel wall 411 of the subject. The system 402 further comprises an ultrasonic energy source 412 in communication with the distal region (or other region as desired or required) of the tubular member 418 (as well as other components or subsystems of the present invention). The ultrasonic energy is adapted for, or capable of: imaging the treatment site 410, (some embodiments, for example, optionally pushing bubbles using ultrasound radiation force [29]), and rupturing the microbubbles. For instance, therapeutic array 436 for bursting the microbubbles are provided (e.g., at low frequency LF or as desired or required). Further, an imaging array 437 for imaging (e.g., at high frequency array HF or as desired or required).

Still referring to FIG. 4, the system 402 further comprises (although not shown) a control circuitry configured to send electrical activation to the ultrasonic energy source, as well as other components and subsystems of the present invention. Further, the ultrasonic energy source may provide ultrasonic radiation forces for translating the microbubbles 434 into or in the vicinity of the treatment site 410 at the desired or applicable location 411 of the subject; or alternatively the mechanical forces may be provided for translating the microbubbles into or in the vicinity of the treatment site 410, as well as a combination of both mechanical and ultrasonic forces (acoustic wave) to achieve the desired or required result.

It should be appreciated that the aforementioned catheter 418, microbubble reservoir or channel 433, ultrasound source(s) 412, and controller may be disposed entirely inside the applicable location of the subject, outside the location of the subject or a combination of inside or outside the location of the subject. The one or more locations 411 of the subject may be an organ. The organ may include hollow organs, solid organs, parenchymal tissue, stromal tissue, and/or ducts. The one or more locations 411 of the subject may be a tubular anatomical structure. The tubular anatomical structure may be a blood vessel. Further, for example, the treatment site 410 may be a vasculature treatment site comprising at least one of the following: stenotic region or any region exhibiting vascular disease. Further, for example, the treatment site 410 may be a vasculature treatment site and/or a diagnostic site.

As such, the approach illustrated in FIG. 4, provides, for instance, a catheter for delivery of drug loaded bubbles, ultrasound imaging of bubbles/tissue, and ultrasound-based bubble destruction/drug delivery.

The imaging transducer/transducer array and the therapeutic transducer/transducer array may be identical. Whereas it is sometimes necessary to optimize two transducers for two functions it is also feasible, if the transducer possesses sufficient performance versatility (e.g. high frequency bandwidth and high power capability) to use the same transducer for both imaging and therapeutic function. Ultrasound-triggered Release of Rapamycin from Microbubbles Attenuates SMC Proliferation Over 48 Hrs. In Vitro.

As discussed above, the chemical and biological properties of rapamycin and why it is the benchmark reagent for preventing SMC proliferation associated with vascular injury in vivo. This established the rationale for choosing rapamycin for ultrasound-triggered microbubble carrier release. Multiple groups have shown that treatment of cultured SMCs with rapamycin reduces SMC proliferation [12, 30]. However, delivering of rapamycin via ultrasound triggered release from a microbubble carrier has not been performed.

Exemplary Design/Experiment

Ultrasound was applied to rat smooth muscle cells in conjunction with modified ultrasound microbubbles containing rapamycin in their shells. The microbubbles were prepared by co-inventor A. L. Klibanov at University of Virginia. Of course, the present invention is not so limited, as microbubbles described herein can be prepared by other manufacturers. Microbubbles were formed by self-assembly of a lipid monolayer during the ultrasonic dispersion of decafluorobutane gas in an aqueous micellar mixture of phosphatidylcholine (2 mg/ml) and Polyethylene Glycol (PEG) stearate (2 mg/ml) with rapamycin (0.2 mg/ml) and/or a trace amount of a fluorescent dye DiI (Molecular Probes, Eugene, Oreg.), similarly to the procedure described previously [78]. Fluorescently labeled DiI microbubbles were used as a control to ensure that the microbubble vehicle alone did not cause an effect on the cells. The rapamycin drug, dissolved in 100% ethanol, was also used as a control with which to compare the effect of the rapamycin microbubbles. We assured a strong adherence of cells to the OPTICELL™ (Biocrystal, Westerville, Ohio) flasks by plating them with fibronectin for 24 hrs. prior to plating any cells. Rat SMCs were plated at a low density and allowed to grow for 48 hrs. in DF10 media inside each of 12 OPTICELLs™. Digital phase microscopy light images of the cells were taken at 5 hours prior before treatment to establish baseline conditions. All images were taken at 4× magnification. 24 hrs. after plating, the media was replaced with fresh media containing either the DiI microbubbles (vehicle control), rapamycin drug (drug control), or rapamycin microbubbles. The microbubbles (DiI or rapamycin) were added to the OPTICELLs™ at a concentration of $10 \times 10^6$ bubbles/ml and the rapamycin was added at a concentration of 10 ng/ml. The microbubble concentrations were chosen such that the number of microbubbles added contained an equivalent amount of rapamycin, ~10 ng/ml. We ensured that the drug had an effect even without prolonged exposure by taking half of the OPTICELL™ flasks and giving them treatment for only two hours. After two hours the drug/bubble-containing media was replaced with fresh media. The cells in the OPTICELL™ flasks received one of the following 6 treatments: DiI bubbles for 48 hours, rapamycin drug for 48 hours, rapamycin bubbles for 48 hours, DiI bubbles for 2 hours, rapamycin drug for 2 hours, rapamycin bubbles for 2 hours. All conditions were tested in duplicate.

Following the placement of fresh media and microbubbles into each OPTICELL™, ultrasound was applied to the entire area of cell growth. One at a time, each OPTICELL™ was horizontally placed into a water bath (~37° C.). A focused 1 MHz (Panametrics, Waltham, Mass.) transducer was immersed in the water and located directly above the cells. A motion controller was used to traverse the transducer across the aperture of the OPTICELL™ so as to evenly apply ultrasound to the entire area of cell growth. A 1 MHz, 35% BW, Gaussian pulse was applied at a Pulse Repetition Frequency (PRF) of 1 kHz, 600 kPa peak, for the entire insonation time (9 mins.). Images were taken at 4 locations within each OPTICELL™. These locations were marked with a dot at the 5 hour time point. Subsequent images were taken at these same locations, 24 hours, and 48 hours after treatment. The OPTICELLs™ were stored in a 37° C. incubator.

Figures 5A, 5B, 5C:
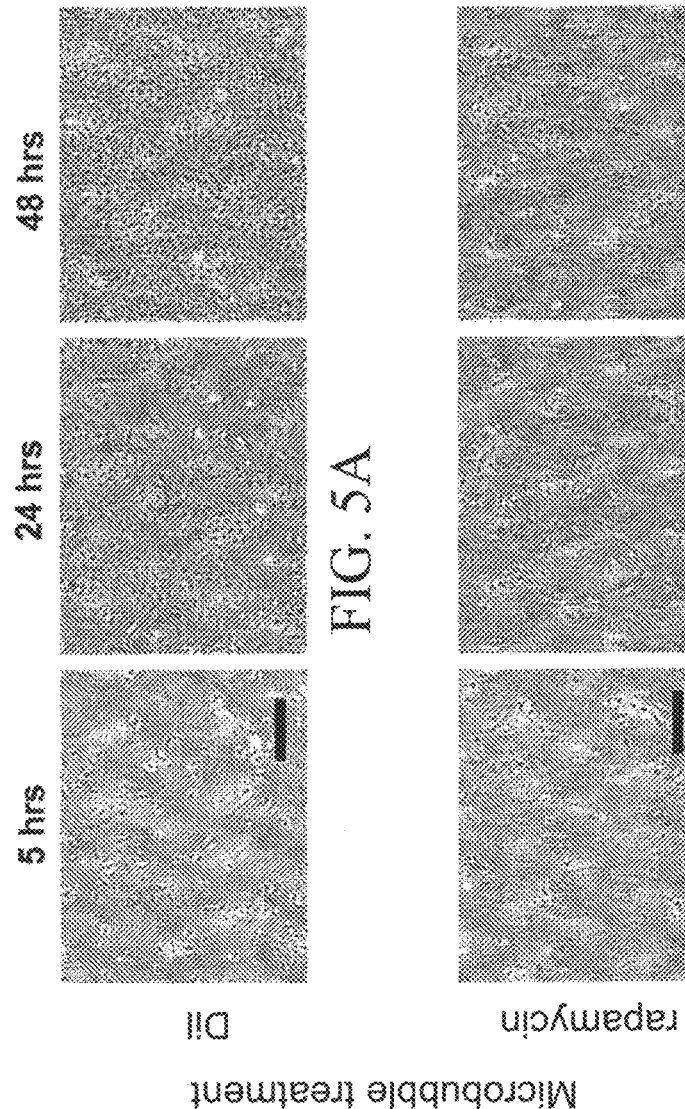
FIG. 5: illustrates the epifluorescence microscopy observations (FIGS. 5 A, B, C) and ultrasound backscatter imaging (FIGS. 5D, E) of adherent microbubbles. Microcapillaries infused with buffer alone show no microbubble adhesion (A) and no ultrasound signal (dashed box illustrates microcapillary location) (D). Few adherent microbubbles are visible in flow-only microcapillaries (B), and the corresponding echo is identifiable but weak. A large number of adherent microbubbles are present in a microcapillary exposed to radiation force at 122 kPa (C), and the corresponding echo is strong. Scale bar represents 5 μm.
Figure 5E:
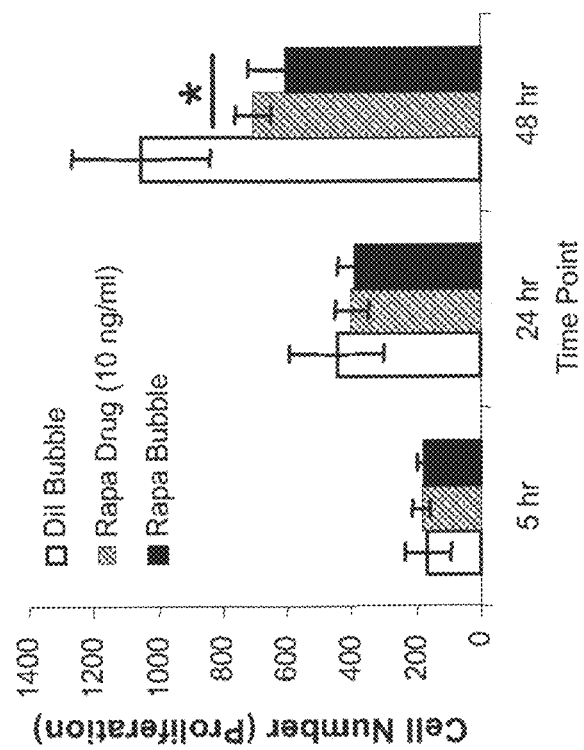
Figure 5D:
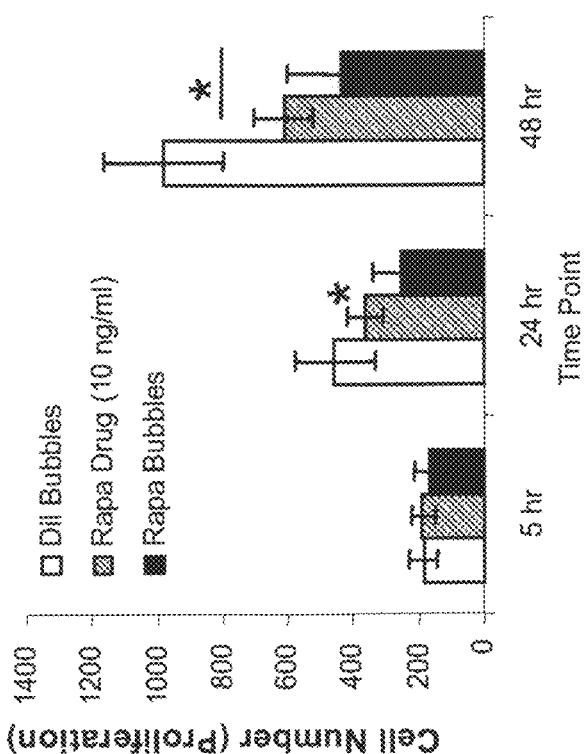

Results:

In FIGS. 5(A) and 5(B), we show that delivery of ~10 ng/ml of rapamycin by ultrasound-triggered release form a microbubble carrier prevented SMC proliferation, depicted as a change in cell number, compared to release of a fluorescent membrane dye, DiI (Invitrogen), from an equivalent number of microbubble carriers. Moreover, quantitative analysis in FIG. 5(D), shows that delivery of rapamycin (10 ng/ml) by ultrasound-triggered release from a microbubble carrier was not different from cells treated with free rapamycin drug (10 ng/ml) in the cell culture media. Similar results were observed in the set of 6 OPTICELLs™ which were only treated for 2 hours post ultrasound and then allowed to grow for 48 hours (FIGS. 5(C) and 5(E)). Thus, these results show (among other things) that rapamycin and an inert cell marking dye (DiI, FIG. 5(C)) can be delivered to SMCs by ultrasound-triggered microbubble carrier release.

Figure 6:
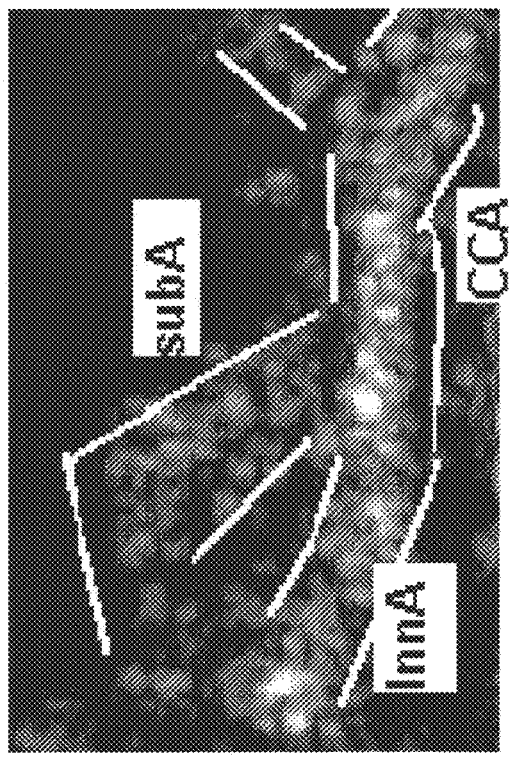
FIG. 6 illustrates a 10 MHz (e.g., Sequoia CPS) image of mouse common carotid using microbubbles with dual targeting: polymeric sialyl LewisX (psLex) and anti-mouse VCAM-1. Cho et al. "Dual-Targeted Contrast" AHA Abstract 2006. See Weller G E, Villanueva F S, Tom E M, Wagner W R. Targeted ultrasound contrast agents: in vitro assessment of endothelial dysfunction and multi-targeting to Inter-Cellular Adhesion Molecule 1 (ICAM-1) and sialyl Lewisx. Biotechnol Bioeng. 2005 Dec. 20; 92(6):780-8, of which are hereby incorporated by reference herein.
Figure 7A:
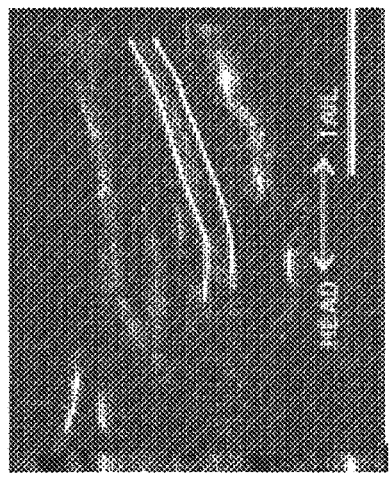
FIG. 7 illustrates: at FIG. 7(A) a B-Mode ultrasound image of a rat carotid (using 40 MHz transducer, on VisualSonics Vevo 770, available from VisualSonics, Toronto, Canada). Yellow arrows point to the blood vessel; at FIG. 7(B) a B-mode of a rat carotid artery (12 MHz); and at FIG. 7(C) 10 MHz ultrasound imaging using bubble sensitive/specific imaging mode. White tracing denotes the carotid artery wall. White Scale bars=10 mm.
Figure 7B:
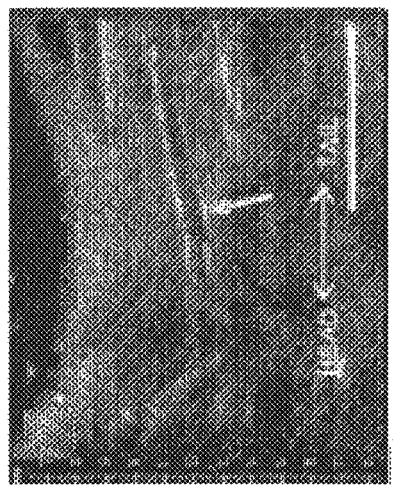
Figure 7C:
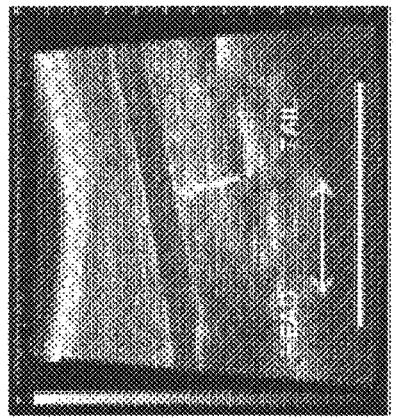

Next, non-invasive ultrasound imaging can play a critical role in the guidance of the therapeutic ultrasound that will localize the release and transcellular membrane delivery of the rapamycin drug. For instance, FIGS. 6 and 7 illustrate the current capabilities for fine-scale visualization of rodent vasculature. FIG. 6 illustrates a bubble-specific image of vessel wall-bound molecular-targeted (anti-VCAM-1) bubbles in the mouse common carotid artery (CCA) assessed using 10 MHz bubble specific ultrasound imaging (e.g., Sequoia scanner or other commercial clinical ultrasound scanner). FIG. 7(A) is a VisualSonics VEVO 770 image of a rat carotid at 40 MHz demonstrating fine spatial resolution. FIGS. 7(B) and 7(C) are B-Mode, and contrast specific, rat carotid images acquired at 12 MHz and 10 MHz, respectively (e.g., Sequoia scanner).

Transducer and Instrumentation

An exemplary transducer solution for dual function imaging therapeutics is one in which the transducer elements are sufficiently versatile that they can accomplish both tasks—high frequency (HF) imaging and low frequency (LF) bubble manipulation/breaking. This enables a design in which the imaging plane and therapeutic planes are coincident. Deficiencies in these previous designs suggest the need for a superior solution.

The solution to the dual function requirement of the transducer (HF, high resolution, low intensity imaging and LF, high power bubble fracture) is to form a transducer with two active layers: one on top of the other (for example as shown in FIG. 3(C) or FIG. 4). Each layer is resonant at a widely disparate frequency—the lower one at about 1-2 MHz and the upper one at approximately 12 MHz. Conventional design wisdom relating to stacked transducer layers would suggest that the two transducer layers would cause high undesirable interference between the resonances associated with each of the layers. Nevertheless, our experience suggests that a two layer transducer will work provided that the transducer layers are well matched between each other and to the backing material.

Figure 8A:
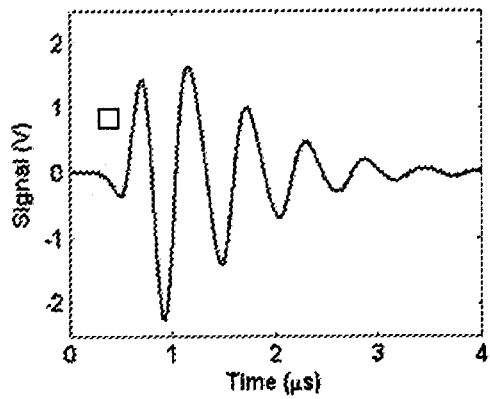
FIG. 8 illustrates prototype pulse echo responses of dual layer (multifrequency) transducer.
Figure 8B:
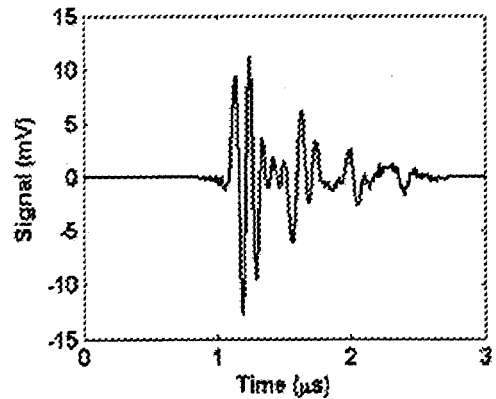
Figure 8C:
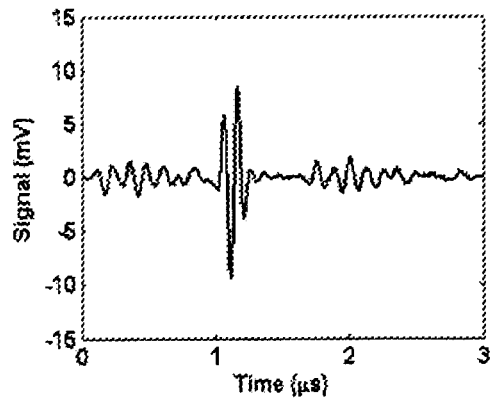
Figure 8D:
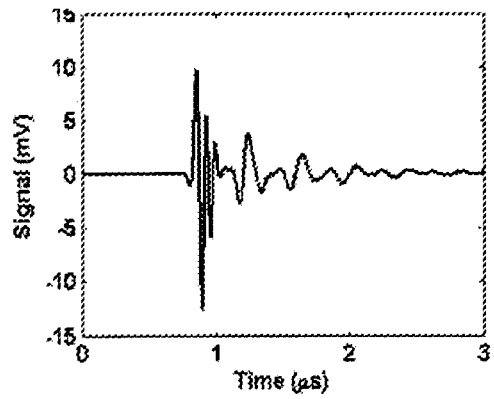

In an approach, a prototype dual layer single element transducer was designed using 1:3 PZT/epoxy composite transducer layers. The acoustic impedance of each layer is approximately 15 MRayl. The backing is a dense metal (tungsten) loaded epoxy with an acoustic impedance of approximately 9 MRayl. This transducer was fabricated to our design by Vermon, Tours, France. The single element device, 1 cm in diameter and with a focal depth of 5 cm, was constructed to test the viability of the proposed dual layer approach. FIG. 8(A) illustrates the pulse-echo responses of the LF layer. The LF result exhibits a desired smooth, short duration, waveform. The high frequency layer in the current prototype exhibits a reflection artifact that we attribute to reflections between the rear of the low frequency layer and the backing block (FIG. 8(B)). In FIG. 8(C), we show that we can substantially correct this deficiency by using an inverse filter designed to force the response to be more Gaussian (in the frequency domain). Alternatively, we will redesign and optimize the dual layer transducer using better matched transducer layers to minimize/eliminate internal reflections. An early FEA result for a modified design, using a better matched backing (i.e. 15 MRayl), is shown in FIG. 8(D).

The transducer may be designed for any one of many clinical applications. It may be for transcutaneous use and comprise a conventional phased or linear array (flat or curved, or contoured anatomically or ergonomically as desired or required). It may also be designed for transesophageal, transvaginal, transurethral, transrectal or intraoperative use. Examples of each of these form factor transducers are known in the field—usually comprising similar transducer structures inside a plastic case adapted to the chosen anatomic use.

The transducer may also be formed in a catheter—as in intravascular ultrasound (IVUS). IVUS catheters are currently widely marketed in the US by Boston Scientific (Natick, Mass.) and Volcano (Rancho Cordova, Calif.). The Boston Scientific transducer typically comprises a single element that is rotated at high speed by a drive wire to form a coronal view. The transducer element in this transducer may be modified by changing its operating frequency (i.e. lowered to around 2-15 MHz) to make it suitable for breaking bubbles. The Volcano transducer is generally a circumferential phased array. Again, the frequency of the array design may be modified (i.e. lowered to around 2-around 15 MHz) to make it suitable for breaking bubbles. It is possible to potentially use either a dual layer design—as described herein—or potentially use a modified design where a compromise between high frequency imaging and low frequency bubble breaking is selected—e.g., instead of attempting to operate imaging at about 25 MHz and breaking at about 2 MHz, a single wideband design at about 15 MHz is capable of about 8 MHz breaking and 20 MHz imaging. High bandwidth transducer design may be employed, such as by using multiple matching layers, for example, as known to those skilled in the art. As shown in FIGS. 4 and 12, for example, the catheter transducer may also include a continuous hollow port down which drug coated contrast is flushed during use. In this way, a stream of active contrast is emitted into the field of view of the transducer as shown schematically. (In clinical use, the blood flow in the coronaries is in the "right" direction—i.e. blood flow is moving in the distal orientation.)

Notice also that other formats of drug media delivery are possible. For example: free dissolved (e.g., in water, alcohol or other compatible solvent) rapamycin (or other drug) may be transferred side by side with plain contrast microbubbles down the hollow port. As indicated in Price's 1998 Circulation paper ("Delivery of colloidal particles and red blood cells to tissue through microvessel ruptures created by targeted microbubble destruction with ultrasound" Vol. 98, No 13, pp 1264-1267), local bubble breakage enables delivery of colloidal material (including potential drug in dissolved or undissolved form) across microcirculatory vessel walls. Bubbles could be injected intravenously and dissolved rapamycin may be injected via the catheter port.

Normally lipid based bubbles are used. Other shell materials may be used—such as albumen-based or polymer-based shelled bubbles. Bubbles with these shell materials are known in the field.

Instrumentation

Among various options available, the SonixRP (Ultrasonix, Richmond, BC, Canada) is a versatile platform to use as the base instrumentation for implementing the invention. Of course, other scanner platforms may be procured or designed/built as is well known to those in the field. The RP, and its research capabilities (including high level software/hardware architecture), are described in detail in a recent publication [79].

It should be appreciated a number of marketed technology systems and components may be implemented with the present invention such as by, but not limited to, the following: the medical ultrasound companies include: Philips, Siemens, and General Electric—also VisualSonics etc. However, it may be noted that these are not catheter based companies. Boston Scientific and Volcano are the primary IVUS companies.

In Vitro Radiation Force Enhanced Molecular Targeted Ultrasound

A problem encountered when using intravascular injected targeted contrast agent is that, except in very small vessels, only a very small fraction of the injected material will be sufficiently close (<1 µm) to have even a remote chance to form the intended molecular bond between ligand and receptor. In vitro studies of targeted microbubble adhesion on substrates of P-selectin have reported that only a small percentage of the perfused microbubbles were specifically retained under physiological flow conditions [e.g., Klibanov [80]. Although detection of single microbubbles is possible [81], low efficiency of microbubble targeting requires a larger administered dose of microbubbles than would otherwise be required. Microbubbles exhibit rheological behavior similar to that of erythrocytes [82] and tend to migrate towards the center of the blood vessel. As most endothelial proteins extend only nanometers [83] from the endothelium, it is unlikely that many of the microbubbles flowing through the targeted vasculature come into contact with the intended molecular target. Microbubble attachment efficiency can be increased by moving circulating microbubbles into contact with the vessel wall, thus increasing the frequency of microbubble: target adhesive events. Dayton [84] and others [85] previously hypothesized that microbubble adhesion to the vascular endothelium may be enhanced by using ultrasound radiation forces to propel freely flowing microbubbles towards the vessel wall. Adhesion of microbubbles [86] and acoustically active liposomes [87] under applied acoustic pressure in an avidin: biotin model system has been examined, and adhesion of targeted microbubbles to cultured endothelial cells has been reported [86].

Acoustic radiation traveling through a continuous media produces a pressure gradient, which is experienced as a directional force by compressible bubbles in the acoustic field. Two components of this radiation force have been described: a primary force, which is directed away from the source, and a secondary force, which is typically attractive between ultrasound contrast microbubbles [88]. The behavior of single, free-stream microbubbles exposed to acoustic radiation has previously been examined rigorously [84, 88, 89]. Derivations of the magnitude of both primary and secondary forces in the linear range were presented by Dayton [84], assuming a low duty factor, a constant magnitude of pressure in each applied pulse, and a unidirectional pressure gradient. The primary radiation force is proportional to the negative time-averaged product of the microbubble volume and the spatial pressure gradient. For a microbubble driven at resonant frequency, assuming small-amplitude oscillations, the magnitude of the primary radiation force is defined by $$F_1 = \frac{2\pi P_a^2 R}{\delta \omega_0 \rho c} \left[\frac{D}{T}\right]_{(1)}$$

where $P_a$ is the peak applied acoustic pressure, R is the microbubble resting radius, $\delta$ is the total damping coefficient, p is the medium density, c is the velocity of sound in the bulk aqueous phase, and $\omega_0$ is the microbubble resonant frequency. This term is scaled by D/T for a pulsed field, where D is the pulse duration and 1/T is the pulse repetition frequency (PRF).

Figure 9:
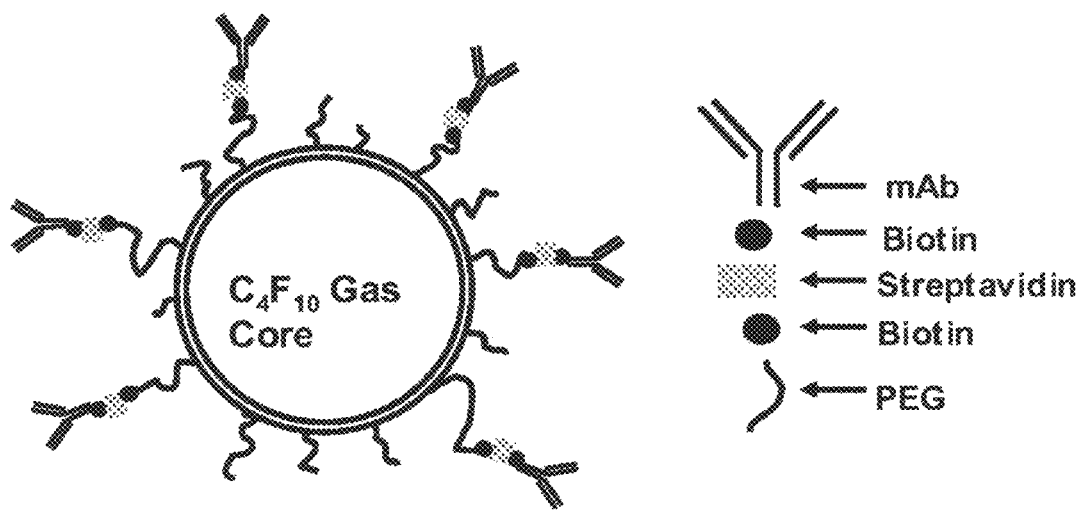
FIG. 9 illustrates a diagram of targeted ultrasound contrast microbubble. The gas core is encapsulated by a lipid monolayer shell, which is coated with a PEG brush. The targeting ligand, here an anti-P-selectin monoclonal antibody, is secured to the distal tips of the polymers via a biotin-streptavidin link. This figure is not to scale.
Figure 10:
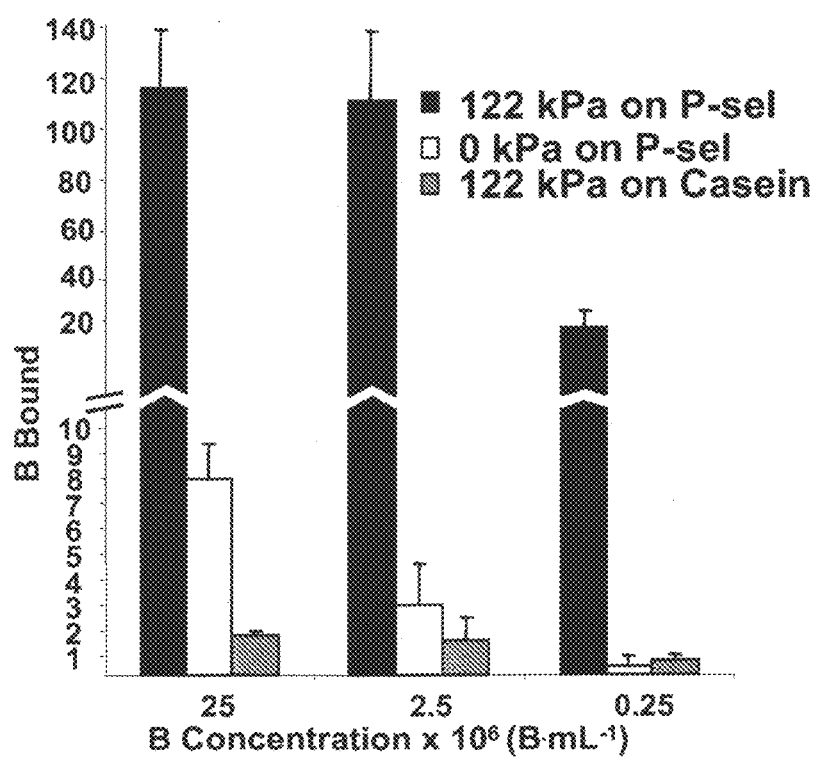
FIG. 10 illustrates a microbubble adhesion at wall shear rate of 355 s-1 on P-selectin after insonation at 122 kPa (122 kPa on P-sel; n=4), adhesion on P-selectin after flow alone (0 kPa on P-sel; n=3), and adhesion on casein after insonation at 122 kPa (122 kPa on Casein—i.e. control); n=3). Mean number of adherent microbubbles per 10 optical fields+standard deviation. Insonated capillaries exhibited significantly greater adhesion (p<0.05) than that of the flow only or insonated capillaries at each condition examined. The break in vertical scale may be noted.

Targeting these microbubbles to P-selectin was achieved by conjugating the anti-P-selectin monoclonal antibody (mAb) Rb.40.34 [90] to the distal tips of PEG chains via a streptavidin link, as shown in FIG. 9. The preparation of the targeted microbubbles used in this experiment has been described in depth elsewhere [78, 91]. Trace amount (<1% of total lipid mass) of DiI lipid dye (Molecular Probes, Eugene, Oreg.) was used as a fluorescence probe for epi-illumination microscopy. Microbubbles were conjugated to the targeting ligand the day of the experiment, and were stored on ice in $C_4F_{10}$-saturated Dulbecco's Phosphate Buffered Saline Solution (DPBS) (Invitrogen, Carlsbad, Calif.). Microbubble size distribution and concentration was determined with a Coulter counter (Beckman-Coulter, Miami, Fla.).

A 2.25 MHz, 0.5" diameter, 0.8" focal depth ultrasound transducer (Panametrics V306, Waltham, Mass.) was used in this study. At a Pulse Repetition Frequency (PRF) of 10 kHz, 40 sinusoidal cycles at a frequency of 2.0 MHz were applied. Microbubbles were insonated at acoustic pressures between 24.5 and 170 kPa. Upon cessation of insonation, 10 optical fields along a P-selectin coated microcapillary within the width of the applied ultrasound beam were observed and recorded. Alternatively, some flow chambers were exposed to 2 minutes of flow alone, without insonation, in order to assess microbubble binding in the absence of applied radiation force. The number of adherent microbubbles in each of 10 fields of view following insonation was determined off-line. Microbubbles aggregates projecting normal to the optical plane (downward into the flow stream) were counted as a single bubble. Microbubble aggregation was assessed by counting the number of contiguous microbubbles adherent in the optical plane. Each flow chamber was used for a single experiment. Statistical significance was tested with a Student's t-test. We observed negligible binding of targeted microbubbles to casein-coated (i.e. control) microcapillaries both with and without the application of radiation force. We observed a statistically significant ($p<0.05$) increase in specific microbubble adhesion to P-selectin due to applied radiation forces at each of the microbubble concentrations examined Applied radiation force increased targeted microbubble adhesion to P-selectin coated microcapillaries 16-fold at $75 \times 10^6$ B $ml^{-1}$ and over 60-fold at $0.25 \times 10^6$ B $ml^{-1}$ (or other sizes, volumes and ranges as required or desired).

Imaging of adherent microbubbles in flow chambers was also performed using 14 MHz ultrasound imaging (e.g., on a Siemens Sequoia or similar clinical scanner). Microbubbles were infused into the flow chamber as described above and exposed to 1 minute of flow alone at the indicated shear rate, followed by one minute of insonation at 122 kPa or 1 additional minute of flow only. It has also been determined that microbubbles attached to the target substrate by acoustic radiation force remain viable for ultrasound imaging. We observed no adherent microbubbles and received no ultrasound signal in microcapillaries infused with buffer alone (FIG. H(A), FIG. H(D)). A contrast signal is visible in FIG. 11(E), which shows an ultrasound image of a microcapillary infused with $2.5 \times 10^6$ B/ml for 2 minutes in the absence of acoustic pressure then flushed with buffer. A representative fluorescence microscopy field of view in this capillary is presented in FIG. 11(C), FIG. H(B). FIG. H(C) shows a representative optical field of view from a microcapillary infused with $2.5 \times 10^6$ bubbles/ml exposed to 1 minute of flow only, 1 minute of insonation at 122 kPa and then saline flushed, in which extensive microbubble accumulation is evident. The corresponding echo shown in FIG.H(F) is very strong. This suggests that the microbubbles targeted by means of radiation force at an acoustic pressure of 122 kPa remain intact and echogenic.

In summary, we have demonstrated some of the key components of some of the embodiments of the present invention method and system including, but not limited thereto, the following:

1. Rapamycin loaded microbubbles+ultrasound have a demonstrated, selective, anti-proliferative effect on rat SMCs.
2. VCAM-1, as well as other cell surface antigens including but not limited to PECAM, is upregulated in proliferating SMCs in the rat and other animal models of stenosis and human restenosis.
3. Fine resolution ultrasound imaging can visualize vasculature anatomy and achieve high sensitivity/high specificity bubble imaging.
4. Dual frequency transducers for: a) high frequency imaging, and b) low frequency radiation force/bubble fracture.
5. Radiation force can be used to improve bubble molecular VCAM-1 targeting attachment efficiency.

Related Exemplary Methods (and Related Systems)

Single Element Transducer (Typically Non Imaging Capable).

Our preliminary data provided promising early results using a simple, axisymmetrically focused, single element transducer. What is required is a dual function (low frequency bubble "busting" plus high frequency imaging) transducer and associated instrumentation.

Transducer Array (Typically Imaging Capable).

An exemplary design may comprise 1:3 composite piezoceramic-epoxy active layers stacked one over the other. (A "1:3" composite comprises piezoelectric ceramic posts embedded in a polymer matrix—i.e. the two components are electrically and mechanically in "parallel". The 1:3 configuration is the dominant composite configuration and is in widespread commercial use.) The composite material possesses approximate 50% ceramic volume fraction and possesses an acoustic impedance of approximately 15 MRayl. A dense, tungsten particle filled, backing block is used. A thin matching layer, approximately quarter wavelength matched for 12 MHz operation, is used over the top. A conventional filled silicone rubber lens will be used to obtain an elevation focus. The elevational focal depth is approximately 15 mm Specifically, we use approximately 12 MHz B-Mode imaging resulting in <200 µm lateral resolution and axial resolution. At this frequency, λ is 125 µm. Consequently, for practical f#s, (i.e. 1-2) a 200 µm resolution is feasible. An array system provides more than sufficient scanning frame rate (>100 frames/s for selected small fields of view—e.g. 15 mm×15 mm) Focused ultrasound delivery is delivered at 1-2 MHz. We are able to control the region over which a therapeutic effect is obtained to approximately 3λ—i.e. approximately a 2 mm spot size.

High Resolution, High Sensitivity, High Specificity, Bubble Imaging.

An objective is to provide anatomic B-Mode imaging capability, bubble specific imaging and application of bubble fracture pulses under user control. The anatomic B-Mode imaging are accomplished using standard B-Mode image formation techniques—i.e. optimized aperture apodization, fixed focus transmit, dynamic receive focusing, signal detection and scan conversion. Bubble specific imaging will be provided by using "Pulse Inversion" (PI) [92]—i.e. 1, −1 transmit polarity/amplitude; followed by "1"+"−1" processing to eliminate the linear component). If necessary other bubble specific techniques such as amplitude scaling (i.e. 1, 2 transmit polarity/amplitude; followed by (2ב1")−"2" processing [93]) and the combination of PI and amplitude scaling (e.g. −1, 2, −1 transmit polarity/amplitude; followed by "−1"+"2"+"−1" processing [47]).

Low Frequency, Bubble Pushing and Bubble Destruction.

These modes use the low frequency elements of the array. The design of an embodiment for the transducer comprises less than a total of 128 elements (96, 12 MHz elements and 24, 2 MHz elements). In this way, by simply reprogramming the selected transducer apertures from the available 128 transducer connector channels, we can switch between imaging and therapeutic modes of operation.

Design Rapamycin Microbubble Carrier System Capable of Ultrasound-triggered Release Bubble Making and Rapamycin Incorporation.

Microbubbles are prepared by self-assembly of a lipid monolayer during the ultrasonic dispersion of decafluorobutane gas in the aqueous micellar mixture of phosphatidylcholine and PEG stearate (2 mg/ml) with rapamycin (0.2 mg/ml) and/or a trace amount of a fluorescent dye DiI (Molecular Probes, Eugene, Oreg.), similarly to the procedure described earlier [95]. In some instances, membrane thickening is achieved by addition of glycerol trioleate (thicker microbubble shell will harbor increased amounts of rapamycin) [96]. Free lipid, dye and rapamycin, not incorporated in the bubble shell is removed by sequential (3×) centrifugal flotation (100×g, 5 min), with the recycling of the first wash to save reagents.

Rapamycin Quantitation.

Robust and sensitive high performance liquid chromatography (HPLC) procedures are described in the literature for clinical assays. We have HPLC available in our laboratory and will implement such a procedure [97]. Briefly, the sample being tested (microbubbles or media) is lyophilized and redissolved in chlorobutanol, centrifuged to remove sediment; samples placed in the autosampler vials and HPLC performed with UV detection against a calibration curve with a known amount of rapamycin.

Rapamycin Release by Ultrasound: In Vitro Functional Bubble Destruction Testing.

An aqueous saline dispersion of rapamycin-containing microbubbles ($10^6$-$10^7$/ml particle concentration) will be placed in an OPTICELL™ (USA Scientific, Ocala, Fla.) in 10 ml volume. We will destroy bubbles by ultrasound in the conditions described for the cell culture study, remove the microbubble particles from OPTICELL™ and subject them to centrifugal flotation to prove that residual microbubbles (if present) will be removed from the samples. We will then perform rapamycin quantitation in the bubble-free infranatant by HPLC technique as described above.

Attachment of Anti-VCAM-1 Antibody to Microbubbles.

Coupling of anti-VCAM-1 antibody to microbubble surface is performed by streptavidin coupling technique as described [91]. Briefly, during the preparation of microbubbles, 2 mol % of biotin-PEG3400-phosphatidylethanolamine is added to the lipid mixture. A streptavidin bridge technique is applied for biotinylated anti-VCAM-1 antibody coupling to the microbubble surface as described earlier for other antibodies [80, 98]. Biotinylation of antibody molecule is performed with biotin N-hydroxysuccinimide ester reagent at pH 7.5 in DPBS buffer. The degree of antibody biotinylation is tested using the HABA assay as described previously [e.g., Klibanov [80]]. By the adjustment of the antibody-to-biotin-NHS, an incubation ratio coupling of ~1 biotin per antibody will be achieved. The ELISA test on VCAM-1 antigen is used to confirm that biotinylation does not inactivate the antibody. Streptavidin-bubbles ($10^9$/ml) are incubated with biotinylated antibody on ice for 30 min; free antibody molecules are removed from the bubbles by triple centrifugal flotation wash with degassed DPBS buffer in a bucket-rotor centrifuge (100×g, 5 min) After repeated flotations, the mean size of antibody-coated bubbles is normally ~2.5 µm, with >99% of the particles less than 8 µm (particle size and concentration are evaluated with a Coulter Multisizer He instrument (Beckman Coulter, Miami, Fla.). The amount of attached antibody per bubble is tested by fluorescence spectroscopy labeling as described earlier; typically, ~$10^5$ antibody molecules per microbubble are attached by this technique [98].

Figure 12A:
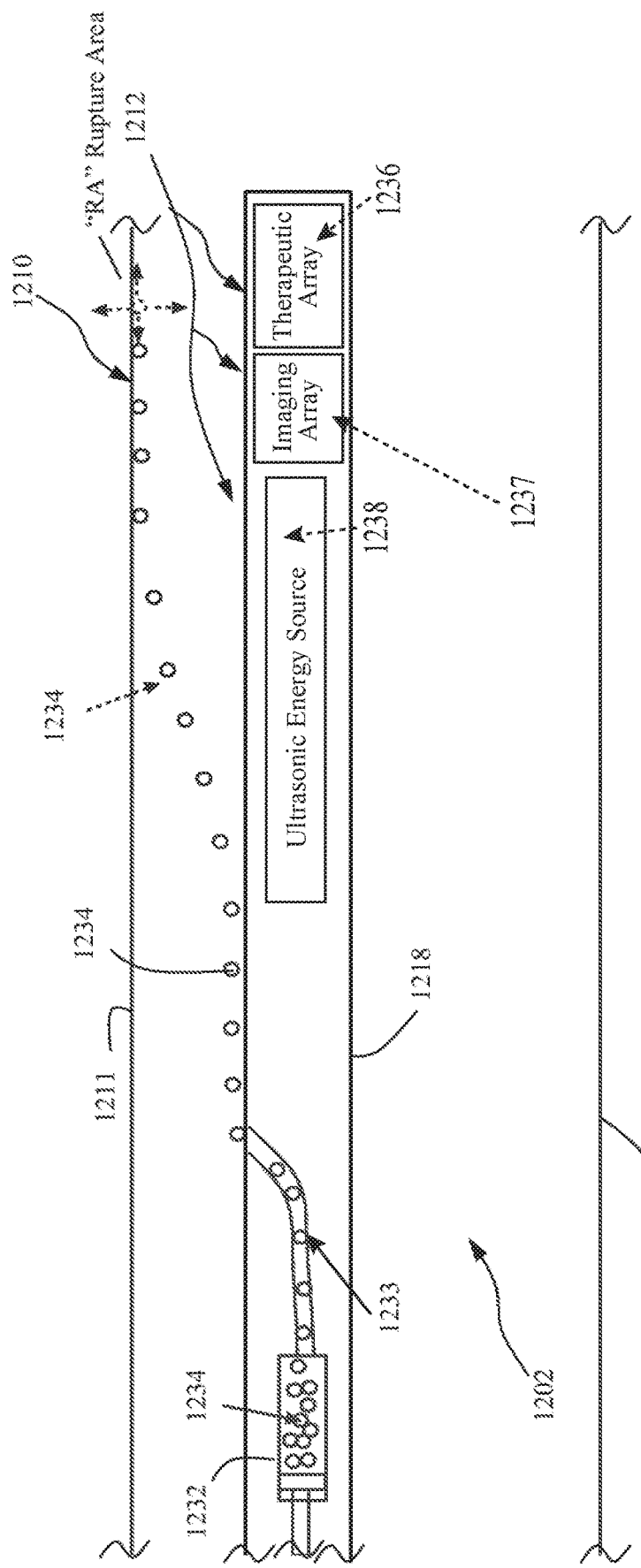
FIGS. 12(A)-(B) schematically illustrate various embodiment (or partial embodiment thereof) of the present invention ultrasound catheter system.

FIG. 12(A) schematically illustrates an embodiment (or partial embodiment) of the present invention ultrasound catheter system 1202 for providing therapy (as well as diagnostic if desired or required) to a treatment site at one or more locations of a subject. The catheter system 1202 may comprise a tubular member 1218 or other conduit or chamber, such as multiple catheters, needles, or lumens. The catheter(s) having a proximal region and distal region, whereby the distal end portion of the ultrasound catheter is adapted or configured to be advanced to or in proximity to the subject's treatment site or region 1210. It should be appreciated that any one of the tubular member 1218 as shown may be a plurality of tubular or conduit members and any given catheter or the like may have one or more lumens therein. The system further comprises a microbubble reservoir 1232 in hydraulic communication with the port or channel 1233 and in hydraulic communication with the tubular member 1218 and any lumens, channels, controllers or communication devices related to the catheter system. The microbubble reservoir 1232 and port or channel 1233 is adapted to release microbubbles that are intended to be located into or proximal to the treatment site 1210 at the desired or applicable location 1211 of the subject 1211, such as vessel, organ, anatomical structure, anatomical tubular structure, or duct, etc. The system 1202 further comprises an ultrasonic energy source(s) 1212 in communication with the distal region (or other region as desired or required) of the tubular member 1218 (as well as other components or subsystems or components of the present invention). The ultrasonic energy is adapted for or capable of: imaging the treatment site 1210, and rupturing the microbubbles. For instance, therapeutic array 1236 (comprising a predetermined ultrasound system design as desired or required) for bursting the microbubbles are provided (e.g., at low frequency LF or as desired or required). Further, an imaging array 1237 (comprising a predetermined ultrasound system design as desired or required) is provided for imaging (e.g., at high frequency array HF or as desired or required). Further yet, the ultrasonic energy source 1238 (comprising a predetermined ultrasound system design as desired or required) may provide ultrasonic radiation forces for translating or transporting the microbubbles 1234 (e.g., at low frequency LF or high frequency HF, or combination thereof, or as desired or required) into or in the vicinity of the treatment site 1210 or region at the desired or applicable location 1211 of the subject.

Still referring to FIG. 12(A), the system 1202 further comprises (although not shown) a control circuitry configured to send electrical activation to the ultrasonic energy source, as well as other components and subsystems of the present invention. Further, regarding the translation or transportation of the microbubbles or applicable medium, mechanical forces may be provided in place of the ultrasound forces (acoustic wave) or in combination with the ultrasound for translating the microbubbles into or in the vicinity of the treatment site 1210 to achieve the desired or required result.

It should be appreciated that the aforementioned catheter 1218, microbubble reservoir 1232, microbubble port or channel 1233, ultrasound source(s) 1212, and controller may be disposed entirely inside the applicable location of the subject 1211, outside the location of the subject or a combination of inside or outside the location of the subject. The one or more locations 1211 of the subject may be an organ. The organ may include hollow organs, solid organs, parenchymal tissue, stromal tissue, and/or ducts. The one or more locations 1211 of the subject may be a tubular anatomical structure. The tubular anatomical structure may be a blood vessel. Further, for example, the treatment site 1210 may be a vasculature treatment site comprising at least one of the following: stenotic region or any region exhibiting vascular disease. Further, for example, the treatment site 1210 may be a vasculature treatment site and/or a diagnostic site.

Figure 12B:
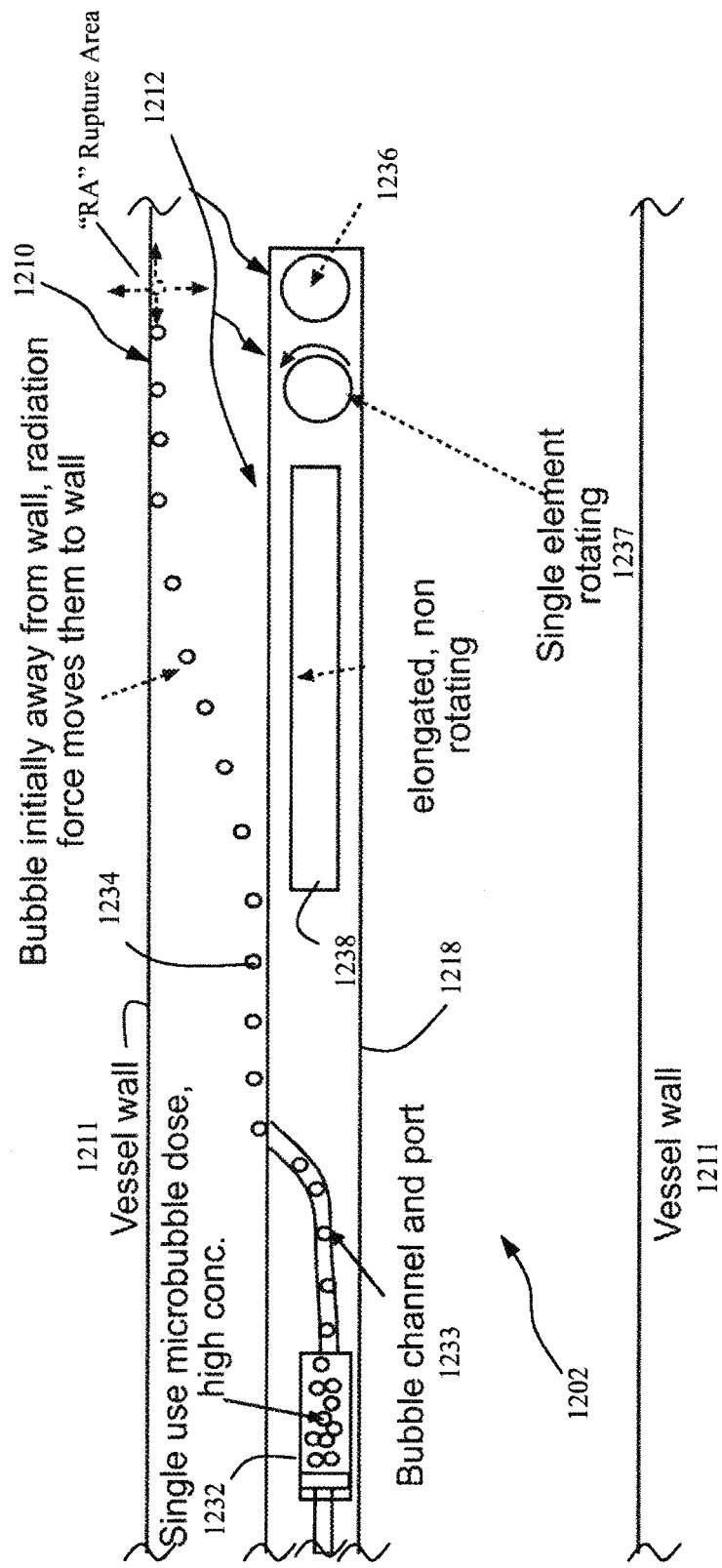

FIG. 12(B) schematically illustrates an embodiment (or partial embodiment) of the present invention ultrasound catheter system 1202 for providing therapy (as well as diagnostic if desired or required) to a treatment site at one or more locations of a subject. The catheter system 1202 may comprise a tubular member such as a catheter body 1218 or multiple catheters, needles, conduits, housings, or lumens. The catheter(s) having a proximal region and distal region, whereby the distal end portion of the ultrasound catheter is adapted or configured to be advanced to or in proximity to the subject's treatment site or region 1210. It should be appreciated that any one of the catheters 1218 as shown may be a plurality of catheters and any given catheter may have one or more lumens therein. The system further comprises a microbubble reservoir 1232 in hydraulic communication with the port or channel 1233 and in hydraulic communication with the tubular member 1218 and any lumens, channels, controllers or communication devices related to the catheter system. The microbubble reservoir 1232 may be single use microbubble dose and high concentration. Moreover, the reservoir 1232 may comprise multiple uses and have a variety of concentrations as desired or required. The microbubble reservoir 1232 and/or port or channel may be a capillary size or larger, or the microscale or smaller such as a microchip, lab-on-a-chip, or in-situ design. The microbubble reservoir 1232 and port or channel 1233 is adapted to release microbubbles that are intended to be located into or proximal to the treatment site 1210 at the desired or applicable location, such as a vessel or vessel wall 1211 of the subject. The system 1202 further comprises an ultrasonic energy source 1212 in communication with the distal region (or other region as desired or required) of the tubular member 1218 (as well as other components or subsystems of the present invention). The ultrasonic energy is adapted for or capable of: imaging the treatment site 1210, and rupturing the microbubbles. For instance, therapeutic array 1236 for bursting the microbubbles are provided (e.g., at low frequency LF or as desired or required). The therapeutic array 1236 comprises a bubble rupture transducer that may be a rotating type; or may be a non-rotating type and be aligned with the radiation force transducer 1238 (or any combination thereof). Further, an imaging array 1237 is provided for imaging (e.g., at high frequency array HF or as desired or required). The imaging array 1237 may be rotating or non-rotating and may be a single element or multiple element (or any combination thereof). Further yet, the ultrasonic energy source 1238 may provide ultrasonic radiation forces for translating or transporting the microbubbles 1234 (e.g., at low frequency LF or high frequency HF, or combination thereof, or as desired or required) into or in the vicinity of the treatment site 1210 at the desired or applicable location 1211 of the subject. The radiation force transducer 1238 may be elongated and non-rotating. Alternatively, the shape may also vary and it may rotate as well. Alternatively, rather than a radiation force transducer, a means for transporting or translating may be implemented, such as mechanically or electrically. For instance, but not limited thereto, ejecting the bubbles with sufficient peripheral oriented velocity so as to translate quickly to the vessel wall.

Still referring to FIGS. 12(A)-(B), the system 1202 further comprises (although not shown) a control circuitry configured to send electrical activation to the ultrasonic energy source, as well as other components and subsystems of the present invention. Further, regarding the translation or transportation of the microbubbles or applicable medium, mechanical forces may be provided in place of the ultrasound forces (acoustic wave) or in combination with the ultrasound for translating the microbubbles into or in the vicinity of the treatment site 1210 to achieve the desired or required result.

It should be appreciated that the aforementioned catheter 1218, microbubble reservoir 1232, microbubble port or channel 1233, ultrasound source(s) 1212, and controller may be disposed entirely inside the applicable location of the subject, outside the location of the subject or a combination of inside or outside the location of the subject. The one or more locations 1211 of the subject may be an organ. The organ may include hollow organs, solid organs, parenchymal tissue, stromal tissue, and/or ducts. The one or more locations 1211 of the subject may be a tubular anatomical structure. The tubular anatomical structure may be a blood vessel. Further, for example, the treatment site 1210 may be a vasculature treatment site comprising at least one of the following: stenotic region or any region exhibiting vascular disease. Further, for example, the treatment site 1210 may be a vasculature treatment site and/or a diagnostic site.

Still referring to FIGS. 12(A)-(B), for example (as well as other embodiments discussed herein), the system 1202 may comprise, but not limited to the following:

Imaging transducer may be scanned single element or array;

Orientation of scanning transducer/array may be annular format per conventional;

IVUS or may be longitudinal (or other) format;

Longitudinal format is like shown here for the radiation force transducer and may be similar to the Siemens AcuNav intracardiac catheter transducer array;

Radiation force transducer may be a single element, focused element;

It might be an annular array for multiple focal option;

Frequency of each transducer/array may be different;

Radiation force transducer may be high frequency;

Imaging radiation may be high frequency;

Rupture radiation may be low frequency;

Rupture and imaging could be coincident—one over the other;

Bubbles are conceptually injected via a port;

Bubbles may be injected freely via the same access catheter (i.e. ~2 mm tube or as desired);

Bubbles may be saved in a single use, concentrated form near the catheter tip. This would allow us to use a smaller number of bubbles. Keeping the bubbles in high concentration (i.e. low rate of outward diffusion) allows them to be time stable);

Bubbles may be monodisperse (all same size), but not necessarily;

In principle, bubble dispersions can be sorted.

Figure 13:
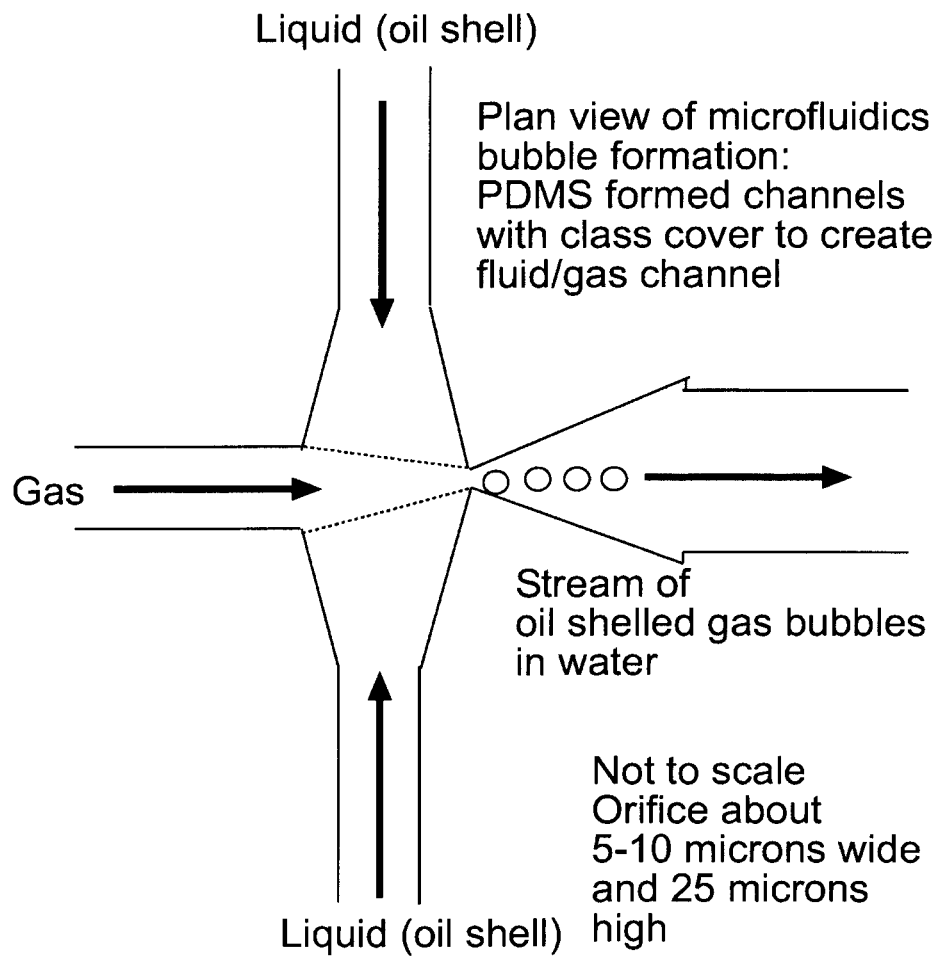
FIG. 13 provides a plan schematic view of the micro fluidic flow-focusing device or in-situ device.

FIG. 13 illustrates a schematic plan view of the "On-chip generation of microbubbles as a practical technology for manufacturing contrast agents for ultrasonic imaging" by Kanaka Hettiarachchi, Esra ¹TaIu, Marjorie L. Longo, Paul A. Dayton and Abraham P. Lee Lab on a Chip, 2007, 7, 463-468, which is hereby incorporated herein, in its entirety, by reference thereto. Provided is the soft molded PDMS (silicone) based micro flow chamber below. An aspect of the present invention may utilize some aspects. An embodiment of the present invention provides a segment of a device that easily fits at the tip of a catheter. This approach has many features and characteristics:

1. Increased versatility—can vary shell composition (i.e. potentially drug/gene payload and concentration "on the fly");
2. Enables otherwise unfeasible bubbles. Making the bubbles at the tip means that stability problems are mitigated. The bubbles only have to survive a few seconds before therapeutic delivery. This may enable less stable chemical formulations or less stable bubble (i.e. shell/gas) permutations. Currently, gas is limited to one with very low rate of diffusion (i.e. high molecular weight). The new design enables the use of new gases or light gases at a minimum. This area isn't properly explored yet in our opinion.
3. Existing problems with bubble stability that require complex handling are circumvented.

Still referring FIG. 13, FIG. 13 provides a schematic plan view of the microfluidic flow-focusing device or in-situ device. The microfluidic device may be less than about 1 mm and therefore can be fit inside a catheter for example. The arrows indicate direction of flow of liquid inlet(s) and gas inlet.

It should be appreciated that the widths and heights may be larger or smaller as required. The contours and shapes may vary as well.

Figure 14A:
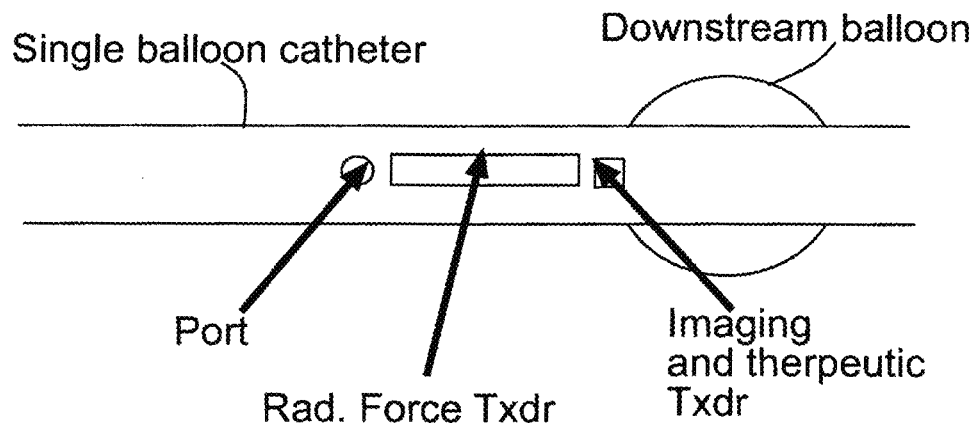
FIGS. 14(A)-(B) provide a schematic elevation view of embodiments of the catheter system having occlusion or sealing systems.

FIG. 14(A) provides a schematic elevational view of an embodiment (or partial embodiment) or approach of the present invention that provides a single occlusion balloon to temporally stop flow—distal to transducer and drug bubble port. The balloon may be released (or partially released) after procedure (or during the procedure) and drug bubble residual or other medium flows systemically or as available.

Figure 14B:
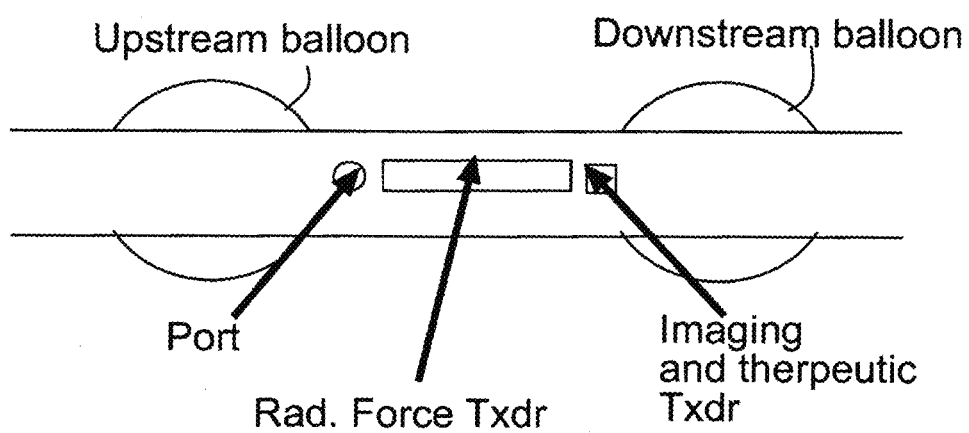

FIG. 14(B) provides an embodiment similar to device as shown in FIG. 14(A), however the instant embodiment or approach of the present invention provides a dual occlusion balloon to stop flow (or hinder flow) and create a sealed vessel section (or partially sealed section) in which drug (or applicable medium) is injected, delivered and then flushed to eliminate systemic delivery concerns. The instant approach may also include a second port well separated from first so as to permit flush in from one and vacuum out at other—i.e. ports upstream and downstream and close to each of the balloons (or located as desired or required).

The balloons may be any available sealing, occluding or blocking designs, structure, or devices available to those skilled in the art (or so as to provide partial occlusion when applicable or desired).

Examples of balloon (or occlusion) related catheter devices and associated methods are provided in the references listed below, each of which is incorporated herein, in its entirety, by reference thereto.

An important practical problem with the use of microfluidics devices in the present invention relates to achieving seals between inlet liquid and gas tubes and the microfluidics device. FIGS. 15A-15E illustrate various aspects of the present invention provided to promote adequate and sustained sealing between inlet fluid and gas tubes and a microfluidics device Important is achieving a seal that can withstand internal pressurization without failing or leaking.

Figure 15A:
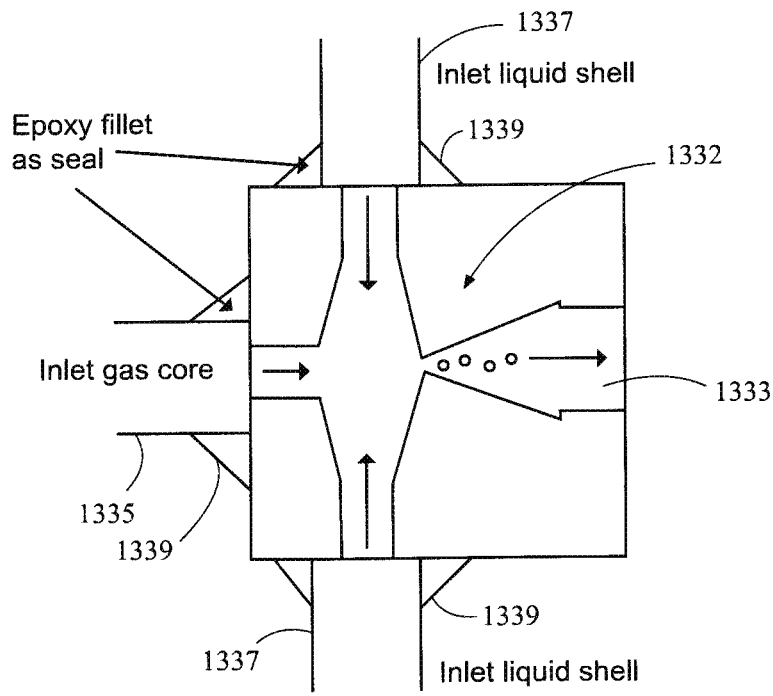
FIGS. 15A-15E illustrate various embodiments for sealing the interfaces inputting to a microfluidics device according to various embodiments of the present invention.

In at least one embodiment seals between the gas core inlet tube 1335 and the device 1332 at the inlet, as well as between the liquid shell inlet tubes 1337 and the liquid inlets of the microfluidics device 1333 can be provided by fillets of adhesive around the circumferences of the interfaces, as illustrated in the longitudinal sectional, schematic illustration of FIG. 15A. Epoxies are one class of many adhesives suitable for this task. Depending on the surfaces of the materials (tubes 1335, 1337 and inlets of device 1332) being used, it may be preferable to surface treat or prime either or both the microfluidics device 1332 or the tubing 1335, 1337. For example, polytetrafluoroethylene (PTFE) tubing is best prepared using an etchant such as Fluoroetch (Acton Technologies, Pittston, Pa.). This etchant operates by stripping the fluorine from the carbon backbone and promoting its replacement with hydroxyl, carbonyl and carboxyl groups which are the organic species responsible for adhesion.

In at least one embodiment, polyethylene (PE) tubing is used. PE tubing is available from many sources—e.g. Instech Labs, Plymouth Meeting, Pa., USA. Examples of PE tubing that may be used include, but are not limited to: BPE-T10 PE-10 tubing, 0.011"ID×0.024"OD; BPE-T20 PE-20 tubing, 0.015"ID×0.043"OD; and/or BPE-T25 PE tubing, fits 25 ga, 0.018"ID×0.036"OD. Generally, smaller tubing may be better from a clinical perspective—i.e. small overall catheter size (OD—outside diameter). Larger tubing is preferable from a technical perspective—reducing resistance to flow and pressure drop. The optimum design is a result of a tradeoff between these competing preferences.

Microfluidics devices are described in many papers (including the Hettiarachchi paper mentioned and incorporated herein). Stanford Microfluidics Foundry offers a service wherein automated computer aided design (ACAD) designs are received and etched silicon wafers are delivered and these are used as molds for polydimethlysiloxane (PDMS) casting.

There are a multitude of adhesives that can be used for the sealing process. One non-limiting example of an epoxy that can be used is Hysol RE2039/HD3051, distributed by Loctite, 7630 W. 78th Street, Bloomington, Minn. 55439. Since PDMS does not always adhere well (as a substrate), it is sometimes preferred to activate the surface using a plasma oven.

Figure 15B:
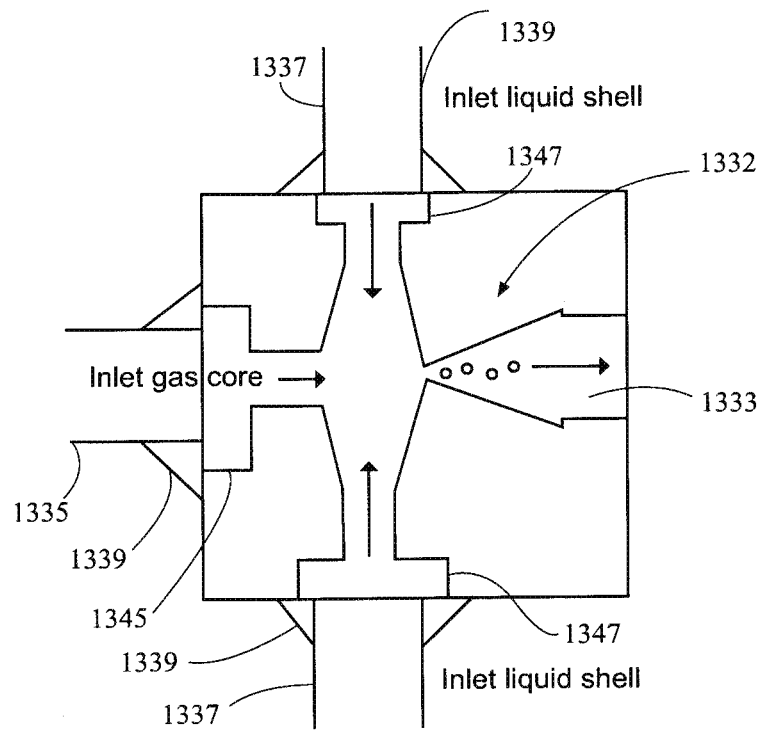

FIG. 15B illustrates an embodiment wherein an elongated insertion recess 1345, 1347 is provided to increase the interfacial area between the tube 1335, 1337 and corresponding inlet of the microfluidics device 1333. Additionally, each recess 1345, 1347 can be sized to distort (e.g., "pinch") the cross-sectional shape of the corresponding tube 1335, 1337 to still further increase the interfacial area between the components as well as to increase the friction between the components. FIG. 15D illustrates a substantially circular cross-sectional shape of tubes 1335 and 1337 in their undistorted configurations. FIG. 15E illustrates a cross-sectional shape of a tube 1335 or 1337 having been distorted by insertion in to recess 1345 or 1347, respectively. It is further noted that, in at least one embodiment, seal enhancement may be provided by use of recesses 1345, 1347 without fillets.

FIG. 15B schematically illustrates an embodiment in which the distorting entrance recesses 1345, 1347 and the adhesive fillets 1339 are both employed. At the point of entry, the tubes 1345, 1347 flatten and become wider in lateral dimension and reduced in height dimension.

Figure 15C:
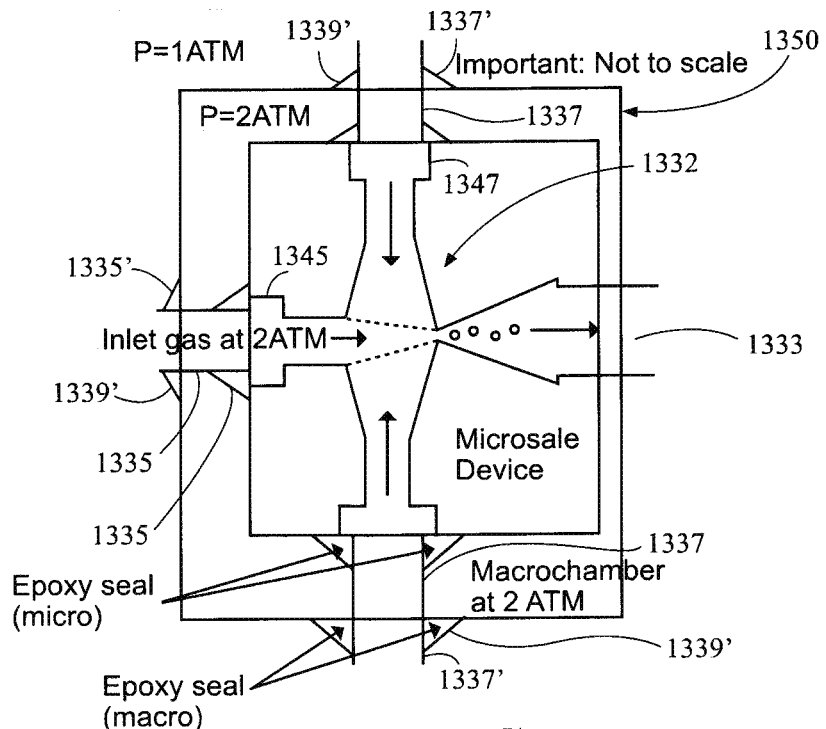
Figure 15D:
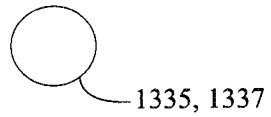
Figure 15E:
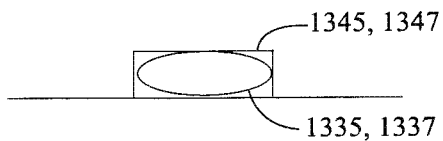

FIG. 15C illustrates an embodiment, in which the entire structure of microfluidics device 1332, excluding the exit port 1333, is placed inside of a macro chamber 1350 that is itself pressurized to a pressure greater than a pressure outside of the chamber 1350, preferably, but not necessarily pressure to a pressure approaching or approximately the same as that internal to the microfluidics device 1332. In this way, the differential pressures across the interfaces (1335 to 1345 and 1337 to 1347) going into the microfluidics device are close to zero, or at least much less than if the pressurized macro chamber 1350 were not employed. In this example, the internal pressure is 2 ATM—but it could be any pressure and might be much higher if the intent is to increase bubble production rate. An advantage of this approach is, but not limited thereto, that it is simpler to achieve high pressure bonding on a macro scale chamber than on a micro scale chamber. Further, tubes 1335' and 1337' may be, but are not necessarily, of a larger scale that corresponding tube 1335, 1337. When larger tubes are used, this provides more interfacial area to be bonded by the fillets 1339'.

Alternate Microfluidics Device Materials

An embodiment of the device 132 may use soft rubber-like materials such as Dow Corning Sylgard 184 poly (dimethylsiloxane) (PDMS). This material is amenable to molding from silicon, glass or SU8 photoresist features. However, when subject to high pressure, it may tear. Therefore, alternative materials are appropriate and may be implemented for various embodiments. These materials may include: Silicon, glass (all forms—soda lime, borosilicate etc.) and photoresists/polymers such as SU8. Other polymers are possible too—such as poymethylmethacrylate (PMMA). Some of these latter materials will require more complex device geometry formation. For example, silicon may require chemical etching, reactive ion etching (RIE) or laser micromachining. The present invention is not specific to a particular material or method of device formation.

Alternate Gas Core Materials $C_4F_{10}$ is the most popular gas core in commercially produced ultrasound microbubbles because of its very low rate of diffusion out of the core through the shell into surrounding water-based media. Even in the case of $C_4F_{10}$ there is still some diffusion and this suggests the long term storage of microbubbles with a $C_4F_{10}$ saturated filled headspace above the contrast in the containing vial. However, in the context of the various embodiments of the present invention in which the microbubbles are formed immediately prior to use, longevity may not be a concern. In fact, short lifetime in the body may be a major advantage. For example, we envisage using air filled microbubbles that quickly dissolve in the case that bubbles escape the intended therapeutic zone. By using quickly dissolving microbubbles, we can mitigate against the risk of unwanted downstream embolus such as in the lung. The approach of using an unstable bubble may also uniquely enable the use of far larger bubbles (such as in the range 10-20 μm). We set forth that larger bubbles result in greater therapeutic effect by way of greater penetration into vessel wall during the process of fragmentation induced by ultrasound.

Modifications to Shell Material

Increasing shell liquid viscosity has the effect of reducing produced bubble dimension—all other variables held constant. Various shell liquid additives can be considered to achieve this effect. These include: sucrose, glycerol and dextran. Additionally, it is possible to modify shell viscosity in some cases by taking advantage of the thermal dependency of shell liquid viscosity. For example, a Peltier effect device may be used to provide local cooling on a micro, or close to micro, scale. The Peltier effect for cooling a microfluidics device is described by Maltezos et al., "Thermal management in microfluidics using micro-Peltier junctions," *Appl Phys Lett*, vol. 87, pp. 154105(1-3), 2005, which is hereby incorporated herein, in its entirety, by reference thereto. Marlow Industries (Dallas, Tex.) supplies Peltier-based thermocoolers for the microelectronics industry. A device such as the NL1010T-01 can be adapted for the purposes of cooling a microfluidics device (although this particular part number would not be catheter compatible in most instances.)

OCT Catheter-based Imaging

Figure 16:
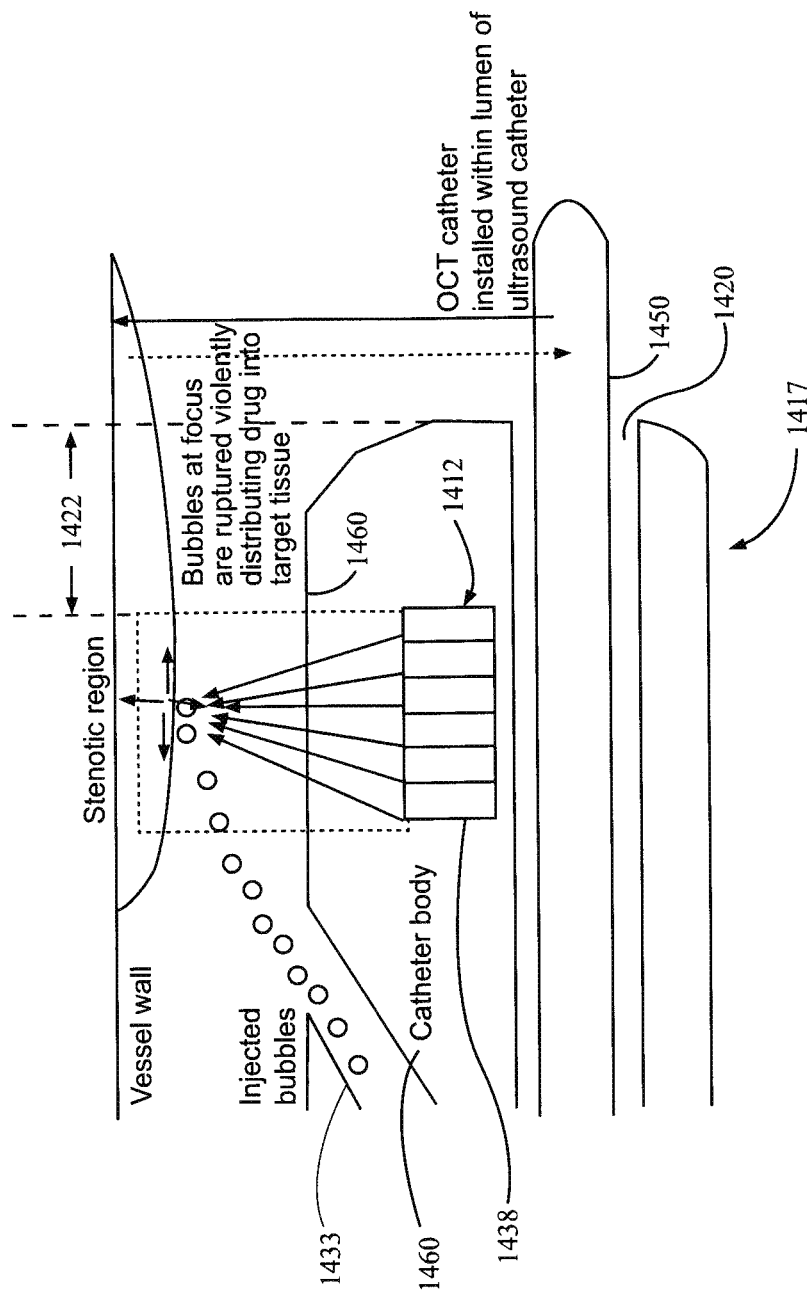
FIG. 16 is a schematic illustration of a distal end portion of a system according to an embodiment of the present invention, in which an optical coherence tomography (OCT) catheter is installed within a lumen an ultrasound (IVUS) catheter.

In at least one embodiment, the present invention may include a dual lumen catheter wherein one lumen is dedicated for the passage of an existing catheter. Preferably, an optical coherence tomography (OCT) imaging catheter. Lightlab LLC has developed an OCT catheter system referred to as the Helios occlusion catheter and ImageWire OCT imaging catheter. An implementation of a joint OCT/IVUS drug/gene delivery system would be to create a dedicated therapeutic ultrasound catheter comprising a therapeutic single element installed near the tip of an appropriately-sized catheter tube (such as sized approximately 1 mm in diameter) with electrical wires to top and bottom of the piezoceramic single element. The ultrasound catheter should also possess a lumen and port to provide for passage of microbubbles in saline solution through the length of the catheter and exit into the vessel proximal with respect to the ultrasound element. An ImageWire OCT imaging catheter is bonded, with glue (such as epoxy), to the ultrasound catheter. The ImageWire can be used in conjunction with the Helios occlusion catheter as per normal OCT use. During OCT scanning, the ultrasound element 1412 and bubble injection (via microbubble lumen 1433 and ejection port 1434) are active according to user switch-on in response to OCT imaging. Although a portion of the OCT circumferential field of view may be obscured by the ultrasound catheter, blind spots can be avoided by rotating the catheter pair. In the schematic illustration of FIG. 16, the OCT catheter 1450 is installed within the lumen 1420 of the ultrasound catheter 1417. The image plane (circumferential) is offset laterally (in a distal direction) with respect to the ultrasound therapeutic zone. Ideally, the OCT image plane offset is minimal by making the physical distance 1422 between the ultrasound device/transducer 1438 and the end of the catheter 1417 minimal so that the most proximal viable imaging plane of the OCT catheter 1450 is only offset by about 1 mm. Alternatively, the OCT plane can be within the ultrasound catheter but in this case some imaging artifacts are likely.

Simplification of Gas and Fluid Delivery Arrangements

Figure 17A:
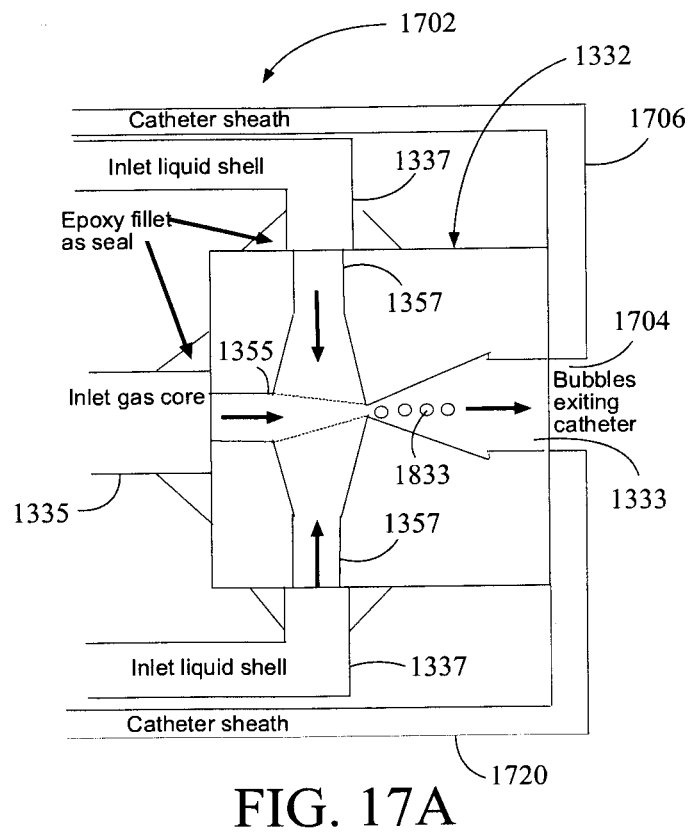
FIG. 17A schematically illustrates an arrangement in which a microfluidics device is contained within a distal end portion of a catheter system according to an embodiment of the present invention.

In an integrated catheter system including microbubble generating microfluidics as disclosed according to the present invention, various embodiments are provided for simplifying the structures provided for delivery of gas and shell fluid to the microfluidics device 1332. FIG. 17A schematically illustrates an embodiment in which microfluidics device 1332 is contained within a distal end portion of the catheter system 1702, within catheter 1720. In all three embodiments of FIGS. 17A-17C, microfluidics device 1332 is placed in the catheter distal tip so that the output port 1333 outputs microbubbles 1334 directly out of the system 1702, as output port 1333 interfaces against opening 1704 in the distal end 1706 of catheter 1720. Thus, for example, output bubbles may free flow out of device 1332/output port 1333, out of catheter lumen 1704 and into the bloodstream, near the center axis of the catheter 1720 and blood vessel. It is noted however, that the arrangements described here are not limited to placement of device 1332 in the distal tip in the manner shown in FIGS. 17A-17C, as device 1332 could be set proximally of the distal tip and output port 1332 may be arranged to interface an opening in the side of the catheter tubing 1720 or may be connected via a tube to opening 1704 or an opening in the side wall of the catheter tubing 1720.

In FIG. 17A thin tubing 1335, 1337 interfaces to the gas input port 1355 and liquid shell input ports 1357 of microfluidics device 1332 in a manner like that described above with regard to FIG. 15A. However, these interfaces may alternatively be made in any of the other manners described above with regard to FIGS. 15B-15E. Thus, three tubes (one tube 1335 for gas and two tubes 1337 for two liquid (shell) input ports 1357) are connected to microfluidics device 1332 in the embodiment shown in FIG. 17A.

Figure 17B:
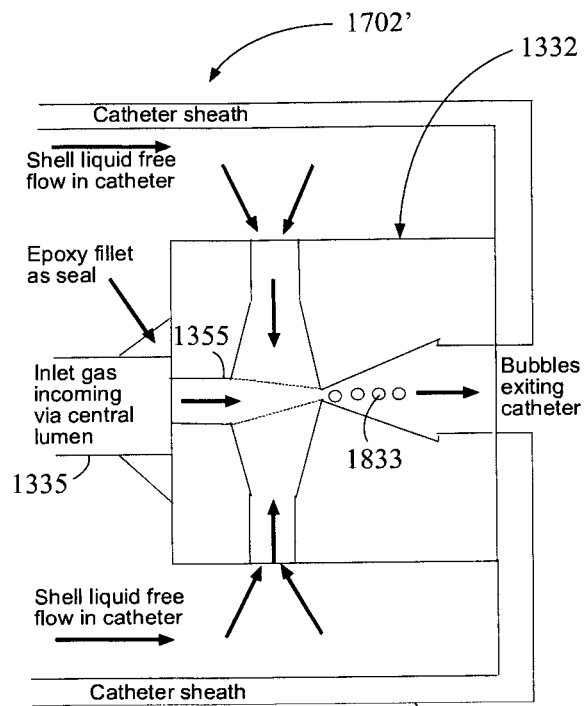
FIG. 17B schematically illustrates an arrangement in which a microfluidics device is contained within a distal end portion of a catheter system according to another embodiment of the present invention.

FIG. 17B schematically illustrates an embodiment of a system 1702' that simplifies the structure needed to transport gas and liquid down the catheter 1720 of the catheter system to feed the microfluidics device to produce microbubbles. In FIG. 17B, a tube 1335 is enclosed within the outer catheter 1720 that carries the microbubble gas phase. Tube 1335 thus interfaces with gas input port 1355 forming a seal therewith, according to any of the techniques described above with regard to FIGS. 15A-15E, for example. The space defined between the inner wall of the catheter sheath 1720 and the external wall of the tube 1335 is used to carry and deliver the liquid (shell) phase to the device 1332 through liquid input ports 1357. Thus, ports 1357 are in fluid communication with the space defined between the inner wall of the catheter sheath 1720 and the external wall of the tube 1335. This modification reduces the number of tubes required for delivering gas and liquid from three to one. Likewise, only one seal, rather than three are required.

Figure 17C:
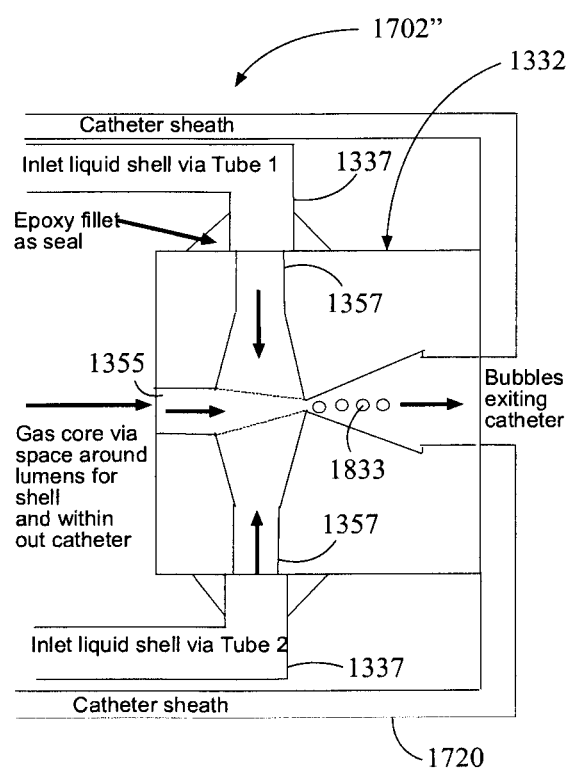
FIG. 17C schematically illustrates an arrangement in which a microfluidics device is contained within a distal end portion of a catheter system according to another embodiment of the present invention.

FIG. 17C schematically illustrates an embodiment of a system 1702" that simplifies the structure needed to transport gas and liquid down the catheter 1720 of the catheter system to feed the microfluidics device to produce microbubbles. In FIG. 17C, two tubes 1337 is enclosed within the outer catheter 1720, and these two tubes 1337 carry the liquid (shell) phase to the microfluidics device 1332. Tubes 1337 thus interface with respective fluid input ports 1357 forming a seal therewith, according to any of the techniques described above with regard to FIGS. 15A-15E, for example. The space defined between the inner wall of the catheter sheath 1720 and the external walls of the tubes 1337 is used to carry and deliver the gas phase to the device 1332 through gas input port 1355. Thus, port 1355 is in fluid communication with the space defined between the inner wall of the catheter sheath 1720 and the external walls of the tube 1337. This modification reduces the number of tubes required for delivering gas and liquid from three to two. Likewise, only two seals, rather than three are required.

The embodiment of FIG. 17B is currently preferred because the gas phase is typically under significant pressure in normal use, whereas the liquid phase in under controlled flow rate and may be lower pressure. Also, as noted above, the embodiment of FIG. 17B simplifies more as it reduces the total number of interfaces of tube/device from three to one.

Figure 18:
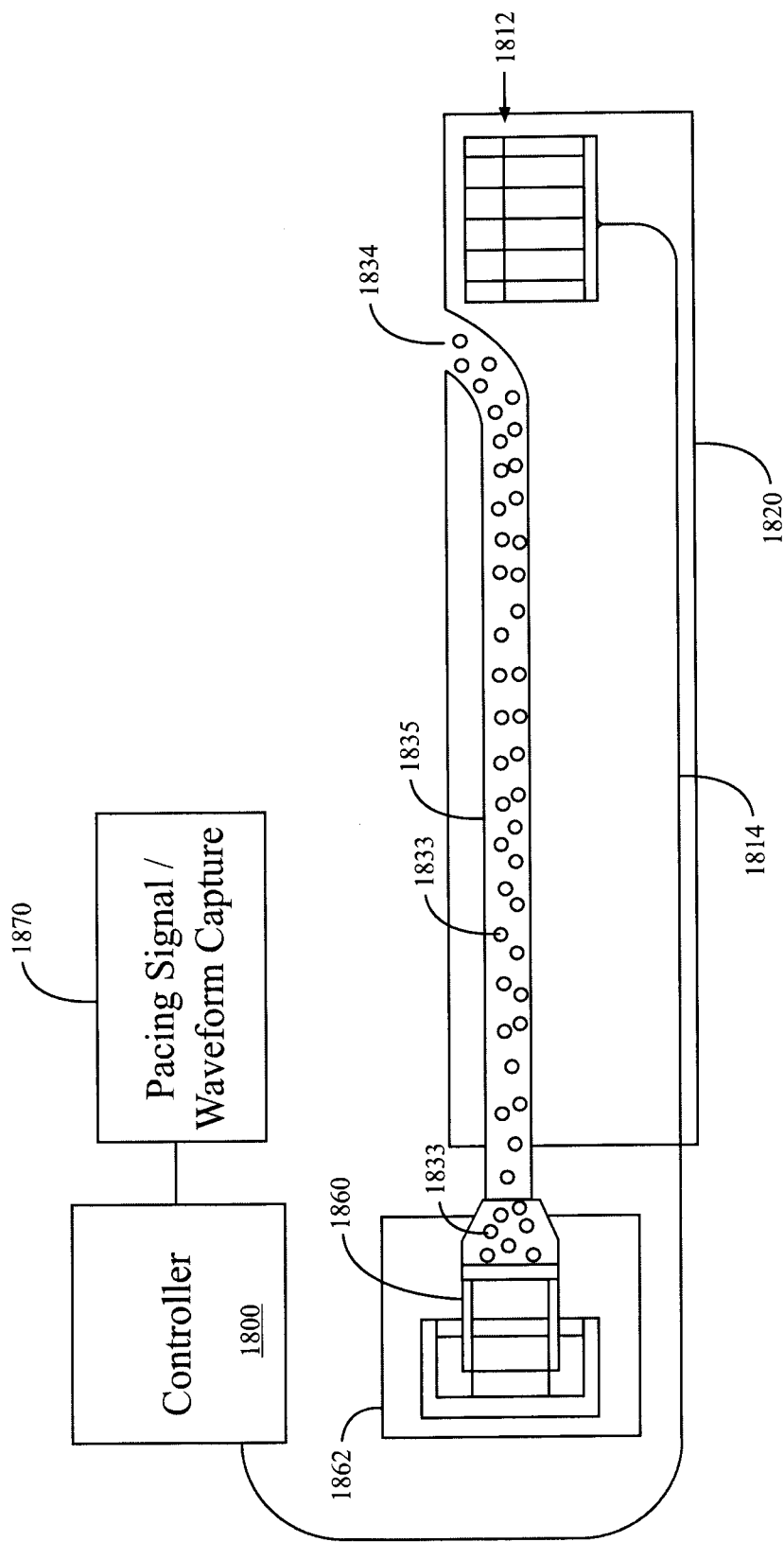
FIG. 18 schematically illustrates a system employing a continuous bubble channel lumen according to an embodiment of the present invention.

Several of the proposed blood vessels in which the catheter systems according to the present invention may be used in involve highly pulsatile blood flow—i.e., the coronary and carotid vessels—both of which are very short distances from left side of the pumping heart. Since blood flow during pumping (systole) can be tens of centimeters per second and since blood flow between left ventricular (LV) contractions (i.e. diastole) is very low—close to zero—it may be advantageous to pace microbubble infusion to the cardiac cycle. The actual catheter implementation to achieve this may take several forms:

One form employs a continuous bubble channel lumen 1833, see FIG. 18. Before use, the microbubble channel 1835 is charged with microbubbles 1833 in saline (per standard injectate protocol). The catheter distal end 1806 is inserted into a patient vessel and passed to region of interest (e.g. coronary vessel). The proximal end portion 1808 is connected to a syringe 1860 that contains microbubbles 1833 in saline and syringe 1860 is fitted to a syringe pump 1862 capable of pulsing flow. Syringe pumps are well known in the field and many of them are capable of computer control via a suitably matched interface—such as USB, GPIB or RS232C. Harvard Instruments is a well-known supplier of research grade syringe pumps. This configuration works well when there is a large volume and number of bubbles available—because the proportion of bubbles lost by way of the finite capacity of both the syringe and catheter lumen is large in relation to the amount expelled from the catheter tip.

In embodiments where pulsatile pumping is employed, logically, the pacing signal is via conventional ECG waveform capture by ECG sensing of the patient's heartbeat and conversion to a pacing signal by capture and conversion module 1870. Typically, the R-wave is readily detectable and this precedes systole. The delay between ECG R-wave peak and the optimal time for bolus injection of microbubbles 1833 is a function of heart rate and vessel location in relation to heart. In any event, the delay between detected R-wave and time to bolus pump can be determined experimentally and is logically described a fraction of the R-R interval (thus accounting for changing heart rate) where the fraction depends on vessel location. Controller 18 (which may be a computer and includes at least one processor) may use a look up table to include an experimentally determined delay factor for controlling the bolus infusion by pump 1862 to occur at a time resulting from the time of receipt of a R-wave signal plus the delay time that most closely corresponds to the location where the microbubbles are being delivered. Alternatively, or additionally, controller 1800 may interpolate between delay times stored in a lookup table, or may calculate a delay time based upon user input of the location of the target (and or distance of the target from the heart) where the microbubbles 1833 are to be delivered. The transducer array 1812 operates in a manner as described previously. Control wiring 1814 may extend from the transducer array 1814, out of the proximal end portion 1808 of catheter 1820 and be electrically connected to controller 1800 for control of transducer operations by controller 1800. These features for pulsatile pumping control, while described and shown with regard to FIG. 18, can be employed in other embodiments employing pulsatile pumping or flow, such as the embodiment of FIG. 19A, for example.

In another embodiment, microbubbles 1833 may be formed in the distal end portion of the catheter. For example, in the embodiment of FIG. 19A, microbubbles 1833 are continuously outputted from the output port 1333 of microfluidics device 1332, accumulate in tube 1937 and eventually flow into lumen 1935. An external pump (not shown), which may be an arrangement like that shown in FIG. 18 or some other external pump arrangement that can be controlled to pump saline in a pulsatile manner timed to the heartbeat, is in fluid communication with limen 1935 and configured to pump saline therethrough in a pulsatile manner like described above. With each pulse of the pump, the pulsing saline drives a bolus 1933 of microbubbles 1833 toward the port 1904 of catheter 1920 where they are outputted toward the target. The mircrobubbles 1833 are flushed out of the catheter 1920 in a bolus 1933 as illustrated in FIG. 19A, during the diastolic phase using a saline flush connected to the pulsatile pump source.

Figure 19A:
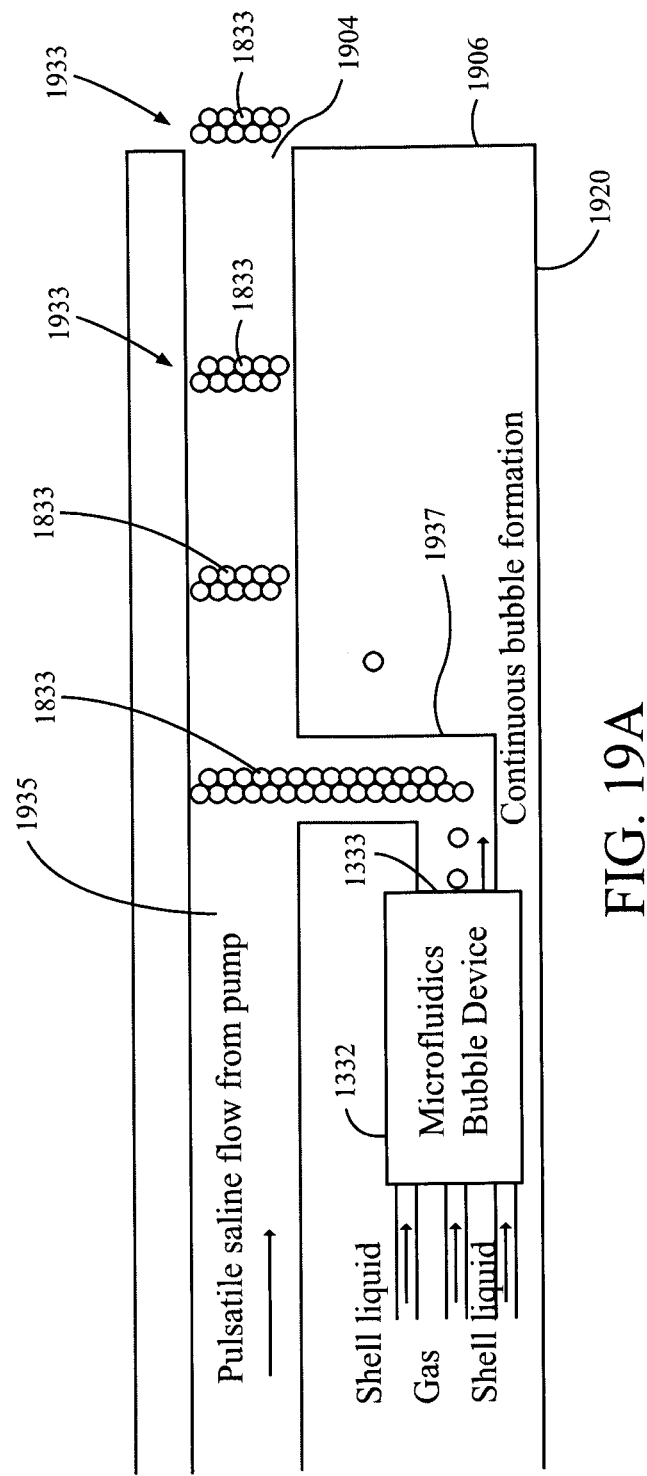
FIG. 19A schematically illustrates a system employing pulsatile flow from a pump external of a catheter and in which a microfluidics device is employed within the catheter, according to an embodiment of the present invention.
Figure 19B:
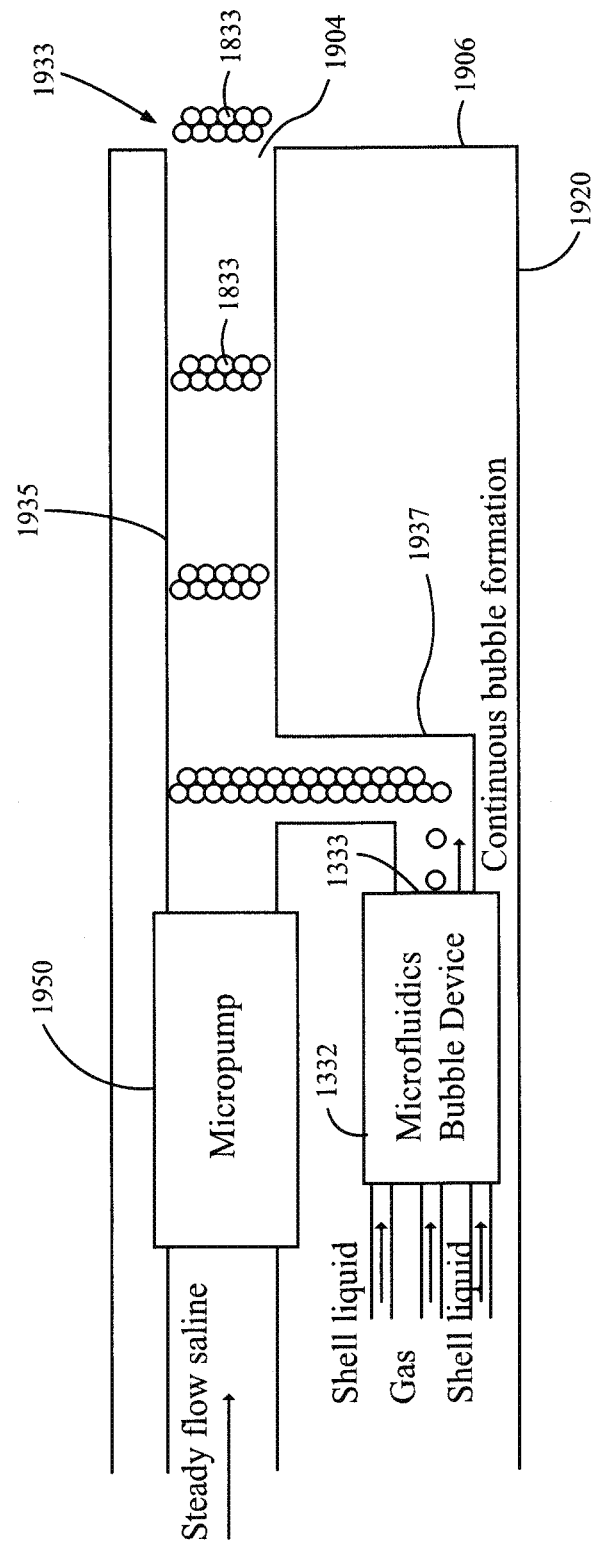
FIG. 19B schematically illustrates a system employing a micropump within a catheter and in which a microfluidics device is employed within the catheter, according to an embodiment of the present invention.

FIG. 19B schematically illustrates an embodiment in which a micro pump 1950 is housed within the catheter 1920 itself, preferably, but not necessarily in the distal end portion of the catheter. Micro pump 1950 is in fluid communication with and outputs to lumen 1935 of catheter 1920. A pressurized source of saline (not shown) outside of (proximal of) the catheter 1920 is in fluid communication with and provides a steady flow of saline to micropump 1950. Microfluidics device 1332 operates in the same manner and is connected in the same manner as described above with regard to the embodiment of FIG. 19B. Micro pump 1950 outputs pressurized pulses of saline, and may be timed and controlled to the heartbeat of the patient in the same manner as described above with regard to FIG. 18. With each pulse of the micro pump 1950, the pulsing saline drives a bolus 1933 of microbubbles 1833 toward the port 1904 of catheter 1920 where they are outputted toward the target. The microbubbles 1833 are flushed out of the catheter 1920 in a bolus 1933 as illustrated in FIG. 19B, during the diastolic phase by the pressurized pulses of saline provided by the micro pump 1950.

Figure 19C:
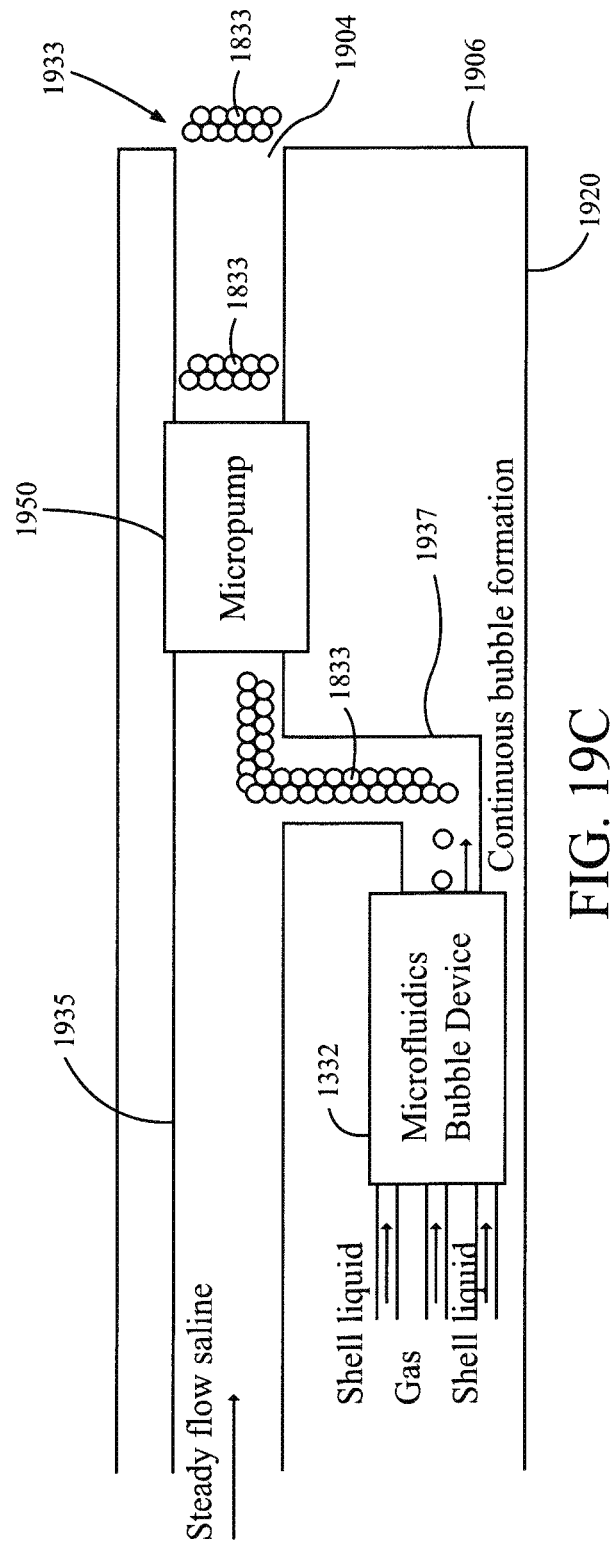
FIG. 19C schematically illustrates a system employing a micropump within a catheter and in which a microfluidics device is employed within the catheter, according to another embodiment of the present invention.

FIG. 19C schematically illustrates an embodiment in which a micro pump 1950 is housed within the catheter 1920 itself, preferably, but not necessarily in the distal end portion of the catheter. In this embodiment, micro pump 1950 is in fluid communication with and outputs to lumen 1935 of catheter 1920. A pressurized source of saline (not shown) outside of (proximal of) the catheter 1920 is in fluid communication with and provides a steady flow of saline into micro pump 1950. Additionally, in the embodiment, microfluidics device 1332 inputs microbubbles into micro pump 1950 via 1937 and 1935, as shown. Preferably, the microbubbles 1833 are continuously inputted to micro pump 1950, but in any case, microbubbles 1833 accumulate sufficiently to form a bolus 1933 for each pulse of the micro pump. Micro-pump 1950 thus outputs pressurized pulses of saline plus a bolus of microbubbles 1833 with each pulse, and may be timed and controlled to the heartbeat of the patient in the same manner as described above with regard to FIG. 18. With each pulse of the micro-pump 1950, a bolus 1933 of microbubbles 1833 is driven toward the port 1904 of catheter 1920 where they are outputted toward the target. The microbubbles 1833 are flushed out of the catheter 1920 in a bolus 1933 as illustrated in FIG. 19C, during the diastolic phase by the pressurized pulses provided by the micro pump 1950.

An external pump such as used in the embodiments of FIGS. 18 and 19A, may be a syringe 18960 and syringe driver 1862, as shown in FIG. 18, wherein pumping during that portion of cardiac cycle when problematic high blood flow velocities occur are avoided. This process is then repeated on successive ECG R-wave cycles, each time accumulating microbubbles during the systolic phase and ejecting a bolus during the diastolic phase.

The pulsatile pump used can take many forms. For example: Kandarpa et al., "Forceful pulsatile local infusion of enzyme accelerates thrombolysis: in vivo evaluation of a new delivery system". Radiology. 1988 September; 168(3): 739-44. PubMed PMID: 3406403 (which is hereby incorporated herein, in its entirety, by reference thereto) describes a method in which a syringe is modified by replacing the plunger with a metal cylinder with a rubber O-ring. The plunger is connected via a rod to an eccentrically mounted coupling on a wheel driven by a stepper motor. The stepper motor may be advanced in a pulsatile manner via computer control wherein the computer receives ECG as input triggering signal. Alternative motors and motor controls are possible such as DC servo motors with proportional-integral-derivative (PID) control for example.

Additional discussion of microfluidics scale pumps, which would be capable of limited pulsatile function—i.e. designed to be active during the diastolic phase—may be found in the literature—e.g: Maillefer et al., "A high-performance silicon micropump for disposable drug delivery systems", Proceedings of the MEMS'01, Interlaken, Switzerland, 21-25 Jan. 2001, pp. 413-417 (which is hereby incorporated herein in its entirety by reference thereto). Another source of micro pumps is provided by XAVITECH® Intelligent Pumps, see http://www.xavitech.com/news. Ideally, the micropump is placed immediately adjacent to the microbubble formation device but the micropump may be somewhat upstream where an intracoronary catheter is typically wider—i.e. approximately 2 mm diameter as opposed to 1 mm or less in the distal several cm. In any event, the inlet to the pump is physiological sterile saline. The microfluidics device expels bubbles into the outlet side of the pump (which might be quite far separated—i.e. ranging from <1 mm to multiple cm). The microbubbles accumulate in the outlet side. During pulsatile pump operation, the pump expels a bolus of saline that flushes the microbubble/saline suspension in an outward direction towards the catheter's microbubble port. If not using a microfluidics approach to manufacture bubbles, the microbubbles can be dispensed via the catheter into the outlet side of the pump as per above. Alternatively, the microbubbles are in saline suspension throughout the length of the catheter and pass through the inlet and outlet of the micropump. In this case, consideration must be made for internal pressures encountered during pump operation. In reality, this may have the effect of fracturing a subset of the bubble population and this effect may be mitigated by using a robust bubble design (e.g. polymer shell bubble) or by simply increasing initial concentration in expectation that an approximately known fraction will be lost within the pump.

Additional Mechanisms to Enhance Drug/Gene Delivery.

Electroporation

Electroporation involves applying a moderate AC or DC electric field across target cells—in vitro or in vivo. According to at least one embodiment of the present invention, electroporation may be optionally used in augmentation of the focused ultrasound—not as a substitute. The interaction between focused ultrasound and electoporation is not fully understood—but it is most likely to be a nonlinear process. This means that one or other may be a catalyst to the other—or perhaps each does in fact operate independently (as is already known at a minimal level). Liu has presented results recently on the relative merits of 60 Hz AC fields vs. pulsed DC fields in the range 15-30V/cm—i.e. very low field strengths that may be logically considered safe, see Liu et al., "Sine-wave Current for Efficient and Safe In Vivo Gene Transfer," *Molecular Therapy: Journal of the American Society of Gene Therapy*, vol. 15, pp. 1842-1847, 2007, which is hereby incorporated herein in its entirety, by reference thereto.

In the context of an embodiment of the current invention, electroporation may be achieved by bringing fine wires 1460 (FIG. 16) to the surface of the operating region of the catheter. Logically, these are arranged as a set of longitudinally oriented wires lying for a distance of 1-4 mm and that they may be connected alternately to provide for electric fields between pairs of wires. For example, there might be a total of 8 longitudinally arranged wires arranged alternately "+" and "−" with four of each polarity. The wires may be fine copper single strands, preferably plated with a non-oxidizing metal such as gold, or the structure can be formed using photolithography on a "flex circuit"—as is widely used in the electronics industry. By forming the electrodes using a flex circuit—comprising copper plating on a flexible plastic (e.g. polyester) thin substrate, the resulting structure can be formed by performing the photolithography and developing in the flat form factor and then the device can be rolled up to form a cylindrical with the desired spaced longitudinal electrodes. These wires are connected to a power source, preferably an AC power source operating in the 10's Hz to 1 MHz range. Currently, it is believed that 60 Hz is sufficient and that 15-30V/cm is an adequate and safe electric field to provide some electroporation enhancement.

Local Tissue Heating

Local tissue heating can be used to improve drug/gene delivery to the target tissue. Gao et al., in "Intravascular Magnetic Resonance/Radiofrequency May Enhance Gene Therapy for Prevention of In-stent Neointimal Hyperplasia," *Acad. Radiol.*, pp. 526-530, 2006, and U.S. Pat. No. 7,422,568 to Yang et al. (both of which are hereby incorporated herein, in their entireties, by reference thereto, describe a modified catheter in which the guide wire is attached to a Radio Frequency (RF) electrical source. The RF signal is typically in the range 1-3 GHz—though lower frequencies can be used—such as around 200 MHz. It has been found that only moderate temperature increases are required to enhance efficacy. Generally, it is observed that heating enhances drug/gene delivery rather than being a standalone method for drug/gene delivery—i.e. heating is thought to be best used in combination with electroporation or focus ultrasound/microbubbles. The contents of Gao paper and Yang patent provide a detailed overview of the technology required to implement RF based heating (including some design and modeling details) and these references are incorporated by reference within this document.

Characteristics and Features that May be Implemented m Whole or in Part (in any Permutation) with the Various Embodiments or Partial Embodiments as Discussed An embodiment or approach of the present invention provides Dual use IVUS providing imaging plus therapy.

An embodiment or approach of the present invention provides Rapamycin bubbles (and other drugs with therapeutic effect—primarily antiproliferative but could be others—including dual drug use—such as one drug to precondition tissue for a second drug to operate with enhanced efficacy).

Gene Bubbles

An embodiment or approach of the present invention provides the use of cell-specific promoter constructs to target gene expression specifically to one or multiple cell types in combination or independently. This includes but is not limited to endothelial cell specific promoters (e.g. Tie-2, eNos), smooth muscle cell specific promoters (e.g. SMMHC, SM alpha-actin, SM22-alpha, myocardin), macrophages (e.g. mac-1) and promoters of these genes that have been modified by mutating specific cis DNA sequences so as to limit inhibition of the promoter and increase activity. An example would be, but not limited, to a G/C mutation in the SM22a promoter which renders the promoter active in all smooth muscle cell phenotypes [e.g., Wamhoff et al, Circ Res, 2004]. Genes under control of a tissue selective promoter include but are not limited to anti-proliferative genes such p21, p53, KLF4 and proliferative genes such as PCNA. In one scenario, a proliferative gene is targeted to endothelial cell to promote re-endothelialization and an anti-proliferative gene is targeted to smooth muscle to prevent restenosis.

An embodiment or approach of the present invention provides molecular targeted bubbles (VCAM-1, Platelet Endothelial Cell Adhesion Molecule (PECAM), etc.). The targeting can be in context of diagnosis or therapeutic use of bubbles—or both. The targeting to be any disease with molecular marker on endothelial surface. For example, VCAM-1 for atherosclerotic plaque—including "vulnerable plaque" or $\alpha_{ra}\beta_3$ for angiogenesis associated with cancer.

An embodiment or approach of the present invention provides radiation force and bubbles (which usually involves long pulse bursts, but not necessarily).

An embodiment or approach of the present invention provides IVUS catheter with drug bubble delivery port upstream.

An embodiment or approach of the present invention provides drug delivery "port" is plural and forms an annulus.

An embodiment or approach of the present invention provides a mechanically scanned single element transducer—mechanically scanning achieves the regional coverage. An embodiment or approach of the present invention provides phased array transducer—side fire/annular fire. The phased array may be used for imaging and therapy.

An embodiment or approach of the present invention provides a combination of transducer elements—high power/low frequency, low power high frequency. An embodiment or approach of the present invention provides different transducer elements in different formats—e.g. phased array imaging plus scanned single element therapeutic.

An embodiment or approach of the present invention provides a single occlusion balloon to temporally stop flow—distal to transducer and drug bubble port (for instance, release balloon after procedure and drug bubble residual flows systemically).

An embodiment or approach of the present invention provides a dual occlusion balloon to stop flow and create a sealed vessel section in which drug is injected, delivered and then flushed to eliminate systemic delivery concerns (requires second port well separated from first so as to permit flush in from one and vacuum out at other—i.e. ports upstream and downstream and close to each of the balloons)

An embodiment or approach of the present invention provides a 3D scanning to record extent of problem lesion followed by automated 3D sweep across the lesion to achieve therapeutic effect—i.e. it may be time/procedure efficient for the physician to outline the 3D extent of the plaque and then have the system sweep the region by way of automated sequence of ID lines to fully encompass the 2D surface of the 3D lesion. The "Track back" method, well known in IVUS, can be used "TrakBackII" from Volcano Corp for their array IVUS.

An embodiment or approach of the present invention provides a vulnerable plaque application as mentioned immediately above, except application is diagnosis of vulnerable plaque. (Further, it doesn't actually doesn't have to be 3D—but 3D is typically best). The means of differentiating vulnerable plaque comprises-any permutation of:
 a. Using appropriate molecular targeted microbubbles (VCAM-1 for example).
 b. Using microbubbles to detect microvasculature of vasa vasorum—an indicator of active vulnerable plaque (see for example, see reference Dutch group—Goertz, van der Steen et al.
   http://publishing.eur.nl/ir/repub/asset/7950/060908
   Frulink.%20Martǔn%20E gbert.pdf, Harmonic Intravascular Ultrasound Thesis, Martijn Frijlink, 2006 Delft, Netherlands).
 c. Performing signal processing (attenuation/frequency vs. depth as per "virtual histology" of Volcano (Vince et al.)
 d. Performing an elasticity based measurement to detect unusual softness of plaque (e.g., per known methods of transducer inside balloon described by M O'Donnell or measuring tissue response to pulsatile blood forces—A. F. W. van der Steen)
 e. "Tissue thermal strain imaging": Identification of vulnerable atherosclerotic plaque using IVUS-based thermal strain imaging: Yan Shi; Witte, R. S.; O'Donnell, M.; Ultrasonics, Ferroelectrics and Frequency Control, IEEE Transactions in Volume 52, Issue 5. May 2005 Page(s):844-850

An embodiment or approach of the present invention sets forth to stabilize the vulnerable plaque by delivery compounds such as basic Fibroblast growth factors (FGF) which promotes smooth muscle proliferation and migration to stabilize the weak fibrous cap. We will refer to all analogous therapy approaches for treating brain aneurysms with cerebral micro-coils. Micro-coils are delivered to the blood vessel wall where an aneurysm occurred to provide support for smooth muscle to proliferate and migrate and heal the aneurysm. An approach or embodiment promote, in the case, smooth muscle proliferation and migration, not inhibit it.

An embodiment or approach of the present invention provides a transducer(s) that may include any permutation of the following:
 a. Single element capable of any or all of: radiation force, imaging, bubble rupture.
 b. Phased array (in any format: longitudinal or annular) capable of any or all of: radiation force, imaging, bubble rupture.
 c. Either of the above wherein element(s) are dual (or triple) layer arranged to provide (typically) high power at lower frequency and lower power/fine resolution using high frequency.
 d. Wherein the different transducers performing different functions are not arranged one over the other. Place an elongated radiation force transducer (or array) upstream of imaging/delivery zone (see figure). Then have an imaging transducer—imaging the bubbles that have been pushed to the zone of interest. Then have a delivery transducer. (Subsets also possible—such as dedicated elongated radiation force transducer plus combined imaging/delivery transducer (or array).
 e. An embodiment or approach of the present invention provides a transducer(s) that can be formed from piezoelectric material (preferably ceramic but could be piezoelectric polymer PVDF). Alternatively transducers can be electrostatic, silicon (or other material) "MEMS" devices. An embodiment or approach of the present invention provides a method for localized delivery of drug from drug loaded microbubbles using high intensity ultrasound wherein the location of the focal delivery is guided by an integral, realtime, coincident, ultrasound imaging system.

An embodiment (or partial embodiment) or approach of the present invention provides a method for localized drug delivery wherein the drug coated bubbles possess a selected molecular attachment ligand—such as VCAM-1, P-Selectin, etc. under real time ultrasound image guidance, such as:
  dual targeting method—fast catch/slow hold
  variant on bubbles such as liposomes
  nanoparticle+bubble—dual modality contrast Ultrasound+MRI contrast Bubble+ferrous
  potential of drug not being integrated in bubble shell but existing in free solution aside the bubbles and relying on bubble related sonoporation to result in preferential drug uptake.

An embodiment or approach of the present invention provides a drug that is rapamycin (antiproliferative, immunosuppressive, or antiinflammatory drug, such as rapamycin, tacrolimus, paclitaxel, dexamethasone, or an active analog or derivative, or combinations thereof). The drug may be selected from a group comprising actinomycin-D, batimistat, c-myc antisense, dexamethasone, paclitaxel, taxanes, sirolimus, tacrolimus and everolimus, unfractionated heparin, low-molecular weight heparin, enoxaprin, bivalirudin, tyrosine kinase inhibitors, Gleevec, wortmannin, PDGF inhibitors, AG 1295, rho kinase inhibitors, Y27632, calcium channel blockers, TRAM-34, IKCa channel blockers, amlodipine, nifedipine, and ACE inhibitors, S1P1 and/or S1P3 receptor antagonists, sphingosine kinase 1 inhibitors, synthetic polysaccharides, ticlopinin, dipyridamole, clopidogrel, fondaparinux, streptokinase, urokinase, r-urokinase, r-prourokinase, rt-PA, APSAC, TNK-rt-PA, reteplase, alteplase, monteplase, lanoplase, pamiteplase, staphylokinase, abciximab, tirofiban, orboftban, xemilofiban, sibrafiban, roxifiban, an anti-restenosis agent, an anti-thrombogenic agent, an antibiotic, an anti-platelet agent, an anti-clotting agent, an anti-inflammatory agent, an anti-neoplastic agent, a chelating agent, penicillamine, triethylene tetramine dihydrochloride, EDTA, DMSA (succimer), deferoxamine mesylate, a radiocontrast agent, a radio-isotope, a prodrug, antibody fragments, antibodies, gene therapy agents, viral vectors and plasmid DNA vectors.

An embodiment or approach of the present invention provides a subset of relevant bubble properties—dimensions, core gas, shell materials, etc. and including oily shell—decafluorobutane.

An embodiment or approach of the present invention provides an acoustic radiation force that may be used to translate bubbles towards a selected vessel wall.

An embodiment or approach of the present invention provides microbubbles are targeted to blood vessels that routinely undergo and angioplasty and/or stenting (including balloon expansion stents and self-expanding stents), including but not limited to the coronary arteries, coronary artery branch points, carotid arteries, cerebral arteries, femoral arteries.

An embodiment or approach of the present invention provides a systemic injection of bubbles.

An embodiment or approach of the present invention provides a localized injection of bubbles—from catheter tip—preferably same catheter as imaging but potentially from separate one. See catheter cross-sectional drawing above.

An embodiment or approach of the present invention provides an ultrasound image guidance of bubbles in a highly bubble-specific mode using one of pulse inversion, amplitude scaling ("power modulation") or combination of two ("contrast pulse sequences").

An embodiment or approach of the present invention provides an ultrasound intensity has therapeutic (drug delivery) effect, wherein ultrasound has cell death effect.

An embodiment or approach of the present invention provides the uses of an ultrasound catheter—about 1-about 2 MHz therapeutic, about 30 MHz imaging.

An embodiment or approach of the present invention provides a co-located transducer—imaging device overlaying the therapeutic device, imaging device residing in an aperture formed within center of therapeutic device (less desirable than overlaying).

An embodiment or approach of the present invention provides a synchronized operation—the imaging system is "gated" to never operating during the time of therapeutic operation.

An embodiment or approach of the present invention provides a therapeutic system "listens" for imaging system operation and inserts therapeutic pulses between imaging operations.

An embodiment or approach of the present invention provides an imaging system "listens" for therapeutic system operation and inserts imaging pulses between therapeutic operations.

An embodiment or approach of the present invention provides a "Pulse sequence" claims—X seconds (s) of therapeutic, followed by Y s of imaging, and so on for Z minutes.

An embodiment or approach of the present invention provides an integrating of this device on a catheter with other preferred catheter device options—e.g. balloon, pressure measurement, temperature measurement, blood sampling.

An embodiment or approach of the present invention provides a catheter with "over the wire" capability—the standard—has capability to be "threaded" over an in-place metal wire.

An embodiment or approach of the present invention provides a catheter that may be a derivative of the "Volcano" IVUS catheter (phased annular array). A therapeutic transducer—side firing—is placed near to the imaging annular array.

An embodiment or approach of the present invention provides a catheter that may be related to some extent to the "Boston-Scientific" IVUS catheter (mechanically scanned single element) i.e. the existing high frequency transducer element is replaced with a stack of low frequency (therapeutic) 1 MHz element with 30 MHz imaging overlaid. Alternatively, there are two transducers side by side in close proximity.

An embodiment or approach of the present invention provides a catheter possessing an imaging transducer/array in any one or more of the following formats: single element transducer rotated in circumferential fashion to form coronal plane, circumferential array forming coronal plane, side-fire array and wherein the therapeutic array is in any one of more of the following formats: single element transducer rotated in circumferential fashion to form coronal plane, circumferential array forming coronal plane, side-fire array.

An embodiment or approach of the present invention provides an imaging transducer/array is in any one or more of the following formats: single element transducer rotated in annular fashion to form coronal plane, annular array forming coronal plane, side-fire array and wherein the therapeutic transducer is single focused element or annular array.

An embodiment or approach of the present invention provides a pro-proliferative for filling up an aneurysm, occlusive treatment upstream of an angiogenic region associated with evolving cancer; Image guidance other than ultrasound; or other mechanisms for therapeutic delivery—such as heat as opposed to acoustic disruption.

Wherein the image guidance (other than ultrasound) includes one or more of: X-ray and its derivatives (plain X-ray, realtime fluoroscopy and computed tomography [CT]), or 2) Magnetic Resonance Imaging (MRI).

An embodiment or approach of the present invention provides a complementary drug operation—two drugs in different bubble populations that are stable in isolation but upon ultrasound disruption mix and become active/unstable/therapeutic.

An embodiment or approach of the present invention provides a therapeutic ultrasound plus bubble, drug and stent—wherein ultrasound induces vibrational mode/activity within stent so as to elicit therapeutic effect among cells/drugs/bubbles adjacent to stent surface.

An embodiment or approach of the present invention provides a different types of stent and different generations of stent—bare metal stent, current DES, dissolving polymer stent, non-polymer stent.

An embodiment or approach of the present invention provides an acoustic signature of stent that may be monitored to determine degree of accumulation of stiff acoustic loading on stent and any change resulting from therapeutic effect.

An embodiment or approach of the present invention provides microbubbles that are delivered to a vascular aneurism to deliver a drug that promotes smooth muscle migration and proliferation to heal the aneurism. Drugs include but are not limited to PDGF-BB, bFGF, etc.

An embodiment or approach of the present invention provides a method for localized drug delivery wherein the drug-carrying bubbles possess a selected molecular attachment ligand—such as VCAM-1, P-Selectin, etc. under real time ultrasound image guidance including any permutation thereof: dual targeting method—fast catch/slow hold [99]; microbubble composition, such that a plurality of targeting ligands capable of binding with the diseased tissue, some of the ligands capable of binding rapidly, and others binding firmly, are attached to the microbubbles; variant on bubbles such as liposomes nanoparticle+bubble—Microbubble composition, having liposomes or biocompatible nanoparticles applied to the microbubble shell to house the drug compounds to be released by targeted insonation; dual modality contrast Ultrasound+MRI contrast Bubble+ferrous (or in another disclosure); potential of drug not being integrated in bubble shell but existing in free solution aside the bubbles and relying on bubble related sonoporation to result in preferential drug uptake.

An embodiment or approach of the present invention provides a drug that may be rapamycin (antiproliferative, immunosuppressive, or anti-inflammatory drug, such as rapamycin, tacrolimus, paclitaxel, dexamethasone, or an active analog or derivative, or combinations thereof).

An embodiment or approach of the present invention provides a subset of relevant bubble properties—dimensions, core gas, shell materials, etc.

An embodiment or approach of the present invention provides a microbubble composition having drug incorporated, situated, dispersed, dissolved therein directly in the shell, core or core multiplicity, or attached to the outside of the shell, having shell(s) comprised with lipids, phospholipids, oils, fats, lipopolymers, polymers, proteins, surfactants or combinations thereof, shell thickness varied from monomolecular 1 nm, to multimolecular and multilamellar, up to and including 1000 nm.

An embodiment or approach of the present invention provides microbubble compositions having internal core filled with the gas, gas-vapor mixture or gas precursor phase, gas having molecular mass from about 10 to about 360.

An embodiment or approach of the present invention provides a microbubble compositions having decafluorobutane core.

An embodiment or approach of the present invention provides an acoustic radiation force is used to translate bubbles towards a selected vessel wall, or other organs or tissues as desired.

An embodiment or approach of the present invention provides an application in the coronary artery, application in other vessels, or other organs or tissues as desired. An embodiment or approach of the present invention provides a systemic injection of bubbles.

An embodiment or approach of the present invention provides a localized injection of bubbles—from catheter tip—preferably same catheter as imaging but potentially from separate one. See catheter cross-sectional drawing above.

An embodiment or approach of the present invention provides an ultrasound image guidance of bubbles in a highly bubble-specific mode using one of pulse inversion, amplitude scaling ("power modulation") or combination of two ("contrast pulse sequences"): wherein ultrasound intensity has therapeutic (drug delivery) effect; and/or wherein ultrasound has cell death effect. An embodiment or approach of the present invention provides an ultrasound catheter—1-2 MHz therapeutic, 30 MHz imaging.

An embodiment or approach of the present invention provides a co-located transducer—imaging device overlaying the therapeutic device, imaging device residing in an aperture formed within center of therapeutic device (which may be less desirable than overlaying).

An embodiment or approach of the present invention provides a synchronized operation—the imaging system is "gated" to never operate during the time of therapeutic operation: wherein the therapeutic system "listens" for imaging system operation and inserts therapeutic pulses between imaging operations, and/or wherein the imaging system "listens" for therapeutic system operation and inserts imaging pulses between therapeutic operations.

An embodiment or approach of the present invention provides a "Pulse sequence" claims—X seconds (s) of therapeutic, followed by Y s of imaging, and so on for Z minutes (time, repetition, cycles and duration as desired or required).

An embodiment or approach of the present invention provides an integrating of this device on a catheter with other preferred catheter device options—e.g. balloon, pressure measurement, temperature measurement, blood sampling.

An embodiment or approach of the present invention provides a catheter with "over the wire" capability—the standard—has capability to be "threaded" over an in-place metal wire.

An embodiment or approach of the present invention provides a catheter that is a derivative of the "Volcano" IVUS catheter (phased annular array). A therapeutic transducer—side firing—is placed near to the imaging annular array.

An embodiment or approach of the present invention provides a catheter that is a derivative of the "Boston-Scientific" IVUS catheter (mechanically scanned single element) i.e. the existing high frequency transducer element is replaced with a stack of low frequency (therapeutic) about 1 MHz element with about 30 MHz imaging overlaid. Alternatively, there are two transducers side by side in close proximity. Frequency may vary as desired or required.

Figures 20A, 20B:
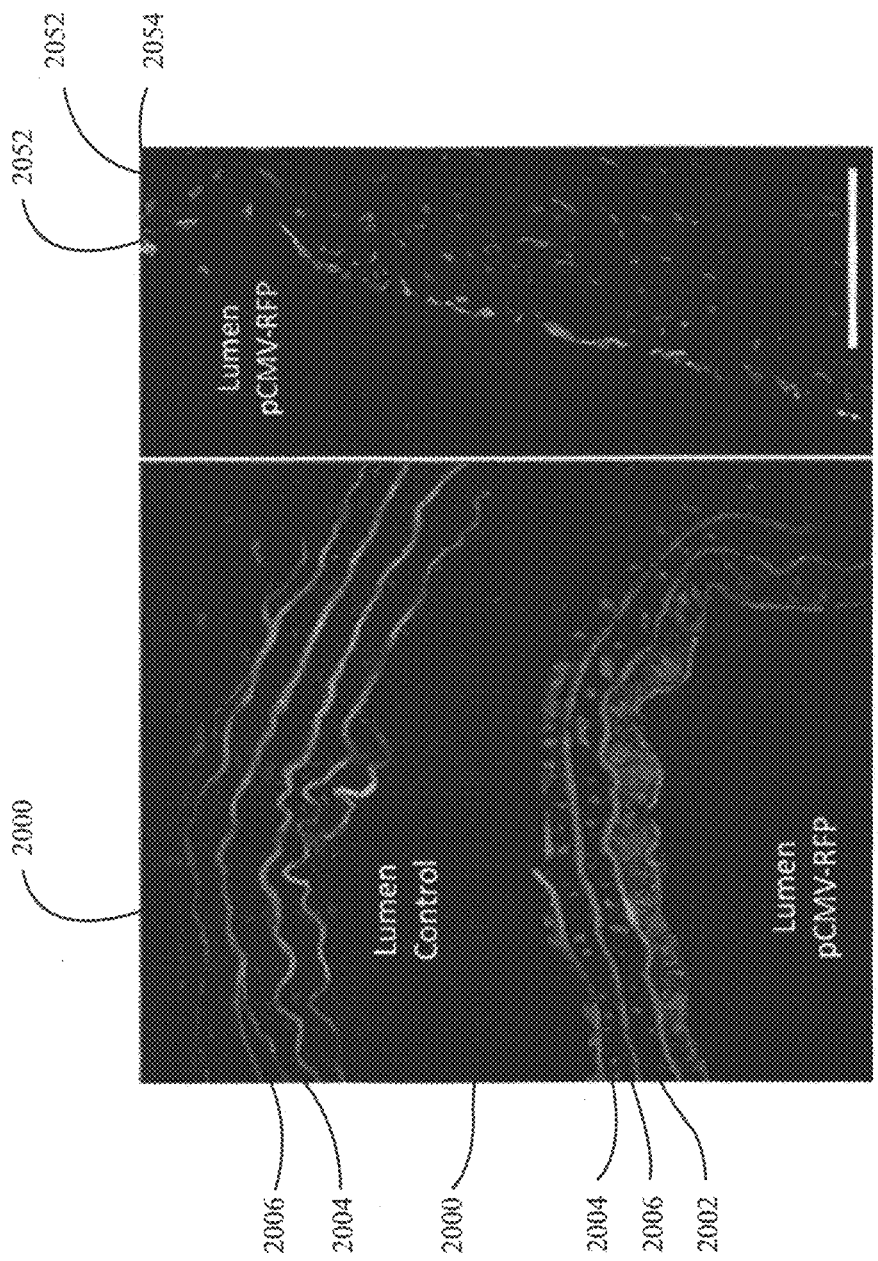
FIG. 20A shows RFP expression (red) in a pig's left common carotid artery three days following ultrasound application according to an embodiment of the present invention.
FIG. 20B shows results from use of a modified intravascular ultrasound catheter (IVUS) on a pig's coronary artery (LAD) according to an embodiment of the present invention.

An embodiment of the present invention provides a device and related method for delivering therapeutic compounds or DNA molecules to blood vessel walls using microbubble carriers and focused ultrasound. It has been demonstrated that plasmid DNA, or drug, can be conjugated to microbubbles and delivered to a pig's left common carotid artery 2000 (FIG. 20A) as well as a pig's left anterior descending (LAD) coronary artery 2050 (FIG. 20B) in vivo using focused ultrasound according to techniques described herein. FIGS. 20A-20B show results of delivery of plasmid DNA expressing red fluorescent protein (RFP) to blood vessels in vivo under constant flow by ultrasound and microbubbles. Preparation of the microbubbles involved conjugation of p-Cytomegalovirus (pCMV-RFP) to positively charged microbubbles having dimensions of about 2.0 micron outside diameter. The pCMV-RFP conjugated microbubbles were injected intravenously and focused, transcutaneous ultrasound was applied to the left common carotid of artery (FIG. 20A) or the LAD (FIG. 20B) to insonate microbubbles and deliver the DNA plasmid to the blood vessel wall. FIG. 20A shows RFP expression 2002 (red) in a pig's left common carotid artery three days following ultrasound application; the blue 2004 represented DAPI, nuclei; the green 2006 shows the elastic lamina of the artery. FIG. 20B shows results from use of a modified intravascular ultrasound catheter (IVUS) as described herein, on a pig's coronary artery (LAD). The pCMV-RFP was delivered to the endothelium of a pig coronary artery under constant flow. The image in FIG. 20B shows RFP expression 2051 (red) three days following treatment; the blue 2054 shows nuclei. FIG. 20C is a bar chart that illustrates the percentage of cells that were observed to fluoresce due to the DNA plasmid having been delivered thereto, with and without the use of the modified IVUS catheter as described above, in pig coronary arteries.

The above methods and devices allow researchers to deliver DNA molecules or novel drug compounds specifically to a blood vessel in an animal for pre-clinical efficacy studies. Further, a purpose of an embodiment of the device and related method is to advance the use of RNAi delivery to blood vessels. RNAi (shRNA and miRNA) offers the unprecedented ability to selectively knockdown a gene of interest in a cell. There are multiple biotechnology and pharmaceutical companies developing programs around RNAi therapy. A major challenge for these companies and academia is the ability to actually deliver the RNAi therapy to a blood vessel in vivo. Aside from the clinical application of this technology, enablement of RNAi delivery will also allow scientists to selectively knockdown gene expression in blood vessels in mice, for example, circumventing the extremely costly and often confounding results associated with mouse gene deletion studies.

The present invention provides a tool for clinical therapy and rapid, cost-effective, target loss-of-function validation studies in animals. Moreover, an embodiment of the device and related method will have application in other disease areas, such as cancer, etc. Further, the present invention may use formulations to test new chemical entities (NCEs) that are proposed to reduce atherosclerosis/inflammation in the blood vessel wall.

At least one embodiment of the present invention may be related to *Molecular Targeted Ultrasound-Based Delivery of Antiproliferative Drugs to Treat Restenosis*; See PCT International Application No. PCT/US2008/081189, Hossack, et al., entitled "System for Treatment and Imaging Using Ultrasonic Energy and Microbubbles and Related Method thereof," filed Oct. 24, 2008, which claims priority from U.S. Provisional Application Ser. No. 61/000,632, filed Oct. 26, 2007, entitled "Molecular Targeted Microbubbles for Enhanced Blood Vessel Imaging and Therapeutic Treatment of Neointimal Hyperplasia," and U.S. Provisional Application Ser. No. 61/099,025, filed Sep. 22, 2008, entitled "Molecular Targeted Microbubbles for Enhanced Blood Vessel Imaging and Therapeutic Treatment of Neointimal Hyperplasia;" of which all of the disclosures are hereby incorporated by reference herein in their entireties. DNA molecule delivery is an aspect of at least one embodiment of the present invention.

RNAi (shRNA and miRNA) offers the unprecedented ability to selectively target specific mRNA transcripts and thus regulate protein expression in a cell. The promise for RNAi therapy to treat cancer, neurological disorders, cardiac, and vascular disorders continues to grow and several biotech companies have raised millions of dollars to bring this to the patient. Delivery of RNAi therapeutics to a blood vessel, however, is not trivial and blood flow poses a major roadblock.

An aspect of an embodiment of the present invention is to deliver DNA molecules to blood vessel walls in vivo under constant flow. An embodiment of the present invention may utilize, for example, FDA-approved contrast agents called microbubbles as a vehicle for delivery of an agent (drug, DNA molecule, small molecule) to a target using ultrasound-mediated insonation.

As noted above, an embodiment of the present invention includes the delivery of RNAi to blood vessels in mice, pigs or other animals, as well as humans. This delivery may be of specific RNAi molecules for the treatment of vascular disorders in humans. Such delivery may be of RNAi in animals for pre-clinical target loss-of-function validation studies, potentially circumventing the costly and often confusing results associated with gene knockout studies in mice.

A target for a proof-of-concept study includes the β-galactosidase gene or lacZ expressed in the ROSA26 mouse. The ROSA26 mouse has been genetically engineered to have widespread lacZ expression in many cell types, including uniform expression in hematopoietic cells (macrophages) and endothelial cells and smooth muscle cells of large arteries in the ApoE or L1d-R deficient mouse models of atherosclerosis. (Zambrowicz et al., 1997). Here forward this mouse and cells from this mouse are referred to as "ROSA26".

Validation of the concept is viewed as the ability of miR-lacZ to decrease lacZ gene expression in vitro and in vivo in ROSA26 mouse vascular cells. The BLOCK-iT™ Pol II miR Validated miRNA Vector will be utilized. This includes a highly effective, functionally tested pcDNA™6.2-GW/EmGFP-miR Validated miR-LacZ insert, which encodes a 68 bp engineered pre-miRNA sequence targeting lacZ. This plasmid is referred to as"p-miR-lacZ".

ROSA26 mouse aortic endothelial and smooth muscle cells will be used to validate whether focused ultrasound delivery of p-miR-lacZ via microbubble insonation reduces lacZ expression in cell culture, which is the first objective of the study. As shown in FIGS. 21A-21C, delivery of rapamycin (Sirolimus) via microbubbles in vitro to smooth muscle cells only prevents proliferation 2100 where the ultrasound is applied. Changing the width of the ultrasound beam profile focuses the therapeutic effect rapamycin delivered to smooth muscle cells via microbubbles in vitro. In FIGS. 21A-21C, the left y-axis denotes proliferation 2100, while the right y-axis denotes beam profile. The X-axis denotes beam width 2102. Cells were cultured for twenty-four hours in 10% serum following rapamycin delivery. The use of microbubbles alone (without any attachment, conjugation or containment of drug) did not effect proliferation.

Thus, it has been confirmed in an in vitro model that ultrasound alone, or ultrasound plus microbubbles with no drug, do not effect cell proliferation. Thus, the readout for reduction in lacZ will be colorimetric analysis for a reduction of blue cells using the lacZ substrate, X-gal (Sigma). p-miR-lacZ is designed such that eGFP is co-expressed which will allow us to confirm that a reduction in lacZ is synonymous with eGFP fluorescence. This is very similar to our analysis of pCMV-RFP delivery to vascular cells by microbubbles and ultrasound in vitro using fluorescence microscopy to detect RFP expression, described above, with results shown in FIGS. 20A-20B. After refining bubble/plasmid parameters for maximum knockdown of lacZ in vitro, we will utilize this formulation to determine whether p-miR-lacZ delivery to a blood vessel in vivo by ultrasound-mediated insonation of microbubbles decreases vascular cell expression of lacZ in the ROSA26 mouse. This will be assessed by cross-sectional histology and X-gal staining coupled to eGFP detection by immunhistochemistry or fluorescence microscopy (similar to techniques us to produce FIGS. 20A-20B).

In at least one embodiment of the present invention, blood samples may be taken prior to and following insonation of microbubbles. These blood samples can be used for analysis to determine whether the rheology of the blood has been altered during the insonation procedure.

The miR Expression Vector—pcDNA™6.2-GW/EmGFP-miR-lacZ or p-miR-lacZ:

For optimal lacZ knockdown results, the following structural features were incorporated in the ds oligo encoding the engineered pre-miRNA for lacZ: 1) 4 nucleotide, 5' overhang (TGCT) complementary to the vector (required for directional cloning), 2) 5'G+short 21 nucleotide antisense sequence (mature miRNA) derived for lacZ (GACTACA-CAAATCAGCGATTT) (SEQ ID NO: 1 SEQ ID NO: 1) followed by 3) a short spacer of 19 nucleotides to form the terminal loop and 4) a short sense target sequence with 2 nucleotides removed ($\Delta 2$) to create an internal loop, 5) a 4 nucleotide, 5' overhang (CAGG) complementary to the vector (required for directional cloning). The vector is designed with unique restriction enzyme sites to replace miR-lacZ with a desired miRNA for future gene target validation studies in vivo using the technology of the present invention as described herein.

Microbubble Chemistry

Figure 22:
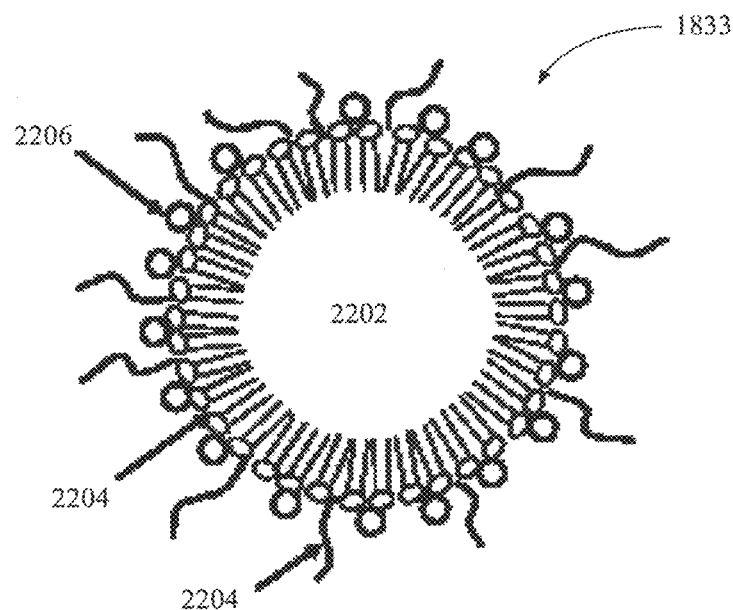
FIG. 22 is a schematic illustration of a microbubble according to an embodiment of the present invention.

Cationic lipid microbubbles are formed by self-assembly. Briefly, an aqueous micellar mixture of phosphatidylcholine, polyethylene glycol-40 (PEG) stearate, used to extend in vivo lifetime, and distearyl trimethylammonium propane are sonicated while sparging decafluorobutane gas. Microbubbles are separated from unreacted components by centrifugal flotation. Microbubble size and concentration are measured by electrozone sensing on a Coulter counter. p-miR-lacZ plasmids are combined with the cationic lipid-shelled microbubbles by electrostatic charge coupling as previously demonstrated and coupling efficiency is assessed as compared to the neutral or anionic microbubbles. The amount of plasmid coupled to the microbubbles is calculated by absorbance at 260 nm and against a standard curve. The p-miR-lacZ to microbubble ratio for experiments is maintained at 1 µg DNA/$5 \times 10^6$ microbubbles. FIG. 22 illustrates one embodiment of a microbubble 1833 having a decafluorobutane gas core 2202, a cationic lipid shell 2204, with plasmid DNA 2206 and PEG spacers 2208 attached thereto.

In at least one embodiment of the present invention, ultrasound-mediated insonation of p-miR-lacZ-conjugated microbubbles are provided to a blood vessel, in accordance with techniques and devices described herein, to reduce lacZ expression in ROSA26 endothelial and smooth muscle cells in vitro. As the gene database of miRNAs continues to grow, so does the promise for novel therapies that deliver sense or anti-sense miRNAs. Delivery of RNAi (shRNA, sense- or anti-sense miRNA) is a major challenge for this field, particularly in the vasculature. Focused ultrasound can be utilized to deliver RNAi to specific cells for gene knockdown in vitro using microbubble carriers.

Figure 23:
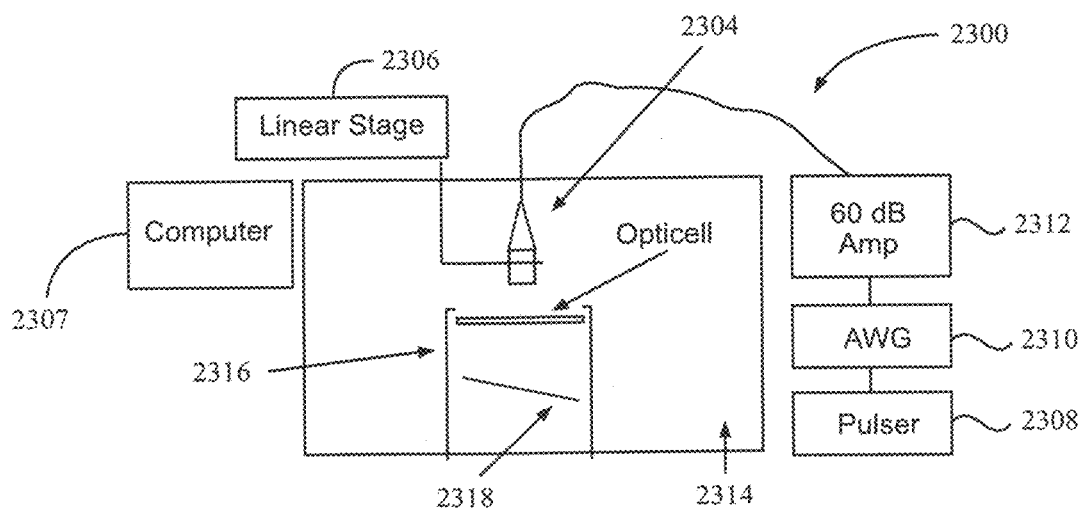
FIG. 23 schematically illustrates a system for an in vitro procedure according to an embodiment of the present invention.

Experimental Approach:

lacZ expressing endothelial and smooth muscle cell lines will be cultured from ROSA26 mouse aorta as routinely performed by our lab. Cells are plated in an optically transparent and acoustically penetrable OPTICELL™ 2302. Twenty-four hours after cells are plated, the media in each OPTICELL™ 2302 is replaced with fresh media containing one of the following three combinations of reagents: microbubbles ($1.5 \times 10^8$) coupled with 30 µg of the p-miR-lacZ plasmid (final solution in each OPTICELL™—3 µg/ml), 30 µg p-miR-lacZ plasmid alone (no microbubbles), or equivalent volume of pure saline (no plasmid or microbubbles). The insonation apparatus 2300 shown in FIG. 23 includes the use of a single-element, focused 1 MHz transducer 2304 (Panametrics) and a MM3000 motion controller linear stage 2306 to precisely position it. A set of waveforms, pulse repetition frequencies, and amplitudes are chosen to maintain a constant duty cycle, using automatic wave generator (AWG) 2310, pulser 2308 and amplifier 2312, while varying the individual pulse lengths and peak pressures. Each OPTICELL™ 2302 is held in an OPTICELL™ holder 2316 backed by an acoustic absorber 2318 and immersed for two minutes in a water bath 2314 held at 37° C. using a recirculating heater (not shown) (Model 73A0A11B, Polyscience, Niles, Ill.) before insonation in order to allow time for the bubbles to rise toward the cells. Following insonation, OPTICELLs™ 2302 are immediately flushed with phosphate buffered saline (PBS) and replenished with fresh serum-containing growth media. p-miR-lacZ transfection efficacy is measured 24 hours after treatment as the number of eGFP fluorescent cells per unit area. Knockdown of LacZ is assessed seventy-two hours after treatment by fixing the cells and processing for lacZ signal using X-gal. Efficacy of lacZ suppression is determined by quantifying the intensity of lacZ in non-eGFP cells compared to eGFP positive cells. Cell death and proliferation is analyzed by BrdU incorporation and TUNEL or Annexin V staining.

One aspect of the present invention is directed toward optimizing microbubble formulations. For instance an embodiment provides a methodology for pCMV-RFP transfection and rapamycin delivery by microbubbles 1833 to smooth muscle cells (SMCs) to prevent smooth muscle cell proliferation. An alternative to ROSA26 cells is using mice genetically engineered to overexpress eGFP (ROSA26eGFP; mouse lines we have used before for bone marrow transplants). This approach would involve p-miR-eGFP which co-expresses RFP to identify transfected cells. This would be viewed as a "stoplight" approach, wherein a result of eGFP+ cells (indicated by green, not red) means that no transfection/no knockdown has occurred, as compared to a result of RFP+ cells (indicated by red, not green), which means that p-miR-eGFP transfection has occurred and eGFP knockdown has occurred. The same approach can be applied in vivo.

Figure 24:
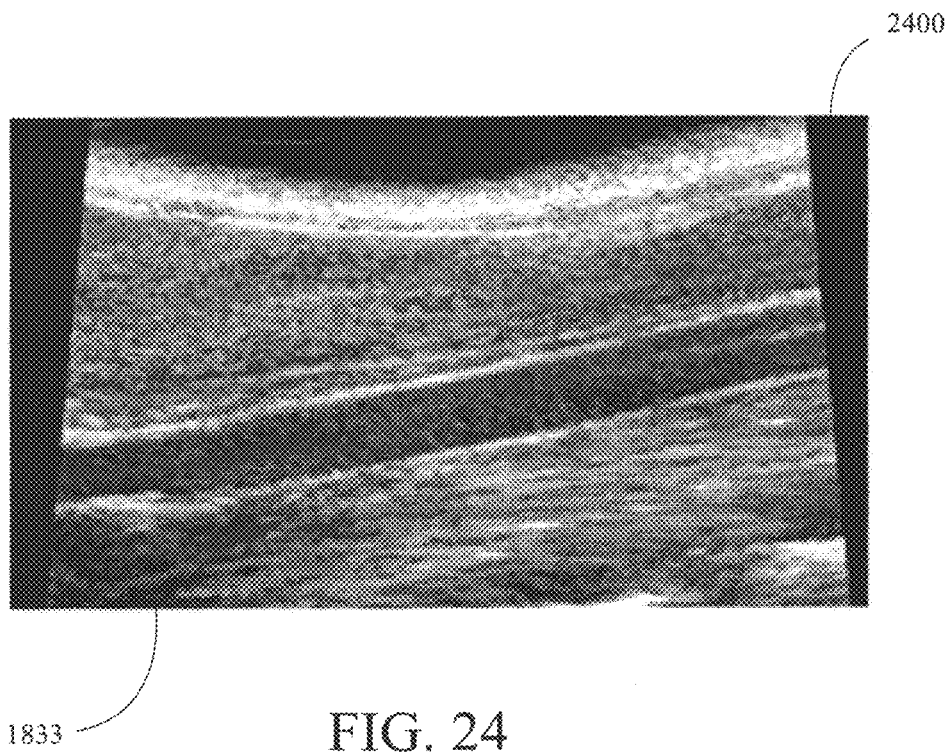
FIG. 24 is an ultrasonic image of a left carotid artery in a ROSA26 mouse, imaged according to an embodiment of the present invention.

In at least one embodiment, the present invention includes ultrasound-mediated insonation of p-miR-lacZ-conjugated microbubbles that reduces lacZ expression in ROSA26 endothelial and smooth muscle cells in vivo under blood flow. As the gene database of miRNAs continues to grow, so does the promise for novel therapies that deliver sense or anti-sense miRNAs. Delivery of RNAi (shRNA, sense- or anti-sense miRNA) is a major challenge for this field, particularly in the vasculature. Focused transcutaneous ultrasound can be utilized to deliver p-miR-lacZ to carotid artery endothelial and smooth muscle cells in ROSA26 mouse intact arteries in vivo using microbubble carriers to knockdown lacZ expression. The left carotid artery 2400 in a ROSA26 mouse is located non-invasively (FIG. 24) using ultrasound imaging in order to position the face of a Sequoia (Siemens) transducer parallel to the artery. A mixture of the p-miR-lacZ microbubbles 1833 is infused at a rate of about $2 \times 10^7$ microbubbles/min for a total of about 5 minutes. Initially, based on studies in delivery of pCMV-RFP to rat carotid arteries, ultrasound (~5 MHz, PNP=0.6 MPa) is applied in contrast pulse sequencing (CPS) burst mode to the left carotid in one second bursts every two seconds for the full five minute microbubble infusion. The right carotid, through which microbubbles also flow, but which is not insonated, serves as a treatment control. Three days after p-miR-lacZ delivery, the animal is euthanized and left and right carotids are processed for frozen histological cross sectioning.

Two approaches are taken to determine lacZ knockdown. First, immunofluoresence microscopy is used to detect lacZ using a lacZ primary antibody and Alexa-568 (red) conjugated secondary antibody is performed. This signal is co-localized to eGFP positive cells (488 nm) to confirm p-miR-lacZ transfection in each cell analyzed. Second, adjacent sections are stained for lacZ using X-gal and percent blue cells determined per cross-sectional area. Cell death and proliferation in eGFP positive cells are analyzed by BrdU incorporation (injection prior to euthanizing) and TUNEL or Annexin V staining using confocal microscopy.

Another embodiment of the present invention includes delivery of p-miR-lacZ to endothelial cells and the first layer of vascular smooth muscle cells in the mouse carotid artery. This has already been accomplished in rats and swine according to the present invention as noted above. To increase penetration, a large widow of parameters can be altered, including: frequency (MHz), peak pressure (MPa), pulse cycle length (N) and pulse repetition rate (Hz). Traditionally, parameter response curves developed in our in vitro models have guided trouble-shooting and our ability to increase efficacy in vivo, thus reducing parameter search space and costly animal studies. As stated above, an embodiment can also use the ROSA26eGFP mouse and p-miR-eGFP. Still further, ROSA26 (lacZ or eGFP) may be crossed onto the ApoE−/− background to determine whether we can deliver RNAi into complex lesions. Although mice do not have an active vasovasorum in a healthy vessel, ApoE−/− mice do develop a vasovasorum which will assist in delivery of microbubbles to the plaque.

In another embodiment, the present invention provides systems and method for image guided diagnosis and therapy including: using an appropriately molecular targeted (e.g. VCAM-1) drug charged microbubble 1833 that selectively adheres to a lesion based on molecular markers for disease (as opposed to relying on visual interpretation of late stage anatomically detectable adaptations in response to underlying disease—i.e. vessel wall remodeling, asymmetric lesion formation etc.). VCAM-1 is used here simply as an example. Other targets are feasible according to the lesion of interest. For example alphaVbetaIII is a target commonly used in the context of cancer. Examples of molecular targeted contrast agent design and fabrication are found in the literature: e.g., regarding VCAM-1, see Kaufmann et al., "Molecular imaging of inflammation in atherosclerosis with targeted ultrasound detection of vascular cell adhesion molecule-1", Circulation, vol. 116, pp. 276-84, 2007; regarding P-Selectin, see Kaufmann et al., "Detection of recent myocardial ischaemia by molecular imaging of P-selectin with targeted contrast echocardiograph.", Eur. Hear J., vol. 16, pp. 2011-2017, 2007; and regarding alphaVbetaIII, see Dayton et al., "Ultrasonice Analysis of Peptide- and Antibody-Targeted Microbubble Contrast Agents for Molecular Imaging of AVB3-Expressing Cells", Molecular Imaging, vol. 3, pp. 125-134, 2004, each of which publications are hereby incorporated herein, in their entireties, by reference thereto. Dayton et al. also discusses different types of targeting chemistry—i.e. peptide-based and antibody-based. Peptide-based targeting is generally perceived as a preferred, but more complex in practice, approach that is more likely to be clinically adopted than an antibody-based approach. In any event, the scope of the current invention encompasses all manner of molecular targets and all manner of surface binding chemistries.

Figure 26:
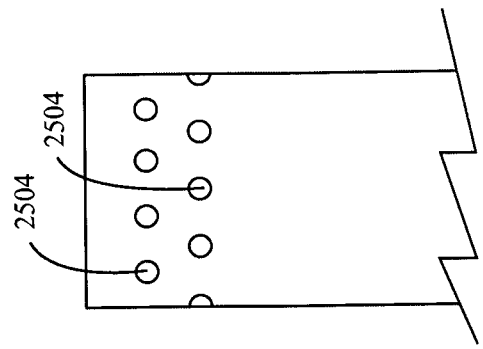
FIG. 26 schematically illustrates a planar view of a distal end portion of a catheter according to another embodiment of the present invention.
Figure 25B:
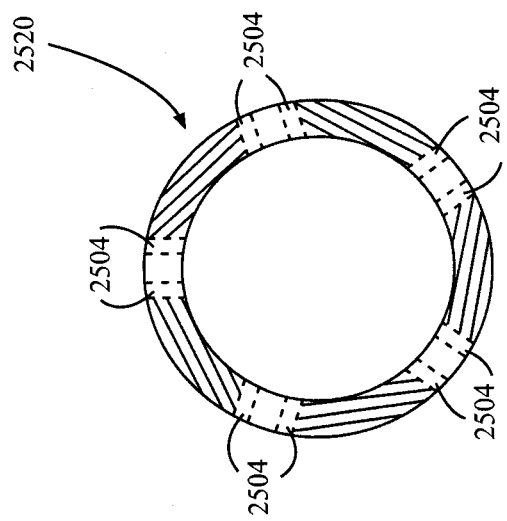
FIGS. 25A-25B schematically illustrate a planar view of a distal end portion of a catheter (FIG. 25A) and a cross-sectional view (FIG. 25B) taken at line 25B-25B in FIG. 25A, according to an embodiment of the present invention.
Figure 25A:
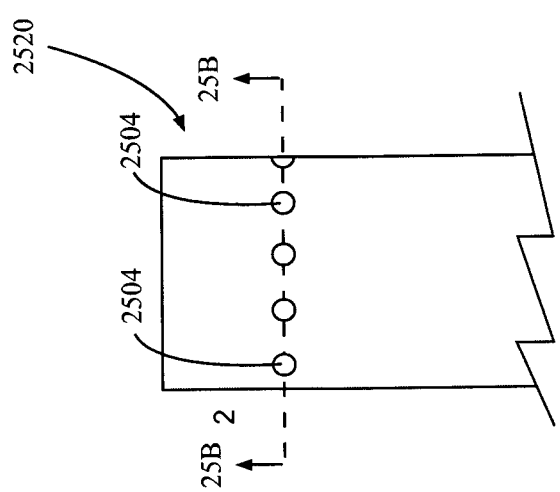

The targeted microbubbles 1833 are flowed over the suspected lesion region. Generally, the bubbles are dispensed from a port, or ports, that provide exit(s) from a lumen(s) that runs the length of the catheter 1420, 1820, 1920, 2520, 2620, etc. being used. There may be multiple ports 2504 arranged circumferentially in a ring as illustrated in catheter 2520 in FIGS. 25A-25B, or sets of offset rings of ports 2604, as illustrated in catheter 2620 in FIG. 26, so as to direct microbubbles 1833 across the entire vessel wall. The catheter may be translated and rotated to provide complete lesion coverage. The translating and rotation may be via manual (physician directed) manipulation of the proximal end of the catheter or via a motion stage capable of translating and twisting the catheter. Translating motion stages are widely used in current IVUS. One example is the Volcano Therapeutics TrakBackII that comprises of a battery powered box that has, as a user control, a three way switch, Off, 0 5 mm/s and 1.0 mm/s, for example.

The microbubbles 1833, after ejection from the catheter are subjected to acoustic radiation force from the ultrasound transducer (or transducers) 1412, 1812 in the IVUS catheter 1420, 1820, 1920, 2520, 2620. Discussion of role of radiation force for enhancing molecular targeting efficiency is described in further detail, for example, in Rychak et al., "Acoustic Radiation Force Enhances Targeted Delivery of Ultrasound Contrast Microbubbles" In vitro Verification", IEEE Transactions on Ultrasonics Ferroelectrics & Frequency Control, vol. 52, pp. 421-433, 2005; and Rychak et al., "Enhanced Targeting of Ultrasound Contrast Agents Using Acoustic Radiation Force", Ultrasound in Medicine & Biology, vol. 33, pp. 1132-1139, 2007, both of which publications are hereby incorporated herein, in their entireties, by reference thereto.

Preferrably the acoustic radiation force is applied throughout the region of interest. Using an IVUS transducer makes this convenient since the transducer (or array) is directed to provide complete circumferential coverage. Vessel lumen axial coverage may be provided by manually inserting or withdrawing the catheter or by mechanised approach such as the TrakBackII device referred to above.

Additionally, IVUS imaging may be used to examine the scope of lesion using the adhered microbubbles as a marker defining the extent of the lesion.

The IVUS catheter may be operated to provide for a bubble specific imaging mode of operation such as the well known pulse inversion or amplitude modulation methods (or combinations thereof). However, since microbubbles provide such a strong reflection independent of mode of operation, it is likely that degree of microbubble coverage over a lesion region will be readily evident in conventional IVUS imaging modes (i.e. conventional B-Mode fundamental modes of operation). In the context of IVUS frequencies, considerable interest has also been focused on the potential of subharmonic modes of imaging because subharmonics provide for high bubble specificity and the frequencies generated in subharmonic modes of operation at IVUS frequencies (20-60 MHz transmitted) are less burdensome to detect from an instrumentation viewpoint, as noted in Goertz et al., "High Frequency Nonlinear B-Scan Imaging of Microbubble Contrast Agents", IEEE Trans. Ultrasonics, Ferroelectrics and Frequency Control, vol. 52, pp. 154-155 (1-3), 2005, which is hereby incorporated herein, in its entirety, by reference thereto. Once the microbubbles 1833 are allowed to accumulate using some optimized protocol (such as allowing microbubbles to accumulate for, a predetermined time such as, but not limited to the example of five minutes), an imaging scan is made to determine the extent (i.e., dimensions, such as length and width and/or depth, or diameter) of the lesion. Using IVUS imaging, molecular targeted imaging results may be viewed in the context of B-Mode imaging of vessel wall composition underneath the vessel lumen surface. This information, taken together, will guide the physician's choice of therapy.

Once the extent of the lesion has been assessed, the catheter system may be switched to burst mode to break the micorbubbles 1833 via insonation and effect drug delivery. The catheter system is switched to a high output intensity mode of operation to break the microbubbles 1833 and provide for drug or gene delivery. The high power ultrasound may be produced by an imaging transducer if the transducer is capable of the required intensity level (200 kPa+) or by a modified IVUS—as per the previous disclosures. For example, the "therapy" or "bursting" transducer may be offset from the "imaging" transducer or made coincident by placing one transducer over the other. Generally, having a coincident imaging and therapy/bursting transducer is preferable. The transducer(s) may be conventional PZT ceramic or silicon-based MEMS transducer or any other form of ultrasound creating transducer.

In therapeutic/bursting mode, the ultrasound is swept around axially and circumferentially to achieve complete coverage of the lesion with its attached microbubbles. As noted above, this may be achieved using a circumeferentially oriented IVUS format in combination with axial translation using a TrakBackII or similar.

Next, the catheter system is switched back to imaging mode to verify complete delivery—i.e. that all adhered microbubbles 1833 have been eliminated by bursting them, and that complete coverage is verifiably effected.

Once it is believed that complete therapeutic coverage has been achieved, the catheter system is switched back to imaging mode and the entire lesion field examined to verify that all microbubbles have been broken. As before, a microbubble specific imaging mode may be preferred, but is not essential.

In the cases where a region or regions is/are found where microbubbles persist (i.e., not all microbubbles have been burst, which indicates a lack of drug/gene delivery to that region or regions), repetion of the bursting and imaging validation steps can be interated until it is conclusively shown that coverage has been satisfactorily achieved.

Figure 27:
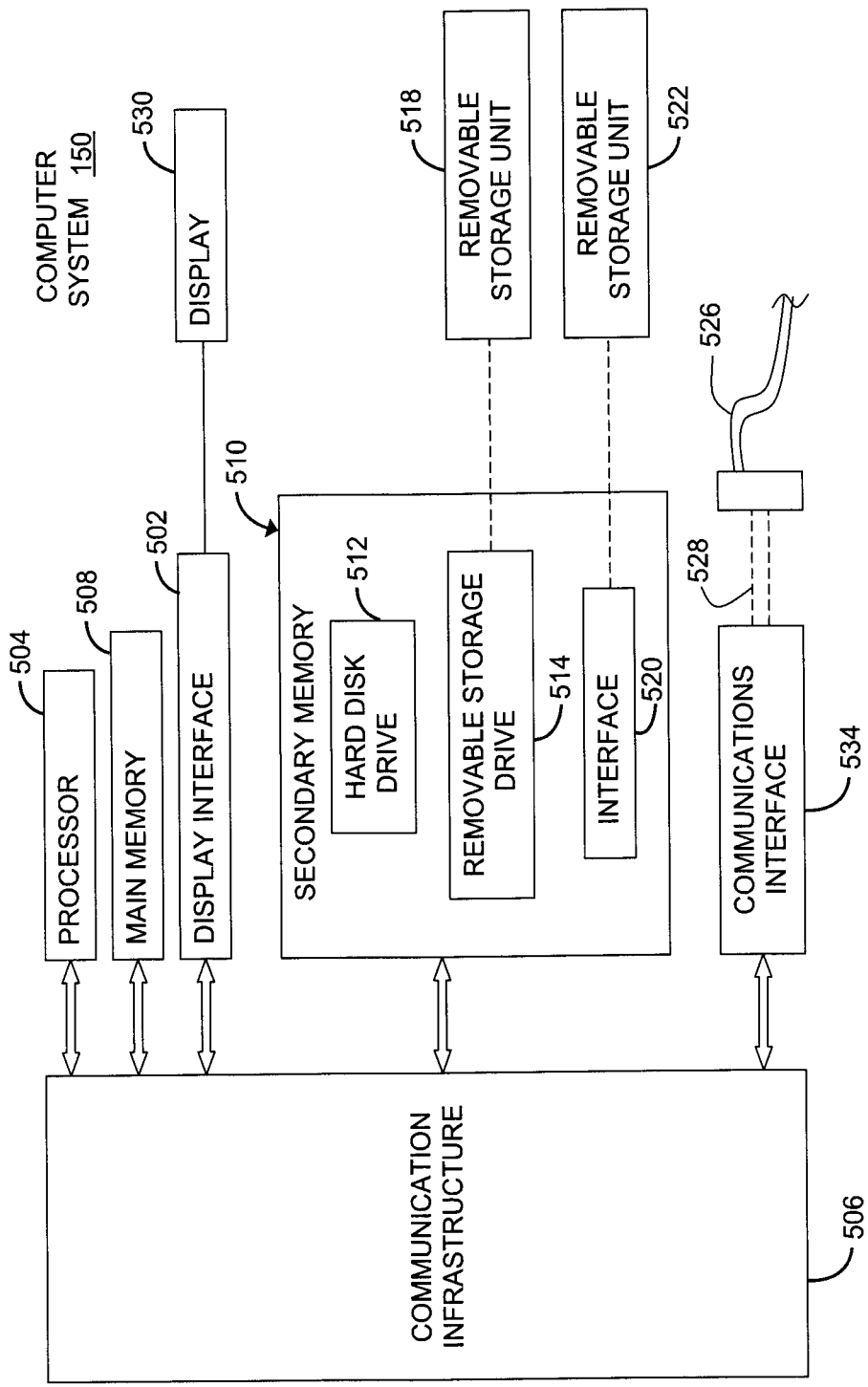
FIG. 27 is a schematic block diagram for a computer system for implementation of an exemplary embodiment or portion of an embodiment of the present invention.

FIG. 27 is a schematic block diagram for a computer system 150 for implementation of an exemplary embodiment or portion of an embodiment of the present invention. For example, a method or system of an embodiment of the present invention may be implemented using hardware, software or a combination thereof and may be implemented in one or more computer systems or other processing systems, such as personal digit assistants (PDAs) equipped with adequate memory and processing capabilities. All or a portion of computer system 150 may be used for control circuitry 200, controller 1800, and/or computer 2307, for example. In these and other embodiments, the computer system 150 may include one or more processors, such as processor 504. Processor 504 is connected to a communication infrastructure 506 (e.g., a communications bus, crossover bar, or network). The computer system 150 may include a display interface 502 that forwards graphics, text, and/or other data from the communication infrastructure 506 (or from a frame buffer not shown) for display on the display unit 530. Display unit 530, when present, may be digital and/or analog.

The computer system 150 may also include a main memory 508, preferably random access memory (RAM), and may also include a secondary memory 510. The secondary memory 510 may include, for example, a hard disk drive 512 and/or a removable storage drive 514, representing a floppy disk drive, a magnetic tape drive, an optical disk drive, a flash memory, etc. The removable storage drive 514 reads from and/or writes to a removable storage unit 518 in a well-known manner Removable storage unit 518 represents a floppy disk, magnetic tape, optical disk, etc. which is read by and written to by removable storage drive 514. As will be appreciated, the removable storage unit 518 includes a computer usable storage medium having stored therein computer software and/or data.

In alternative embodiments, secondary memory 510 may include other means for allowing computer programs or other instructions to be loaded into computer system 150. Such means may include, for example, a removable storage unit 522 and an interface 520. Examples of such removable storage units/interfaces include a program cartridge and cartridge interface (such as that found in video game devices), a removable memory chip (such as a ROM, PROM, EPROM or EEPROM) and associated socket, and other removable storage units 522 and interfaces 520 which allow software and data to be transferred from the removable storage unit 522 to computer system 150.

The computer system 150 may also include a communications interface 534. Communications interface 534 allows software and data to be transferred between computer system 150 and external devices. Examples of communications interface 534 may include a modem, a network interface (such as an Ethernet card), a communications port (e.g., serial or parallel, etc.), USB port, a PCMCIA slot and card, a modem, etc. Software and data transferred via communications interface 534 are in the form of signals 528 which may be electronic, electromagnetic, optical or other signals capable of being received by communications interface 534. Signals 528 are provided to communications interface 534 via a communications path (i.e., channel) 528. Channel 528 (or any other communication means or channel disclosed herein) carries signals 528 and may be implemented using wire or cable, fiber optics, blue tooth, a phone line, a cellular phone link, an RF link, an infrared link, wireless link or connection and other communications channels.

In this document, the terms "computer program medium" and "computer usable medium" and "computer program product" are used to generally refer to media or medium such as various software, firmware, disks, drives, removable storage drive 514, a hard disk installed in hard disk drive 512, and signals 528. These computer program products ("computer program medium" and "computer usable medium") are means for providing software to computer system 150. The computer program product may comprise a computer useable medium having computer program logic thereon. The invention includes such computer program products. The "computer program product" and "computer useable medium" may be any computer readable medium having computer logic thereon.

Computer programs (also called computer control logic or computer program logic) are may be stored in main memory 508 and/or secondary memory 510. Computer programs may also be received via communications interface 534. Such computer programs, when executed, enable computer system 150 to perform the features of the present invention as discussed herein. In particular, the computer programs, when executed, enable processor 504 to perform functions of the present invention. Accordingly, such computer programs represent controllers of computer system 150.

In an embodiment where the invention is implemented using software, the software may be stored in a computer program product and loaded into computer system 150 using removable storage drive 514, hard drive 512 or communications interface 534. The control logic (software or computer program logic), when executed by the processor 504, causes the processor 504 to perform functions of the invention as described herein.

In another embodiment, the invention is implemented primarily in hardware using, for example, hardware components such as application specific integrated circuits (ASICs) Implementation of the hardware state machine to perform the functions described herein will be apparent to persons skilled in the relevant art(s).

In yet another embodiment, the invention is implemented using a combination of both hardware and software.

In an exemplary software embodiment of the invention, the methods described above may be implemented in SPSS control language or C++ programming language, but could be implemented in other various programs, computer simulation and computer-aided design, computer simulation environment, MATLAB, or any other software platform or program, windows interface or operating system (or other operating system) or other programs known or available to those skilled in the art.

It should be appreciated that various sizes, dimensions, contours, rigidity, shapes, flexibility and materials of any of the embodiments discussed throughout may be varied and utilized as desired or required It should be appreciated that the related components and subsystems discussed herein may take on all shapes along the entire continual geometric spectrum of manipulation of x, y and z planes to provide and meet the anatomical and structural demands and requirements. Unless clearly specified to the contrary, there is no requirement for any particular described or illustrated activity or element, any particular sequence or such activities, any particular size, speed, material, duration, contour, dimension or frequency, or any particularly interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. It should be appreciated that aspects of the present invention may have a variety of sizes, contours, shapes, compositions and materials as desired or required.

In summary, while the present invention has been described with respect to specific embodiments, many modifications, variations, alterations, substitutions, and equivalents will be apparent to those skilled in the art. The present invention is not to be limited in scope by the specific embodiment described herein. Indeed, various modifications of the present invention, in addition to those described herein, will be apparent to those of skill in the art from the foregoing description and accompanying drawings. Accordingly, the invention is to be considered as limited only by the spirit and scope of the following claims, including all modifications and equivalents.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Unless clearly specified to the contrary, there is no requirement for any particular described or illustrated activity or element, any particular sequence or such activities, any particular size, speed, material, dimension or frequency, or any particularly interrelationship of such elements. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all sub ranges therein. Any information in any material (e.g., a United States/foreign patent, United States/foreign patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

EXAMPLE

The following example is put forth so as to provide those of ordinary skill in the art with a complete disclosure and description of how to make and use the present invention, and is not intended to limit the scope of what the inventors regard as their invention nor is it intended to represent that the experiment below is all or the only experiment performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

A purpose of this study was to, among other things, determine whether an intravascular ultrasound catheter could mediate plasmid DNA transfection from microbubble carriers to the porcine coronary artery wall following balloon angioplasty.

An Atlantis SR Pro Intravascular Ultrasound (IVUS) catheter (Boston Scientific, Natick, Mass.) was modified to allow for external excitation from a square wave pulser (SP-801, Ritec Inc., Warwick, R.I.). The center frequency of the negative unipolar pulse was set to 5 MHz, with a PRF of 5 kHz, and amplitude of −590 V. The pressure output of the IVUS transducer at a distance of 1 mm away from the plastic tubing of the catheter sheath was measured by scanning a calibrated hydrophone (GL-0200, Onda Corp., Sunnyvale, Calif.) laterally beyond the width of the transducer. The corresponding −6 dB beamwidth of the IVUS beam was 0.44 mm and produced about 2 MPa at the focus—comparable to acoustic pressures employed by Rahim et al., see Rahim et al., "Spatial and acoustic pressure dependence of microbubble-mediated gene delivery targeted using focused ultrasound", Journal of Gene Medicine, vol. 8, pp. 1347-1357, 2006, which is hereby incorporated herein, in its entirety, by reference thereto.

Rat vascular smooth muscle cells were cultured in vitro in acoustically transparent OPTICELL™ (Biocrystal, Westerville, Ohio) chambers for twenty-four hours to reach about 75% confluency. Plasmids encoding red fluorescent protein (CMV-RFP) were electrostatically coupled to the surface of cationic lipid microbubbles (30 µg/150e8 bubbles) as previously described and injected into the OPTICELL™. The OPTICELL™ was submersed in a 37° C. water bath and the IVUS transducer was translated at a speed of 1.5 mm/s along parallel lines (0.5 mm apart) across the OPTICELL™ exposing 1×2 cm areas of cells to ultrasound (n=3) only once. During this six minute exposure each cell was insonated for approximately only 0.3 seconds (based on the beamwidth). The cells were allowed to grow for twenty-four hours and then analyzed for RFP gene expression using fluorescence microscopy (excitation 512 nm). An average of 0.17% of cells 2702 were successfully transfected following microbubble and IVUS delivery whereas no significant transfection was observed in cells 2704 exposed only to the plasmid coupled microbubbles, see FIG. 28A. Although the transfection efficiency was low it is comparable to other studies, such as Rahim et al., incorporated above, and may be an effect of the narrow beam width (−6 dB) of the IVUS transducer (<0.5 mm) An estimated 12% of cells were located outside the −6 dB beamwidth and may not have been exposed to the sufficient ultrasound intensities. Phase contrast images of insonated and non-insonated regions of cells revealed a 52% difference in cell densities as shown by the cell density 2704' of non-insonated cells compared to cell density 2702' of insonated cells in FIG. 28B.

Figures 28A, 28B:
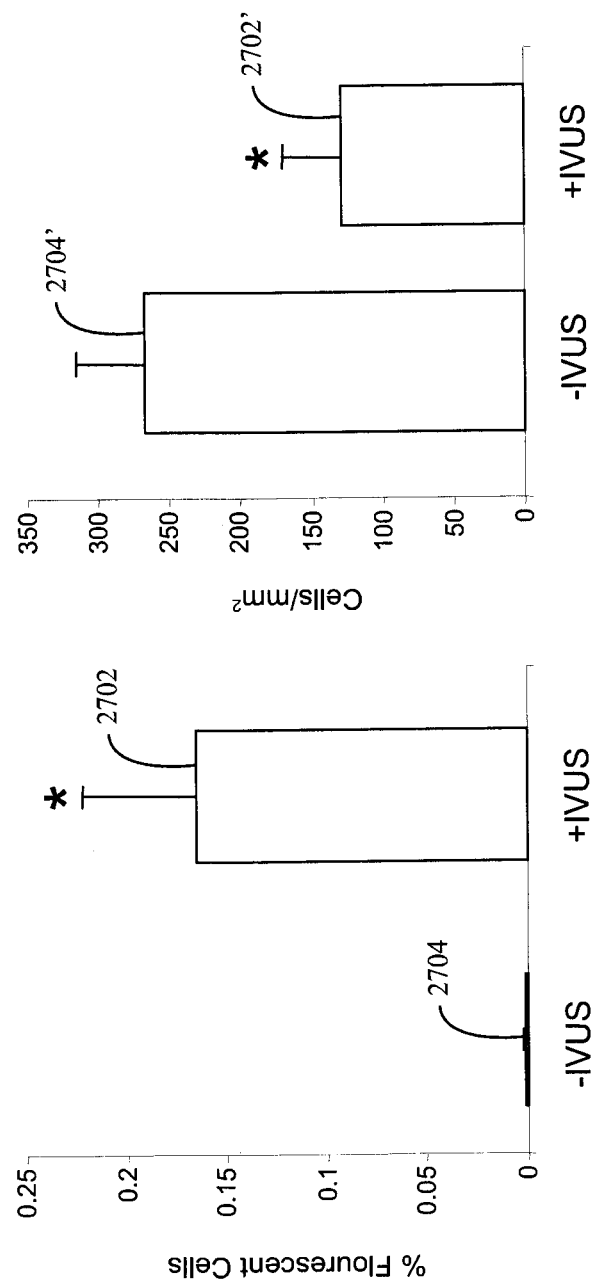
FIGS. 28A-28B illustrate results of an in vitro study of CMV-RFP following plasmid-coupled microbubble delivery and insonation according to an embodiment of the present invention.

As a result of in vitro expression of CMV-RFP following plasmid-coupled microbubble delivery and insonation with a modified intravascular ultrasound catheter to aortic smooth muscle cells, FIG. 28A shows in vitro transfection efficiency presented as percent fluorescent cells in the absence (2704) or presence (2702) of IVUS, (n=3, errors bars represent standard deviation, p=0.0028). FIG. 28B. shows that IVUS exposure decreased SMC viability by ~52% as indicated by cell densities at 24 hours post-insonation, (n=3, errors bars represent standard deviation, p=0.0047).

Figure 29:
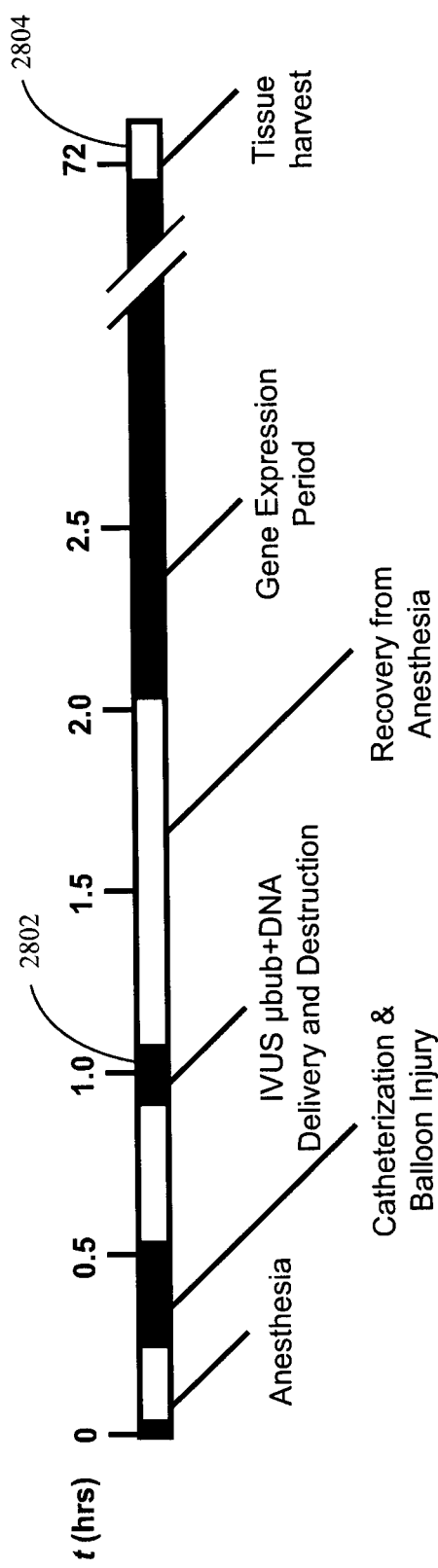
FIG. 29 shows a timeline describing experimental procedures performed in an in vivo study of plasmid-coupled microbubble delivery and insonation in a left anterior descending (LAD) coronary artery of a pig, according to an embodiment of the present invention.

Balloon angioplasty was performed on a porcine left anterior descending (LAD) coronary artery in vivo, as previously described; see also Tharp et al., "Local delivery of the K(Ca)3.1 blocker, TRAM-34, prevents acute angioplasty-induced coronary smooth muscle phenotypic modulation and limits stenosis", Arteriosclerosis, Thrombosis and Vascular Biology, vol. 28, pp. 1084-1089, 2008, which is hereby incorporated herein, in its entirety, by reference thereto. Following angioplasty, plasmid-conjugated microbubbles were infused through the IVUS guide catheter located 2 cm upstream of the transducer. Co-localization of the transducer to the original site of angioplasty was determined by angiography. For the duration of microbubble injection (about 4 min., see 2802, FIG. 29), the site of angioplasty was exposed to IVUS. FIG. 29 shows a timeline for a 35 kg male pig that was anesthetized and catheterized. Balloon injury was performed via angioplasty (1.3:1.0 inflation ratio) for twenty minutes. Following the injury, plasmid (CMV-RFP)-coated microbubbles were infused through a circuit-modified intravascular ultrasound (IVUS) catheter to the site of injury. Insonation was performed by the IVUS probe at 5 MHz, 1 MPa. Seventy-two hours following plasmid-microbubble insonation the vessels were removed from the euthanized animal and processed for frozen histological cross sectioning, staining and analysis. After the seventy-two hour (three day) recovery period, the arteries were excised 2804 and processed for frozen sectioning and nuclei staining (DAPI). Three arbitrary, 6 µm thick slices, spaced 1 mm apart, were analyzed from the angioplasty LAD and control right common carotid (RCC), which received plasmid-microbubble exposure, but no IVUS. Transfection efficiency was observed by fluorescence microscopy and was present only in perimeter cells of the luminal wall.

FIG. 30A is a set of images around the circumference of one of the slices referred to above that shows that in vivo expression of CMV-RFP following plasmid-coupled microbubble delivery and insonation with a modified intravascular ultrasound catheter to a swine coronary artery following angioplasty was localized to the innermost cells 2902 of the LAD coronary artery 2900. FIG. 30B is a higher magnification of the image shown within box "B" of FIG. 30A, wherein the white bar 2904 illustrates a scale of 100 µm. FIG. 30C is a bar chart that graphs gene transfection expressed as percent fluorescent cells+/−one standard deviation in the right carotid artery 2912 of the pig (which was not insonated, i.e., application of angioplasty and DNA-coated microbubbles was performed, but no insonation) compared to the LAD 2914 of the pig (which was insonated, i.e., angioplasty and DNA-coated microbubbles and insonation was applied) in the same animal (n=3 slices, error bars represent standard deviation, p=0.0063). FIGS. 30D-30E show images of the carotid artery 2922 (FIG. 30D) and LAD 2924 (FIG. 30E) that were the subjects of the graphs in FIG. 30C. The white bars 2934 in FIGS. 30D and 30E each illustrate a scale of 50 µM. Quantification of efficiency was calculated as the mean percentage of vessel perimeter cells expressing. LAD with IVUS exposure resulted in 23.3±6.0% transfection whereas the right common carotid (RCC) resulted in 3.6±2.6% transfection—a 6.5 fold increase in transfection efficiency due to insonation by IVUS. A student's t-test was performed to determine significance for both in vitro and in vivo results.

The results demonstrate that, among other things, IVUS is capable of enhancing gene transfection to an injured coronary artery wall using the ultrasound conditions described herein. The above study demonstrates that, following routine angioplasty and during the same procedure, microbubble-mediated gene delivery can be performed in a focused manner using IVUS, avoiding many of the limitations previously mentioned. It is contemplated that future studies using novel modifications to IVUS, e.g. changes in output pressure, should be achievable, and it should be appreciated that it is contemplated as part of the present invention, to provide greater transfection efficiency and deeper penetration of the plasmid DNA in the vessel wall.

REFERENCES

The following patents, applications and publications as listed below are each hereby incorporated in their entireties, by reference thereto. The devices, systems, and methods of various embodiments of the invention disclosed herein may utilize aspects disclosed in the following references, applications, publications and patents and which are hereby incorporated by reference herein in their entirety:

1. U.S. Pat. No. 6,626,861, Sep. 30, 2003, "Balloon catheter apparatus and method", Hart, et al.
2. U.S. Patent Application Publication No. 2006/0235501, Oct. 19, 2006, "Stent supplying device", Igaki, et al.
3. U.S. Patent Application Publication No. 2007/0055132, Mar. 8, 2007, "Catheter device," Camus, et al.
4. U.S. Pat. No. 5,868,708, Feb. 9, 1999, "Balloon catheter apparatus and method", Hart, et al.
5. U.S. Patent Application Publication No. 2006/0189928, Aug. 24, 2006, "Catheter device", Camus, et al.
6. U.S. Patent Application Publication No. 2008/0243233, Oct. 2, 2008, "Device and Methods for Treatment of Vascular Bifurcations", Ben-Muvhar, et al.
7. U.S. Pat. No. 5,222,970, Jun. 29, 1993, "Method of and system for mounting a vascular occlusion balloon on a delivery catheter", Reeves, et al.
8. U.S. Pat. No. 5,707,354, Jan. 13, 1998, "Compliant catheter lumen and methods", Salmon, et al.
9. U.S. Patent Application Publication No. 2003/0163192, Aug. 28, 2003, "Methods for vascular reconstruction of diseased arteries", Wallace, et al.
10. U.S. Patent Application Publication No. 2002/0169496, Nov. 14, 2002, "Methods for vascular reconstruction of diseased arteries", Wallace, et al.
11. U.S. Patent Application Publication No. 2008/0103443, May 1, 2008, "Balloon catheter for treating hardened lesions", Kabrick, et al.
12. U.S. Pat. No. 6,565,601, May 20, 2003, "Methods for vascular reconstruction of diseased arteries, Wallace, et al.
13. U.S. Pat. No. 5,827,171, Oct. 27, 1998, "Intravascular circulatory assist device", Dobak, et al.
14. U.S. Pat. No. 7,011,677, Mar. 14, 2006, "Methods for vascular reconstruction of diseased arteries", Wallace, et al.
15. U.S. Pat. No. 5,941,870, Aug. 24, 1999, "Catheter system having a balloon angioplasty device disposed over a work element lumen", Jang, et al.
16. U.S. Patent Application Publication No. 2004/0158308, Aug. 12, 2004, "Delivery catheter for ribbon-type prosthesis and methods of use", Hogendijk, et al.
17. U.S. Patent Application Publication No. 2006/0161103, "Catheter systems and methods for their use in the treatment of calcified vascular occlusions", Constantz, et al.
18. U.S. Patent Application Publication No. 2003/0199820, Oct. 23, 2003, "Catheter systems and methods for their use in the treatment of calcified vascular occlusions", Constantz, et al.
19. U.S. Patent Application Publication No. 2002/0044907, Apr. 18, 2002, "Catheter systems and methods for their use in the treatment of calcified vascular occlusions", Constantz, et al.
20. U.S. Patent Application Publication No. 2007/0049867, "System for treating chronic total occlusion caused by lower extremity arterial disease", Shindelman, et al.
21. U.S. Pat. No. 5,041,089, Aug. 20, 1991, "Vascular dilation catheter construction", Mueller, et al.
22. U.S. Pat. No. 5,755,707, May 26, 1998, "Vascular dilating catheter", Miyagawa, et al.
23. U.S. Patent Application Publication No. 2004/0111145, Jun. 10, 2004, "Vascular prosthesis for the treatment of abdominal aortic aneurysms, using a combined laparoscopic/open and endovascular technique, and delivery system for releasing a prosthesis fitted with anchoring stents", Serino, et al.
24. U.S. Patent Application Publication No. 2007/0043389, Feb. 22, 2007, "System for treating chronic total occlusion caused by lower extremity arterial disease", Shindelman, et al.
25. U.S. Patent Application No. 2003/0220666, Nov. 27, 2003, "Solid embolic material with variable expansion", et al.
26. U.S. Pat. No. 5,117,831, Jun. 2, 1992, "Vascular catheter having tandem imaging and dilatation components", Jang, et al.
27. U.S. Pat. No. 6,527,979, Mar. 4, 2003, "Catheter systems and methods for their use in the treatment of calcified vascular occlusions", Constantz, et al.
28. U.S. Pat. No. 5,447,503, Sep. 5, 1995, "Guiding catheter tip having a tapered tip with an expandable lumen", Miller, et al.
29. U.S. Pat. No. 7,198,637, Apr. 3, 2007, "Method and system for stent retention using an adhesive", Deshmukh, et al.
30. U.S. Pat. No. 5,415,634, May 16, 1995, "Catheter having helical inflation lumen", Glynn, et al.
31. U.S. Pat. No. 7,078,015, Unger, "Ultrasound Imaging and Treatment", Jul. 18, 2006.
32. U.S. Patent Application Publication No. 2005/017725 A1, Hunter, William L., et. al, "Medical Implants and Anti-Scarring Agents", Aug. 11, 2005.
33. U.S. Patent Application Publication No. 2002/0082680 A1, Shanley, John F., et. al., "Expandable Medical Device for Delivery of Beneficial Agent", Jun. 27, 2002.
34. U.S. Patent Application Publication No. 2003/0181973 A1, Sahota, Harvinder, "Reduced Restinosis Drug Containing Stents", Sep. 25, 2003.
35. U.S. Patent Application Publication No. 2003/0206960 A1, Iversen, Patrick L., et. al., "Delivery of Microparticle-Conjugated Drugs for Inhibition of Stenosis", Nov. 6, 2003.
36. U.S. Patent Application Publication No. 2003/0207907 A1, Iversen, Patrick L., et. al., "Delivery of Microparticle-Conjugated Drugs for Inhibition of Stenosis", Nov. 6, 2003.
37. U.S. Patent Application Publication No. 2004/0077948 A1, Violante, Michael R., "Echogenic Coatings with Overcoat", Apr. 22, 2004.
38. U.S. Patent Application Publication No. 2004/0126400 A1, Iversen, Patrick L., et. al., "Delivery of Therapeutic Compounds Via Microparticles or Microbubbles", Jul. 1, 2004.
39. U.S. Patent Application Publication No. 20040236414, Brar, Balbir S., et. al., "Devices and Methods for Treatment of Stenotic Regions", Nov. 25, 2004.
40. U.S. Patent Application Publication No. 2004/0254635 A1, Shanley, John F., et. al., "Expandable Medical Device for Delivery of Beneficial Agent", Dec. 16, 2004.
41. U.S. Patent Application Publication No. 2007/0010577 A1, Lanza, Gregory, M., et. al., "Targeted Atherosclerosis Treatment", Jan. 11, 1007.
42. U.S. Patent Application Publication No. 2007/0003528 A1, Consigny, Paul, et. al., "Intracoronary Device and Method of Use Thereof, Jan. 4, 2007.
43. U.S. Pat. No. 6,409,667, Hossack, et. al., "Medical Diagnosis Ultrasound Transducer System and Method for Harmonic Imaging", Jun. 25, 2002.
44. U.S. Pat. No. 7,341,569 to Soltani, et al., "Treatment of Vascular Occlusions Using Ultrasonic Energy and Microbubbles", Mar. 11, 2008.

45. U.S. Pat. No. 5,770,222 to Unger, et al., "Therapeutic Drug Delivery Systems", Jun. 23, 2008.
46. PCT International Application No. Serial No. PCT/US2008/056643, filed Mar. 12, 2008, entitled, "Access Needle Pressure Sensor Device and Method of Use,"
47. PCT International Application No. Serial No. PCT/US2008/056816, filed Mar. 13, 2008, entitled, "Epicardial Ablation Catheter and Method of Use,"
48. PCT International Application No. Serial No. PCT/US2008/057626, filed Mar. 20, 2008, entitled, "Electrode Catheter for Ablation Purposes and Related Method Thereof".
49. Thorn, T., et al., Heart disease and stroke statistics—2006 update: a report from the American Heart Association Statistics Committee and Stroke Statistics Subcommittee. CIRCULATION, 2006. 113(6): p. e85-e151.
50. Kandzari, D. E., et al., Frequency, Predictors, and Outcomes of Drug-Eluting Stent Utilization in Patients With High-Risk N on-ST-Segment Elevation Acute Coronary Syndromes, the American Journal of Cardiology, 2005. 96(6): p. 750-755.
51. Rao, S. V., et al., On-Versus Off-Label Use of Drug-Eluting Coronary Stents in Clinical Practice (Report from the American College of Cardiology National Cardiovascular Data Registry [NCDR]). The American Journal of Cardiology, 2006. 97(10): p. 1478-1481.
52. FDA, Circulatory Systems Devices Advisory Panel, 7-8 Dec. 2006. Transcript: http://www.accessdata.fda.gov/scripts/cdrh/cfdocs/cfAdvisory/details.cfm?mtg=672, 2006.
53. Hendrix, J., et al., 5' CArG degeneracy in smooth muscle {alphaj-actin is required for injury-induced gene suppression in vivo. J. Clin. Invest., 2005. 115(2): p. 418-427.
54. McDonald, O., et al., Control of SRF binding to CArG box chromatin regulates smooth muscle gene expression in vivo. J. Clin. Invest., 2006. 116(1): p. 36-48.
55. Owens, G., M. Kumar, and B. Wamhoff, Molecular Regulation of Vascular Smooth Muscle Cell Differentiation in Development and Disease. Physiol. Rev., 2004. 84(3): p. 767-801.
56. Wamhoff, B., et al., L-type Voltage-Gated Ca2+ Channels Modulate Expression of Smooth Muscle Differentiation Marker Genes via a Rho Kinase/Myocardin/SRF-Dependent Mechanism. Circulation Research, 2004. 95(4): p. 406-414.
57. Braun, M., et al., Cellular adhesion molecules on vascular smooth muscle cells. Cardiovascular Research, 1999. 41(2): p. 395-401.
58. Braun-Dullaeus, R., et al., Cell cycle-dependent regulation of smooth muscle cell activation. Arterioscler Thromb Vase Biol, 2004. 24: 845-850, 2004: p. 845-850.
59. Landry, D., et al., Activation of the NF-kappa B and I kappa B system in smooth muscle cells after rat arterial injury. Induction of vascular cell adhesion molecule-1 and monocyte chemoattractant protein-1. Am J Pathol, 1997. 151(4): p. 1085-1095.
60. Parry, T., et al., Drug-eluting stents: sirolimus and paclitaxel differentially affect cultured cells and injured arteries. Eur J Pharmacol, 2005. 524(1-3): p. 19-29.
61. Wessely, R., A. Schomig, and A. Kastrati, Sirolimus and Paclitaxel on Polymer-Based Drug-Eluting Stents: Similar But Different. Journal of the American College of Cardiology, 2006. 47(4): p. 708-714.
62. Webster, A., et al., Target of rapamycin inhibitors (sirolimus and everolimus) for primary immunosuppression of kidney transplant recipients: a systematic review and meta-analysis of randomized trials. Transplantation, 2006. 81(9): p. 1234-1248.
63. Ross, R., The pathogenesis of atherosclerosis: a perspective for the 1990s. Nature, 1993. 362: p. 801-809.
64. Dengler, T. and T. Pober, Cellular and molecular biology of cardiac transplant rejection. Journal of Nuclear Cardiology, 2000. 7: p. 669-685.
65. Sheridan, F., P. Cole, and D. Ramage, Leukocyte adhesion to the coronarymicrovasculature during ischemia and reperfusion in an in vivo canine model. CIRCULATION, 1996. 93: p. 1784-1787.
66. Villanueva, F., A. Klibanov, and W. Wagner, Microbubble-endothelial cell interactions as a basis for assessing endothelial function. ECHOCARDIOGRAPHY, 2002. 19: p. 427-438.
67. Klibanov, A. L., Targeted Delivery of Gas-Filled Microspheres, Contrast Agents for Ultrasound Imaging. Advanced Drug Delivery Reviews, 1999. 37: p. 139-157.
68. Klibanov, A., et al., Targeted ultrasound contrast agent for molecular imaging of inflammation in high-shear flow. Contrast Media and Molecular Imaging, 2006. 1(6): p. 259-266.
69. Rosenschein, U., et al., Ultrasound Imaging-Guided Noninvasive Ultrasound Thrombolysis. CIRCULATION, 2000. 102: p. 238.
70. Unger, E. and D. Yellohair, Methods and apparatus for performing diagnostic and therapeutic ultrasound simultaneously U.S. Pat. No. 5,558,092, 1996.
71. Chan, An image-guided high intensity focused ultrasound device for uterine fibroids treatment. Medical Physics, 2002. 29(11): p. 2611-20.
72. Vaezy, S., et al., Ultrasound image-guided therapy. Academic Radiology, 2003. 10(8): p. 956. 25. Vaezy, S., et al., High intensity focused ultrasound for hemostasis of femoral artery catheter wounds. Ultrasound in Medicine and Biology, 2006. 32(5 Supplement 1): p. 100.
73. Crum, L., Guided High Intensity Focused Ultrasound (HIFU) for Mission-Critical Care.
74. Bouakaz, A., F. Cate, and N. de Jong, A new ultrasonic transducer for improved contrast nonlinear imaging. Physics in Medicine & Biology, 2004. 49(16): p. 3515-3525.
75. Forsberg, F., et al., Design and acoustic characterization of a multifrequency harmonic array for nonlinear contrast imaging. Proceeding of 2001 IEEE Ultrasonics Symposium, 2001. 2: p. 1721-1724.
76. Rychak, J., A. Klibanov, and J. Hossack, Acoustic Radiation Force Enhances Targeted Delivery of Ultrasound Contrast Microbubbles: In vitro Verification. IEEE Transactions on Ultrasonics Ferroelectrics & Frequency Control, 2005. 52(3): p. 421-433.
77. Marx, S., et al., Rapamycin-FKBP Inhibits Cell Cycle Regulators of Proliferation in Vascular Smooth Muscle Cells. Circulation Research, 1995. 76(3): p. 412-417.
78. Klibanov, A., et al., Attachment of ligands to gas-filled microbubbles via PEG spacer and lipid residues anchored at the interface. Proc. Intl. Symp. Control. Rd. Bioact. Mat., 1999. 26: p. 124-125.
79. Wilson, T., et al., The ultrasonix 500RP: A commercial ultrasound research interface. IEEE Transactions Ultrasonics, Ferroelectrics and Frequency Control, 2006. 53(10): p. 1772-1782.
80. Takalkar, A., et al., Binding and detachment dynamics of microbubbles targeted to P-selectin under controlled shear flow. Journal of Controlled Release, 2004. 96(3): p. 473-482.
81. Klibanov, A., et al., Detection of individual microbubbles of an ultrasound contrast agent: fundamental and pulse inversion imaging. Academic Radiology, 2002: p. S279-S281.
82. Jayaweera, A., et al., In vivo myocardial kinetics of air-filled albumin microbubbles during myocardial contrast echocardiography. Comparison with radiolabeled red blood cells. Circulation Research, 1994. 74(6): p. 1157-1165.
83. Springer, T., Adhesion receptors of the immune system. Nature, 1990. 347: p. 425-434.
84. Dayton, P., et al., Acoustic radiation force in vivo: a mechanism to assist targeting of microbubbles. Ultrasound in Medicine & Biology, 1999. 25(8): p. 1195-1201.
85. Fowlkes, J., et al., The role of acoustic radiation force in contrast enhancement techniques using bubble-based ultrasound contrast agents. Journal of the Acoustical Society of America, 1993. 93: p. 2348.
86. Zhao, S., et al., Radiation force assisted targeting facilitates ultrasonic molecular imaging. Molecular Imaging, 2004. 3: p. 1-14.
87. Shortencarier, J., et al., A method for radiation-force localized drug delivery using gas-filled liposheres. IEEE Trans. Ultrasonics, Ferroelectrics and Frequency Control, 2004. 51: p. 822-831.
88. Dayton, P., et al., A preliminary evaluation of the effects of primary and secondary radiation forces on acoustic contrast agents. IEEE Transactions on Ultrasonics Ferroelectrics & Frequency Control, 1997. 44(6): p. 1264-1277.
89. Dayton, P., J. Allen, and K. Ferrara, The magnitude of radiation force on ultrasound contrast agents. Journal of the Acoustical Society of America, 2002. 112: p. 2183-2192.
90. Bosse, R. and D. Vestweber, Only simultaneous blocking of the L- and P-selectin completely inhibits neutrophil migration into mouse peritoneum. European Journal of Immunology, 1994. 24: p. 3019-3024.
91. Lindner, J., et al., Ultrasound Assessment of Inflammation and Renal Tissue Injury With Microbubbles Targeted to P-Selectin. CIRCULATION, 2001. 104 (17): p. 2107-2112.
92. Burns, P., S. Wilson, and D. Simpson, Pulse inversion imaging of liver blood flow: improved method for characterizing focal masses with microbubble contrast. Invest Radiol, 2000. 35(1): p. 71.
93. BrockFisher, G. A., M. D. Poland, and P. G. Rafter, Means for increasing sensitivity in non-linear ultrasound imaging systems U.S. Pat. No. 5,577,505, 1996.
94. Phillips, P., Contrast Pulse Sequences (CPS): Imaging non-linear microbubbles. Proceedings of the 2001 IEEE Ultrasonics Symposium, 2001. 2: p. 1739-1745.
95. Klibanov, A., et al., Proceedings of 26th International Symposium on Controlled Release of Bioactive Materials, Boston. Controlled Release Society, 1999: p. 124-125.
96. Unger, E., et al., Acoustically active liposheres containing paclitaxel—A new therapeutic ultrasound contrast agent. Investigative Radiology, 1998. 33: p. 886-892.
97. Boudennaia, T. Y. and K X. Napoli, Validation of a practical liquid chromatography with ultraviolet detection method for quantification of whole-blood everolimus in a clinical TDM laboratory. Therapeutic Drug Monitoring, 2005. 27(2): p. 171-177.
98. Lindner, J. R., et al., Ultrasound assessment of inflammation and renal tissue injury with microbubbles targeted to P-selectin. Circulation, 2001. 104(17): p. 2107-2112.
99. Klibanov, A., et al., Polymeric sialyl Lewis X microbubbles: targeted ultrasound contrast agents for molecular imaging of inflammation. RSNA Abstract Book, 2006(Abs. # SSK06-06): p. 436-7.
100. B. A. Kaufmann, J. M. Sanders, C. Davis, A. Xie, P. Aldred, I. J. Sarembock, and J. R. Lindner, "Molecular imaging of inflammation in atherosclerosis with targeted ultrasound detection of vascular cell adhesion molecule-1," *Circulation*, vol. 116, pp. 276-84, 2007.
101. B. Kaufmann, C. W. Lewis, A. Xie, A. Mirza-Mohd, and J. Lindner, "Detection of recent myocardial ischaemia by molecular imaging of P-selectin with targeted contrast echocardiography.," *Eur Heart J*, vol. 16, pp. 2011-2017, 2007.
102. P. Dayton, D. Pearson, J. Clark, S. Simon, P. Schumann, R. Zutcshi, T. Matsunaga, and K. Ferrara, "Ultrasonic Analysis of Peptide- and Antibody-Targeted Microbubble Contrast Agents for Molecular Imaging of AVB3-Expressing Cells," *Molecular Imaging*, vol. 3, pp. 125-134, 2004.
103. J. Rychak, A. Klibanov, and J. Hossack, "Acoustic Radiation Force Enhances Targeted Delivery of Ultrasound Contrast Microbubbles: In vitro Verification," *IEEE Transactions on Ultrasonics Ferroelectrics & Frequency Control*, vol. 52, pp. 421-433, 2005.
104. J. Rychak, A. Klibanov, K. Ley, and J. Hossack, "Enhanced Targeting of Ultrasound Contrast Agents Using Acoustic Radiation Force," *Ultrasound in Medicine & Biology*, vol. 33, pp. 1132-1139, 2007.
105. D. Goertz, E. Cherin, A. Needles, R. Karshafian, A. Brown, P. Burns, and F. Foster, "High Frequency Nonlinear B-Scan Imaging of Microbubble Contrast Agents," *IEEE Trans. Ultrasonics, Ferroelectrics and Frequency Control*, vol. 52, pp. 65-79, 2005.
106. G. Maltezos, J. Johnston, and A. Axel Scherer, "Thermal management in microfluidics using micro-Peltier junctions," *Appl Phys Lett*, vol. 87, pp. 154105 (1-3), 2005.
107. F. Liu, D. Sag, J. Wang, L. Shollenberger, F. Niu, X. Yuan, S. Li, M. Thompson, and P. Monahan, "Sinewave Current for Efficient and Safe In Vivo Gene Transfer," *Molecular Therapy: Journal of the American Society of Gene Therapy*, vol. 15, pp. 1842-1847, 2007.
108. F. Gao, B. Qiu, S. Kar, X. Zhan, L. Hofmann, Y. Xiaoming, and Yang, "Intravascular Magnetic Resonance/Radiofrequency May Enhance Gene Therapy for Prevention of In-stent Neointimal Hyperplasia," *Acad. Radiol.*, pp. 526-530, 2006.
109. X. Yang, E. Atalar, and C. Yeung, "Device, systems and methods for localized heating of a vessel and/or in combination with MR/NMR Imaging of the vessel and surrounding tissue," U.S. Pat. No. 7,422,568, 2008.
110. Phillips, L., Klibanov, A. L., Wamhoff, B. R., and Hossack, J. (2007). Targeted Delivery of Plasmid DNA by Ultrasound Following Acute Angioplasty. presented at EMBC.
111. Phillips L C, K. A., Bowles D K, Ragosta M, Hossack J A, Wamhoff B R (2009). Focused In Vivo Delivery of plasmid DNA to the Porcine Vascular Wall via Intravascular Ultrasound (IVUS) Destruction of Microbubbles. J Vasc Res (in press).
112. Zambrowicz, B. P., Imamoto, A., Fiering, S., Herzenberg, L. A., Kerr, W. G., and Soriano, P. (1997). Disruption of overlapping transcripts in the ROSA beta geo 26†gene trap strain leads to widespread expression of beta-galactosidase in mouse embryos and†hematopoietic†cells. Proceedings of the National Academy of Sciences 94, 3789-3794.

That which is claimed is:

1. A method of providing therapy to a treatment site of a subject, said method comprising:
   advancing a distal end portion of an ultrasound catheter to or in proximity to the treatment site;
   dispensing microbubbles from said catheter according to a pacing protocol and in a manner that said microbubbles flow over the treatment site, wherein said dispensing according to said pacing protocol dispenses said bubbles in a timed manner relative to the cardiac cycle of the subject; and
   bursting said microbubbles to dispense drug or gene therapy to the treatment site.

2. The method of claim 1, wherein said bursting is performed by applying acoustic radiation force to said microbubbles, said force being applied from a transducer located within said catheter.

3. The method of claim 1, further comprising viewing the treatment site via ultrasonic imaging provided by applying ultrasonic energy to the treatment site from a transducer located within said catheter.

4. The method of claim 1, wherein the treatment site is at least a portion of a blood vessel, organ, parenchymal tissue, stromal tissue or duct.

5. The method of claim 4, wherein the treatment site is at least a portion of a blood vessel.

6. The method of claim 1, further comprising sensing an ECG waveform of the cardiac cycle of the subject, wherein said pacing is according to the ECG waveform having been sensed.

7. The method of claim 6, further comprising adding a delay period to commencement of dispensing, relative to the ECG waveform, based on distance of the treatment site from the heart of the subject.

8. The method of claim 1, wherein said microbubbles are delivered through a lumen extending through said catheter.

9. The method of claim 1, wherein said microbubbles are formed in said distal end portion of said catheter and dispensed therefrom.

\* \* \* \* \*

SEQUENCE LISTING

```
<160> NUMBER OF SEQ ID NOS: 1

<210> SEQ ID NO 1
<211> LENGTH: 21
<212> TYPE: DNA
<213> ORGANISM: Escherichia coli

<400> SEQUENCE: 1
gactacacaa atcagcgatt t                                                    21
```